(12) United States Patent
Epp et al.

(10) Patent No.: US 8,754,229 B2
(45) Date of Patent: Jun. 17, 2014

(54) 3-ALKOXY, THIOALKYL AND AMINO-4-AMINO-6-(SUBSTITUTED) PICOLINATES AND THEIR USE AS HERBICIDES

(75) Inventors: Jeffrey B. Epp, Noblesville, IN (US); Christian T. Lowe, Westfield, IN (US); James M. Renga, Indianapolis, IN (US); Paul R. Schmitzer, Indianapolis, IN (US); Joseph D. Eckelbarger, Carmel, IN (US); Katherine A. Guenthenspberger, Daleville, IN (US); Thomas L. Siddall, Zionsville, IN (US); Carla N. Yerkes, Crawfordsville, IN (US); Lindsey Gayle Fischer, Indianapolis, IN (US); Natalie Christine Giampietro, Carmel, IN (US); Jeremy Kister, Carmel, IN (US); Joshua Roth, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 5 days.

(21) Appl. No.: 13/538,399

(22) Filed: Jun. 29, 2012

(65) Prior Publication Data

US 2013/0005574 A1    Jan. 3, 2013

Related U.S. Application Data

(60) Provisional application No. 61/502,888, filed on Jun. 30, 2011.

(51) Int. Cl.
*C07D 211/72*  (2006.01)
*A61K 31/44*   (2006.01)

(52) U.S. Cl.
USPC .......................................... 546/290; 514/354

(58) Field of Classification Search
None
See application file for complete search history.

(56) References Cited

U.S. PATENT DOCUMENTS

| | | | |
|---|---|---|---|
| 4,288,599 A | 9/1981 | Nishiyama et al. |
| 4,832,729 A | 5/1989 | Shigematsu et al. |
| 6,297,197 B1 | 10/2001 | Fields et al. |
| 6,784,137 B2 | 8/2004 | Balko et al. |
| 7,300,907 B2 | 11/2007 | Epp et al. |
| 7,314,849 B2 | 1/2008 | Balko et al. |
| 7,642,220 B2 | 1/2010 | Epp et al. |
| 2004/0198608 A1 | 10/2004 | Balko et al. |
| 2005/0032651 A1 | 2/2005 | Balko et al. |
| 2005/0176767 A1 | 8/2005 | Chan Chun Kong et al. |
| 2009/0062125 A1 | 3/2009 | Epp et al. |
| 2011/0034738 A1 | 2/2011 | Pauluth et al. |

FOREIGN PATENT DOCUMENTS

| | | |
|---|---|---|
| JP | 2007204458 A | 8/2007 |
| WO | WO0151468 A1 | 7/2001 |
| WO | WO2005063721 A1 | 7/2005 |
| WO | WO2007020936 A1 | 2/2007 |

OTHER PUBLICATIONS

CAPLUS 2012 885232.*

* cited by examiner

*Primary Examiner* — Heidi Reese
(74) *Attorney, Agent, or Firm* — Donald R. Stuart

(57) ABSTRACT

3-alkoxy, thioalkyl and amino-4-amino-6-(substituted)picolinic acids having a halogen, alkyl or mono-, di- tri- and tetra-substituted aryl substituents in the 6-position, and their acid derivatives, are herbicides demonstrating a broad spectrum of weed control.

17 Claims, No Drawings

3-ALKOXY, THIOALKYL AND AMINO-4-AMINO-6-(SUBSTITUTED)PICOLINATES AND THEIR USE AS HERBICIDES

CROSS REFERENCE TO RELATED APPLICATIONS

This application claims the benefit of U.S. Provisional Patent Application Ser. No. 61/502,888, filed Jun. 30, 2011.

FIELD OF THE INVENTION

This invention relates to certain 3-alkoxy, thioalkyl and amino-4-amino-6-(substituted)picolinates and their derivatives and to the use of these compounds as herbicides.

BACKGROUND OF THE INVENTION

A number of picolinic acids and their pesticidal properties have been described in the art. U.S. Patent Application Publication 2005/0176767 discloses 3-substituted-4-amino-6-substituted picolinamides as human immunodeficiency virus (HIV) integrase inhibitors. U.S. Pat. No. 6,297,197 B2 discloses 3-substituted-4-amino-6-(substituted)picolinic acids and their derivatives and their use as herbicides. JP 2007204458 A and WO 2007020936 A1 disclose compounds that have uses as antimycotic or antifungal agents. U.S. Pat. Nos. 6,784,137 B2 and 7,314,849 B2 disclose a genus of 6-aryl-4-aminopicolinic acids and their derivatives and their use as herbicides. U.S. Pat. Nos. 7,300,907 B2 and 7,642,220 B2 disclose a genus of 2-aryl-6-amino-5-alkoxy-4-pyrimidinecarboxylic acids and their derivatives and their use as herbicides. It has now been discovered that 3-alkoxy, thioalkyl and amino-4-amino-6-(substituted)picolinates exhibit similar herbicidal activity and selectivity.

SUMMARY OF THE INVENTION

Certain 3-alkoxy, thioalkyl and amino-4-amino-6-(substituted)picolinic acids and their derivatives are herbicides with a broad spectrum of weed control against a variety of weeds, including grasses, broadleaves and sedges.

Provided herein are compound of Formula A:

wherein
Q represents $C_1$-$C_4$ alkoxy, $C_1$-$C_4$ haloalkoxy, $SR^3$, or $NR^1R^2$;
X represents H or halogen;
Y represents F, Cl, $C_1$-$C_6$ alkyl, $C_1$-$C_6$ haloalkyl, $C_2$-$C_6$ alkenyl, $C_2$-$C_6$ haloalkenyl, $C_3$-$C_7$ cycloalkyl, $C_3$-$C_7$ halocycloalkyl or Ar;
Ar represents a phenyl group or a pyridine substituted with one to four substituents independently selected from halogen, nitro, cyano, formyl, $C_1$-$C_6$ alkyl, $C_3$-$C_7$ cycloalkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ alkylsulfinyl, $C_1$-$C_6$ alkylsulfonyl, $C_2$-$C_4$ alkenyloxy, $C_2$-$C_4$ alkynloxy, $C_2$-$C_4$ alkenylthio, $C_2$-$C_4$ alkynylthio, $C_1$-$C_6$ haloalkyl, $C_3$-$C_7$ halocycloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, —OCH$_2$CH$_2$—, —OCH$_2$CH$_2$CH$_2$—, —OCH$_2$O—, —OCH$_2$CH$_2$O—, —C(O)OR$^3$, —C(O)NR$^3$R$^4$, —CR$^4$NOR$^3$, —NH$_2$, —NR$^3$R$^4$, —NR$^4$OR$^3$, —NR$^4$SO$_2$R$^3$, —NR$^4$C(O)R$^3$, —NR$^4$C(O)OR$^3$, —NR$^4$C(O)NR$^3$R$^4$ or —NCR$^4$NR$^3$R$^4$;
$R^1$ and $R^2$ independently represent H, $C_1$-$C_6$ alkyl, or $C_1$-$C_6$ acyl;
$R^3$ represents $C_1$-$C_4$ alkyl or $C_1$-$C_4$ haloalkyl; and
$R^4$ represents H, $C_1$-$C_4$ alkyl or $C_1$-$C_4$ haloalkyl;
and agriculturally acceptable derivatives of the carboxylic acid group of the picolinic acid.

In some embodiments, the compound of Formula A is a compound of Formula I:

wherein
Q represents $C_1$-$C_4$ alkoxy or $C_1$-$C_4$ haloalkoxy;
X represents H or halogen;
Y represents F, Cl, $C_1$-$C_6$ alkyl, $C_1$-$C_6$ haloalkyl, $C_2$-$C_6$ alkenyl, $C_2$-$C_6$ haloalkenyl, $C_3$-$C_7$ cycloalkyl, $C_3$-$C_7$ halocycloalkyl or Ar;
Ar represents a phenyl group or a pyridine substituted with one to four substituents independently selected from halogen, nitro, cyano, formyl, $C_1$-$C_6$ alkyl, $C_3$-$C_7$ cycloalkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ alkylsulfinyl, $C_1$-$C_6$ alkylsulfonyl, $C_2$-$C_4$ alkenyloxy, $C_2$-$C_4$ alkynloxy, $C_2$-$C_4$ alkenylthio, $C_2$-$C_4$ alkynylthio, $C_1$-$C_6$ haloalkyl, $C_3$-$C_7$ halocycloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, —OCH$_2$CH$_2$—, —OCH$_2$CH$_2$CH$_2$—, —OCH$_2$O—, —OCH$_2$CH$_2$O—, —C(O)OR$^3$, —C(O)NR$^3$R$^4$, —CR$^4$NOR$^3$, —NH$_2$, —NR$^3$R$^4$, —NR$^4$OR$^3$, —NR$^4$SO$_2$R$^3$, —NR$^4$C(O)R$^3$, —NR$^4$C(O)OR$^3$, —NR$^4$C(O)NR$^3$R$^4$ or —NCR$^4$NR$^3$R$^4$;
$R^1$ and $R^2$ independently represent H, $C_1$-$C_6$ alkyl, or $C_1$-$C_6$ acyl;
$R^3$ represents $C_1$-$C_4$ alkyl or $C_1$-$C_4$ haloalkyl; and
$R^4$ represents H, $C_1$-$C_4$ alkyl or $C_1$-$C_4$ haloalkyl;
and agriculturally acceptable derivatives of the carboxylic acid group of the picolinic acid.

Preferred compounds of Formula A and Formula I independently include those in which Q represents methoxy, X represents H or F, Y represents Ar, Ar represents para-substituted phenyl with or without other substituents, and $R^1$ and $R^2$ represent H.

The invention includes herbicidal compositions comprising an herbicidally effective amount of a compound of Formula A and agriculturally acceptable derivatives of the carboxylic acid group in admixture with an agriculturally acceptable adjuvant or carrier. The invention also includes a method of use of the compounds and compositions of the present invention to kill or control undesirable vegetation by application of an herbicidal amount of the compound to the vegetation or to the locus of the vegetation as well as to the soil or water prior to emergence of the vegetation.

In some embodiments, the compound of Formula A is a compound of Formula I*:

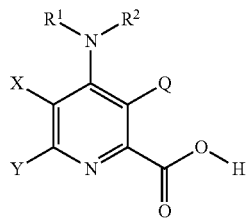

I* wherein

Q represents $SR^3$ or $NR_1R_2$;

X represents H or halogen;

Y represents F, Cl, $C_1$-$C_6$ alkyl, $C_1$-$C_6$ haloalkyl, $C_2$-$C_6$ alkenyl, $C_2$-$C_6$ haloalkenyl, $C_3$-$C_7$ cycloalkyl, $C_3$-$C_7$ halocycloalkyl or Ar;

Ar represents a phenyl group or a pyridine substituted with one to four substituents independently selected from halogen, nitro, cyano, formyl, $C_1$-$C_6$ alkyl, $C_3$-$C_7$ cycloalkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ alkylsulfinyl, $C_1$-$C_6$ alkylsulfonyl, $C_2$-$C_4$ alkenyloxy, $C_2$-$C_4$ alkynloxy, $C_2$-$C_4$ alkenylthio, $C_2$-$C_4$ alkynylthio, $C_1$-$C_6$ haloalkyl, $C_3$-$C_7$ halocycloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, —OCH$_2$CH$_2$—, —OCH$_2$CH$_2$CH$_2$—, —OCH$_2$O—, —OCH$_2$CH$_2$O—, —C(O)OR$^3$, —C(O)NR$^3$R$^4$, —CR$^4$NOR$^3$, —NH$_2$, —NR$^3$R$^4$, —NR$^4$OR$^3$, —NR$^4$SO$_2$R$^3$, —NR$^4$C(O)R$^3$, —NR$^4$C(O)OR$^3$, —NR$^4$C(O)NR$^3$R$^4$ or —NCR$^4$NR$^3$R$^4$;

$R^1$ and $R^2$ independently represent H, $C_1$-$C_6$ alkyl, or $C_1$-$C_6$ acyl;

$R^3$ represents $C_1$-$C_4$ alkyl or $C_1$-$C_4$ haloalkyl;

$R^4$ represents H, $C_1$-$C_4$ alkyl or $C_1$-$C_4$ haloalkyl; and
and agriculturally acceptable derivatives of the carboxylic acid group of the picolinic acid.

The invention also includes compounds of the Formula II

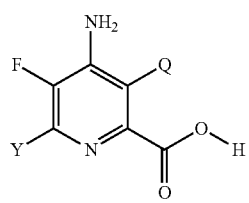

II wherein

Q represents H or I; and

Y represents a phenyl group substituted with one to four substitutents independently selected from halogen, $C_1$-$C_6$ alkoxy or $C_1$-$C_6$ haloalkyl;

and $C_1$-$C_{12}$ esters of the carboxylic acid group of the picolinic acid.

The invention also includes compounds of the Formula III

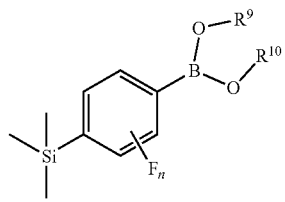

III wherein n is 1 or 2; and $R^9$ and $R^{10}$ independently represent $C_1$-$C_4$ alkyl or $R^9$ and $R^{10}$ taken together represent an ethylene (—CH$_2$CH$_2$—) or propylene (—CH$_2$CH$_2$CH$_2$—) bridge optionally substituted with from 1 to 4 methyl groups.

The invention also includes compounds of the Formula IV

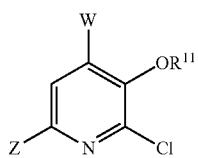

IV wherein

W represents Br or NH$_2$;

Z represents Br or a phenyl group substituted with one to four substitutents independently selected from halogen, $C_1$-$C_6$ alkoxy or $C_1$-$C_6$ haloalkyl; and $R^{11}$ represents H or —CHF$_2$.

The invention also includes compounds of the Formula V

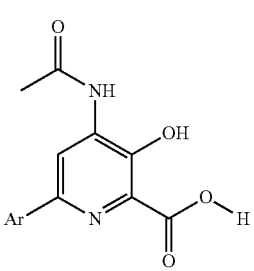

V wherein

Ar represents a phenyl group substituted with one to four substitutents independently selected from halogen, $C_1$-$C_6$ alkoxy or $C_1$-$C_6$ haloalkyl;

and $C_1$-$C_{12}$ esters of the carboxylic acid group of the picolinic acid.

DETAILED DESCRIPTION OF THE INVENTION

Provided herein are compounds of Formula A:

<img, Formula A: picolinic acid structure with R¹R²N- at 4-position, X at 5, Y at 6, Q at 3, and COOH at 2> wherein

Q represents $C_1$-$C_4$ alkoxy, $C_1$-$C_4$ haloalkoxy, $SR^3$, or $NR^1R^2$;

X represents H or halogen;

Y represents F, Cl, $C_1$-$C_6$ alkyl, $C_1$-$C_6$ haloalkyl, $C_2$-$C_6$ alkenyl, $C_2$-$C_6$ haloalkenyl, $C_3$-$C_7$ cycloalkyl, $C_3$-$C_7$ halocycloalkyl or Ar;

Ar represents a phenyl group or a pyridine substituted with one to four substituents independently selected from halogen, nitro, cyano, formyl, $C_1$-$C_6$ alkyl, $C_3$-$C_7$ cycloalkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ alkylsulfinyl, $C_1$-$C_6$ alkylsulfonyl, $C_2$-$C_4$ alkenyloxy, $C_2$-$C_4$ alkynyloxy, $C_2$-$C_4$ alkenylthio, $C_2$-$C_4$ alkynylthio, $C_1$-$C_6$ haloalkyl, $C_3$-$C_7$ halocycloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, —OCH$_2$CH$_2$—, —OCH$_2$CH$_2$CH$_2$—, —OCH$_2$O—, —OCH$_2$CH$_2$O—, —C(O)OR$^3$, —C(O)NR$^3$R$^4$, —CR$^4$NOR$^3$, —NH$_2$, —NR$^3$R$^4$, —NR$^4$OR$^3$, —NR$^4$SO$_2$R$^3$, —NR$^4$C(O)R$^3$, —NR$^4$C(O)OR$^3$, —NR$^4$C(O)NR$^3$R$^4$ or —NCR$^4$NR$^3$R$^4$;

$R^1$ and $R^2$ independently represent H, $C_1$-$C_6$ alkyl, or $C_1$-$C_6$ acyl;

$R^3$ represents $C_1$-$C_4$ alkyl or $C_1$-$C_4$ haloalkyl; and $R^4$ represents H, $C_1$-$C_4$ alkyl or $C_1$-$C_4$ haloalkyl;

and agriculturally acceptable derivatives of the carboxylic acid group of the picolinic acid.

In some embodiments, Q is $C_1$-$C_4$ alkoxy.

In some embodiments, Q is methoxy.

In some embodiments, Q is NH$_2$.

In some embodiments, X is H or F.

In some embodiments, Y is Ar. In certain embodiments, Ar represents para-substituted phenyl with or without other substituents. In particular embodiments, the para-substituted phenyl has no other substitutents. In particular embodiments, the para-substituted phenyl has one other substitutent. In particular embodiments, the para-substituted phenyl has two other substitutents. In particular embodiments, the para-substituted phenyl has three other substitutents. In particular embodiments, the para-substituted phenyl has four other substitutents. In certain embodiments, the other substituent(s) is halogen or $C_{1-6}$ alkoxy.

In some embodiments, Q represents methoxy, X represents H or F, Y represents Ar, Ar represents para-substituted phenyl with or without other substituents, and $R^1$ and $R^2$ represent H.

In some embodiments, the compound of Formula A is a compound of Formula I:

<img, Formula I: picolinic acid structure> wherein

Q represents $C_1$-$C_4$ alkoxy or $C_1$-$C_4$ haloalkoxy;

X represents H or halogen;

Y represents F, Cl, $C_1$-$C_6$ alkyl, $C_1$-$C_6$ haloalkyl, $C_2$-$C_6$ alkenyl, $C_2$-$C_6$ haloalkenyl, $C_3$-$C_7$ cycloalkyl, $C_3$-$C_7$ halocycloalkyl or Ar;

Ar represents a phenyl group or a pyridine substituted with one to four substituents independently selected from halogen, nitro, cyano, formyl, $C_1$-$C_6$ alkyl, $C_3$-$C_7$ cycloalkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ alkylsulfinyl, $C_1$-$C_6$ alkylsulfonyl, $C_2$-$C_4$ alkenyloxy, $C_2$-$C_4$ alkynyloxy, $C_2$-$C_4$ alkenylthio, $C_2$-$C_4$ alkynylthio, $C_1$-$C_6$ haloalkyl, $C_3$-$C_7$ halocycloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, —OCH$_2$CH$_2$—, —OCH$_2$CH$_2$CH$_2$—, —OCH$_2$O—, —OCH$_2$CH$_2$O—, —C(O)OR$^3$, —C(O)NR$^3$R$^4$, —CR$^4$NOR$^3$, —NH$_2$, —NR$^3$R$^4$, —NR$^4$OR$^3$, —NR$^4$SO$_2$R$^3$, —NR$^4$C(O)R$^3$, —NR$^4$C(O)OR$^3$, —NR$^4$C(O)NR$^3$R$^4$ or —NCR$^4$NR$^3$R$^4$;

$R^1$ and $R^2$ independently represent H, $C_1$-$C_6$ alkyl, or $C_1$-$C_6$ acyl;

$R^3$ represents $C_1$-$C_4$ alkyl or $C_1$-$C_4$ haloalkyl; and $R^4$ represents H, $C_1$-$C_4$ alkyl or $C_1$-$C_4$ haloalkyl;

and agriculturally acceptable derivatives of the carboxylic acid group of the picolinic acid.

In some embodiments, the compound of Formula A is a compound of Formula I*:

<img, Formula I*: picolinic acid structure> wherein

Q represents $SR^3$ or $NR_1R_2$;

X represents H or halogen;

Y represents F, Cl, $C_1$-$C_6$ alkyl, $C_1$-$C_6$ haloalkyl, $C_2$-$C_6$ alkenyl, $C_2$-$C_6$ haloalkenyl, $C_3$-$C_7$ cycloalkyl, $C_3$-$C_7$ halocycloalkyl or Ar;

Ar represents a phenyl group or a pyridine substituted with one to four substituents independently selected from halogen, nitro, cyano, formyl, $C_1$-$C_6$ alkyl, $C_3$-$C_7$ cycloalkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ alkylsulfinyl, $C_1$-$C_6$ alkylsulfonyl, $C_2$-$C_4$ alkenyloxy, $C_2$-$C_4$ alkynyloxy, $C_2$-$C_4$ alkenylthio, $C_2$-$C_4$ alkynylthio, $C_1$-$C_6$ haloalkyl, $C_3$-$C_7$ halocycloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, —OCH$_2$CH$_2$—, —OCH$_2$CH$_2$CH$_2$—, —OCH$_2$O—, —OCH$_2$CH$_2$O—, —C(O)OR$^3$, —C(O)NR$^3$R$^4$, —CR$^4$NOR$^3$, —NH$_2$, —NR$^3$R$^4$, —NR$^4$OR$^3$, —NR$^4$SO$_2$R$^3$, —NR$^4$C(O)R$^3$, —NR$^4$C(O)OR$^3$, —NR$^4$C(O)NR$^3$R$^4$ or —NCR$^4$NR$^3$R$^4$;

$R^1$ and $R^2$ independently represent H, $C_1$-$C_6$ alkyl, or $C_1$-$C_6$ acyl;

$R^3$ represents $C_1$-$C_4$ alkyl or $C_1$-$C_4$ haloalkyl;

$R^4$ represents H, $C_1$-$C_4$ alkyl or $C_1$-$C_4$ haloalkyl; and and agriculturally acceptable derivatives of the carboxylic acid group of the picolinic acid.

In certain embodiments, these compounds are characterized by possessing a carboxylic acid group or a derivative thereof in the 2-position; an alkoxy, haloalkoxy, thioalkyl, amino, or aminoalkyl group in the 3-position; an amino or substituted amino group in the 4-position; and a substituent, preferably a mono-, di-, tri- or tetra-substituted phenyl or pyridyl group, in the 6-position of the pyridine ring. Compounds in which methoxy is in the 3-position of the pyridine ring are generally preferred. Preferred substituted aryl groups include para-substituted phenyl with or without other substituents.

Without being limited to any theory, the carboxylic acids of Formula A are believed to be the compounds that actually kill or control undesirable vegetation and are typically preferred. Analogs of these compounds in which the acid group of the picolinic acid is derivatized to form a related substituent that can be transformed within plants or the environment to an acid group possess essentially the same herbicidal effect and are within the scope of the invention. Therefore, an "agriculturally acceptable derivative," when used to describe the carboxylic acid functionality at the 2-position, is defined as any salt, ester, acylhydrazide, imidate, thioimidate, amidine, amide, orthoester, acylcyanide, acyl halide, thioester, thionoester, dithiolester, nitrile or any other acid derivative well known in the art which (a) does not substantially affect the herbicidal activity of the active ingredient, e.g., a 3-alkoxy, thioalkyl and amino-4-amino-6-(substituted)picolinic acid described herein, and (b) is or can be hydrolyzed, oxidized or metabolized in plants or soil to the picolinic acid of Formula A that, depending upon the pH, is in the dissociated or the undissociated form. The preferred agriculturally acceptable derivatives of the carboxylic acid are agriculturally acceptable salts, esters and amides. In some embodiments, the agriculturally acceptable derivative is an $C_{1-8}$ alkyl ester or $C_{6-12}$ arylalkyl ester, e,g, benzyl ester.

Suitable salts include those derived from alkali or alkaline earth metals and those derived from ammonia and amines. Preferred cations include sodium, potassium, magnesium, and aminium cations of the formula:

$R^5R^6R^7R^8N^+$ wherein $R^5$, $R^6$, $R^7$ and $R^8$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^5$, $R^6$, $R^7$ and $R^8$ are sterically compatible. Additionally, any two of $R^5$, $R^6$, $R^7$ and $R^8$ together may represent an aliphatic difunctional moiety containing one to twelve carbon atoms and up to two oxygen or sulfur atoms. Salts of the compounds described hereincan be prepared by treatment of the compound with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide. Amine salts are often preferred forms of the compounds of described herein because they are water-soluble and lend themselves to the preparation of desirable aqueous based herbicidal compositions.

Suitable esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the picolinic acids with the alcohol using any number of suitable activating agents such as those used for peptide couplings such as dicyclohexylcarbodiimide (DCC) or carbonyl diimidazole (CDI); by reacting the picolinic acids with alkylating agents such as alkylhalides or alkylsulfonates in the presence of a base such as triethylamine or lithium carbonate; by reacting the corresponding acid chloride of a picolinic acid of Formula A with an appropriate alcohol; by reacting the corresponding picolinic acid of Formula A with an appropriate alcohol in the presence of an acid catalyst or by transesterification.

Suitable amides include those derived from ammonia or from $C_1$-$C_{12}$ alkyl, $C_3$-$C_{12}$ alkenyl or $C_3$-$C_{12}$ alkynyl mono- or di-substituted amines, such as but not limited to dimethylamine, diethanolamine, 2-methylthiopropylamine, bisallylamine, 2-butoxy-ethylamine, cyclododecylamine, benzylamine or cyclic or aromatic amines with or without additional heteroatoms such as but not limited to aziridine, azetidine, pyrrolidine, pyrrole, imidazole, tetrazole or morpholine, unsubstituted or substituted. Amides can be prepared by reacting the corresponding picolinic acid chloride, mixed anhydride, or carboxylic ester of Formula A with ammonia or an appropriate amine.

The term "alkyl," "aryl-substituted alkyl," "alkenyl" and "alkynyl," as well as derivative terms such as "alkoxy," "acyl," "alkylthio" and "alkylsulfonyl," as used herein, include within their scope straight chain, branched chain and cyclic moieties, unsubstituted or substituted. The terms "alkenyl" and "alkynyl" are intended to include one or more unsaturated bonds.

The term "aryl," as well as derivative terms such as "aryloxy," refers to a phenyl group or a pyridine group substituted with one to four substitutents selected from halogen, nitro, cyano, formyl, $C_1$-$C_6$ alkyl, $C_3$-$C_7$ cycloalkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ alkylsulfinyl, $C_1$-$C_6$ alkylsulfonyl, $C_2$-$C_4$ alkenyloxy, $C_2$-$C_4$ alkynyloxy, $C_2$-$C_4$ alkenylthio, $C_2$-$C_4$ alkynylthio, $C_1$-$C_6$ haloalkyl, $C_3$-$C_7$ halocycloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, —OCH$_2$CH$_2$—, —CH$_2$CH$_2$CH$_2$—, —OCH$_2$O—, —OCH$_2$CH$_2$O—, —C(O)OR$^3$, —C(O)NR$^3$R$^4$, —CR$^4$NOR$^3$, —NH$_2$, —NR$^3$R$^4$, —NR$^4$OR$^3$, —NR$^4$SO$_2$R$^3$, —NR$^4$C(O)R$^3$, —NR$^4$C(O)OR$^3$, —NR$^4$C(O)NR$^3$R$^4$ or —NCR$^4$NR$^3$R$^4$.

Unless specifically limited otherwise, the term "halogen" including derivative terms such as "halo" refers to fluorine, chlorine, bromine and iodine. The terms "haloalkyl" and "haloalkoxy" refer to alkyl and alkoxy groups substituted with from 1 to the maximum possible number of halogen atoms.

The compounds of Formula A, e.g., I and I*, can be made using well-known chemical procedures. The required starting materials are commercially available or readily synthesized utilizing standard procedures.

The 3-alkoxy-4-amino-6-(substituted)picolinates of Formula A, e.g., I and I*, can be prepared in a number of ways. The 3-methoxy-6-chloropicolinate of Formula II can be oxidized to the corresponding pyridine N-oxide of Formula III, as in step a of Scheme I, using urea hydrogen peroxide complex and trifluoroacetic anhydride in a non-reactive solvent such as dichloromethane at a temperature from 0 to 20° C. Chlorination of the pyridine N-oxide of Formula III can be achieved using phosphorus oxychloride at 70 to 100° C., as in step b of Scheme I, to provide a 1:1 mixture of the 5,6- and 4,6-dichloro-3-methoxypicolinates, which after chromatography yields the 4,6-dichloropicolinate of Formula IV. In step $c_1$, the 4-chloro group can be displaced with sodium azide in a polar, aprotic solvent such as N,N-dimethylformamide (DMF) at 50° C. The resulting 4-azido compound can be reduced with sodium borohydride in a polar, protic solvent such as methyl alcohol to give the 4-aminopicolinate of Formula I-A, as in step $d_1$ of Scheme I. Further chlorination of the 4-aminopicolinate of Formula I-A can be accomplished with sulfuryl chloride in a polar, aprotic solvent such as acetonitrile, as in step e of Scheme I, to afford the 5,6-dichloropicolinate of Formula I-B.

Scheme I

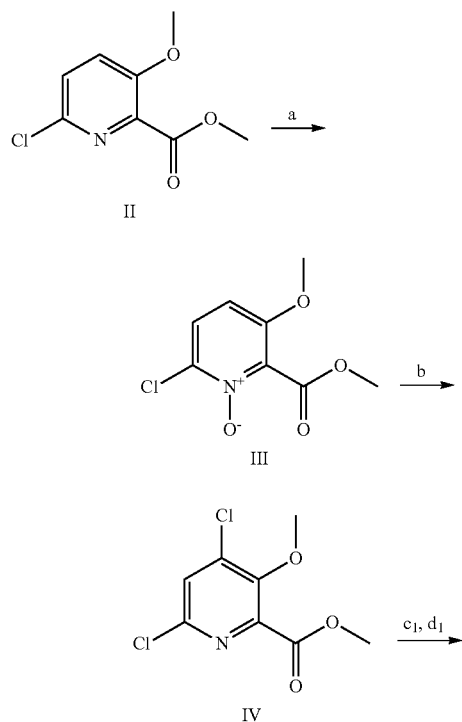

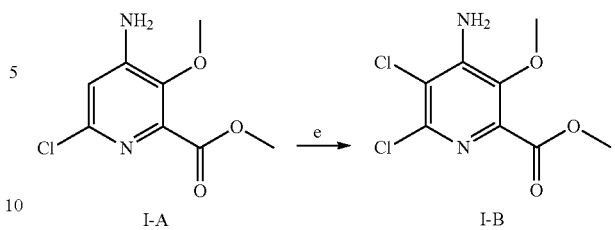

In step $f_1$ of Scheme II, the 6-bromopicolinate of Formula V (synthesized by the procedures found in Kong, L. C. C. et al. WO 2005042524 (2005)) can be converted to the 6-arylpicolinate of Formula VI, wherein Ar is as previously defined, via Suzuki coupling with a boronic acid or ester, in the presence of a catalyst such as bis(triphenylphosphine)-palladium (II) dichloride, cesium fluoride and a polar protic solvent mixture such as 1,2-dimethoxyethane-water at 100° C. in a microwave reactor. The benzyl group can be removed from the compound of Formula VI via hydrogenolysis with hydrogen gas, in the presence of a catalyst such as palladium hydroxide on carbon in a polar, protic solvent such as ethyl alcohol to provide the 3-hydroxypicolinate of Formula VII, wherein Ar is as previously defined, as in step g of Scheme II. In step h, the 3-hydroxy group can be transformed via reaction with triphenylphosphine and diethyl azodicarboxylate in a polar, protic solvent such as methyl alcohol to afford the 3-methoxypicolinate of Formula I-C, wherein Ar is as previously defined. Removal of the 4-acetyl protecting group from the compound of Formula I-C can be accomplished by reaction with acetyl chloride in a polar, protic solvent such as methyl alcohol to yield the 4-aminopicolinate of Formula I-D, wherein Ar is as previously defined. The 4-aminopicolinate of Formula I-D can also be prepared starting from the 6-bromopicolinate, which can be synthesized as in Fields, S. C. et al. U.S. Pat. No. 6,297,197 B1, Oct. 2, 2001. In step $f_2$ of Scheme II, Suzuki coupling of the 6-bromopicolinate of Formula VIII with a boronic acid or ester, in the presence of a catalyst such as bis(triphenylphosphine)palladium(II) dichloride, cesium fluoride and a polar protic solvent mixture such as 1,2-dimethoxyethane-water at 110° C. in a microwave oven, provides the 4-aminopicolinate of Formula I-D, wherein Ar is as previously defined.

Scheme II

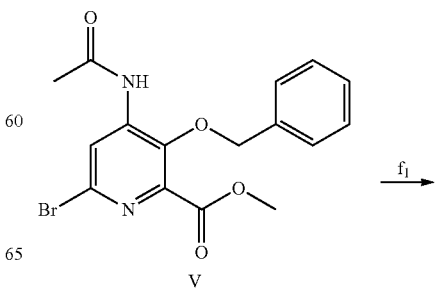

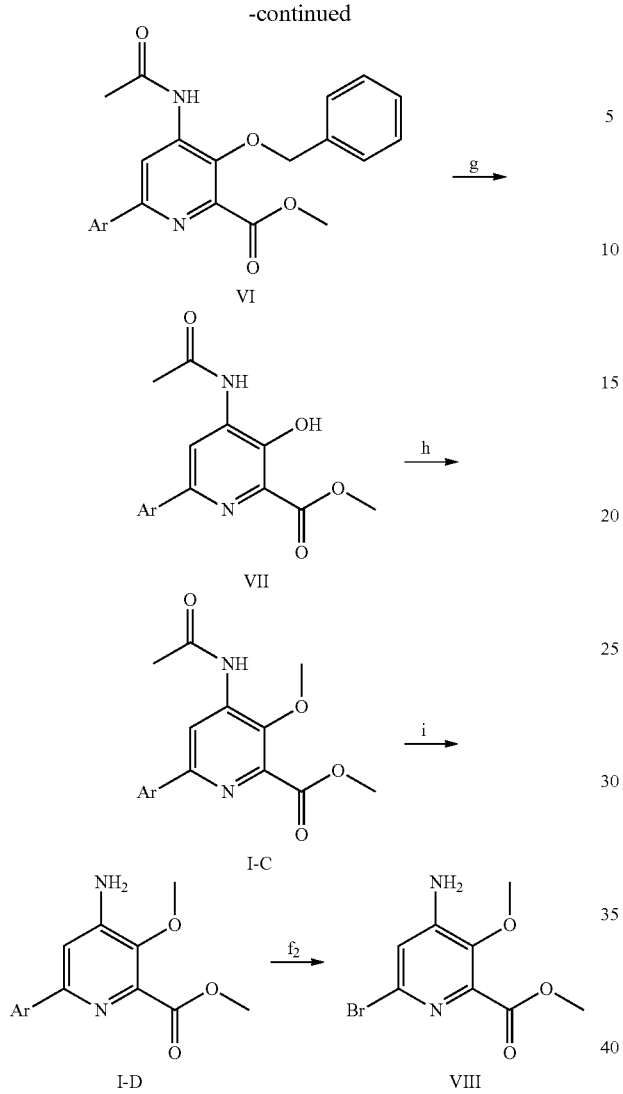

I-D → VIII

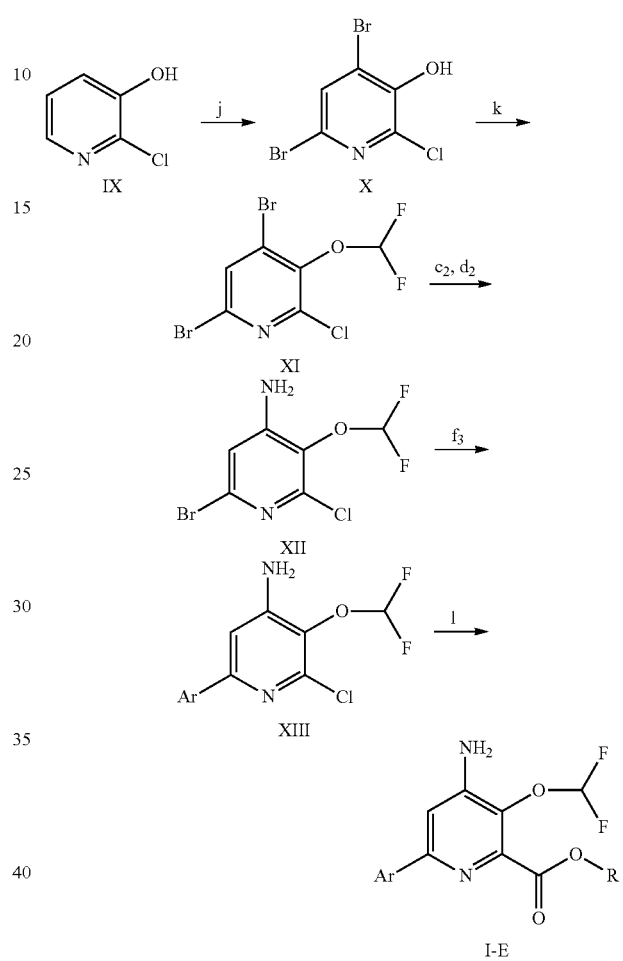

Scheme III

In step j of Scheme III, the 2-chloropyridin-3-ol of Formula IX can be brominated with a brominating reagent such as N-bromosuccinimide in a polar, aprotic solvent such as acetonitrile to afford the 4,6-dibromopyridin-3-ol of Formula X. The 4,6-dibromopyridin-3-ol of Formula X can be transformed into the 3-difluoromethoxy-4,6-dibromopyridine of Formula XI by reaction with 2-chloro-2,2-difluoro-1-phenylethanone in the presence of a polar, aprotic solvent such as acetonitrile at 100° C. in a microwave reactor as in step k. In steps $c_2$ and $d_2$ of Scheme III, the 4-bromo group on the compound of Formula XI can be displaced with sodium azide in a polar, aprotic solvent such as DMF at 65° C. The resulting 4-azido compound can be reduced with sodium borohydride in a polar, protic solvent such as methyl alcohol to give the 4-amino-6-bromopyridine of Formula XII. The 4-amino-6-bromopyridine of Formula XII can be converted to the 6-aryl pyridine of Formula XIII, wherein Ar is as previously defined, via Suzuki coupling with a boronic acid or ester, in the presence of a catalyst such as bis(triphenylphosphine)palladium (II) dichloride, cesium fluoride and a polar protic solvent mixture such as 1,2-dimethoxyethane-water at 110° C. in a microwave reactor, as in step $f_3$ of Scheme III. In step l, the 6-aryl pyridine of Formula XIII can be reacted with carbon monoxide in the presence of a catalyst, such as [1,1'-bis (diphenylphosphino)-ferrocene]dichloropalladium(II), and triethylamine in a polar, protic solvent such as ethyl alcohol at 105° C. in a bomb reactor to provide the 6-arylpicolinate of Formula I-E, wherein Ar is as previously defined.

In step m of Scheme IV, the 4,5,6-trichloropicolinate of Formula XIV can be converted to the corresponding isopropyl ester of Formula XV, via reaction with isopropyl alcohol and concentrated sulfuric acid at reflux temperature under Dean-Stark conditions. The isopropyl ester of Formula XV can be reacted with a fluoride ion source such as cesium fluoride in a polar, aprotic solvent such as dimethyl sulfoxide at 80° C. under Dean-Stark conditions to yield the isopropyl 4,5,6-trifluoropicolinate of Formula XVI, as in step n of Scheme IV. In step o, the isopropyl 4,5,6-trifluoropicolinate of Formula XVI can be aminated with a nitrogen source such as ammonia in a polar, aprotic solvent such as dimethyl sulfoxide to produce a 4-amino-5,6-difluoropicolinate of Formula XVII. The fluoro substituent in the 6-position of the 4-amino-5,6-difluoropicolinate of Formula XVII can be exchanged with a chloro substituent by treatment with a chloride source, such as hydrogen chloride in dioxane, in a Parr reactor at 100° C. to produce a 4-amino-5-fluoro-6-chloropicolinate of Formula XVIII, as in step p in Scheme IV. In step q, the 4-amino-5-fluoro-6-chloropicolinate of Formula XVIII is transesterified to the corresponding methyl ester of Formula XIX by reaction with titanium(IV) isopropoxide in methyl alcohol at reflux temperature.

Scheme IV

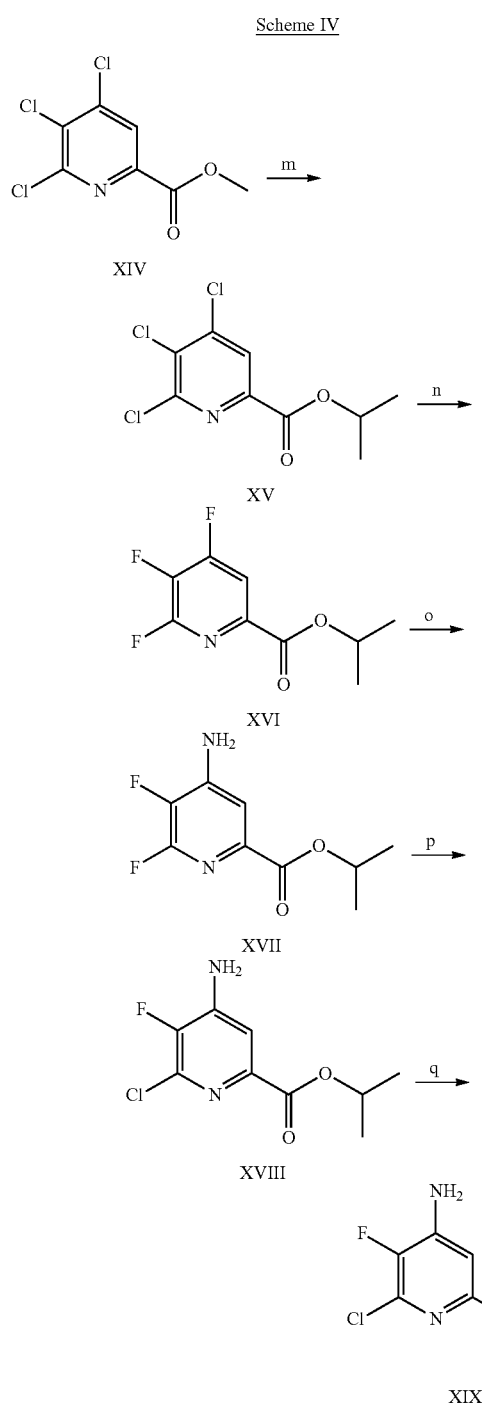

converted to the 3-methoxy-4-amino-5-fluoro-6-chloropicolinate of Formula I-G using standard esterification conditions, such as by treatment with hydrogen chloride (gas) and methyl alcohol at 50° C. In step $f_4$ of Scheme V, Suzuki coupling of the 3-methoxy-4-amino-5-fluoro-6-chloropicolinate of Formula I-G with a boronic acid or ester, in the presence of a catalyst such as bis(triphenylphosphine)-palladium(II) dichloride, potassium fluoride and a polar protic solvent mixture such as acetonitrile-water at 110° C. in a microwave oven, provides the 6-arylpicolinate of Formula I-H, wherein Ar is as previously defined. In step u of Scheme V, Stille coupling of the 3-methoxy-4-amino-5-fluoro-6-chloropicolinate of Formula I-G with a stannane, such as tributyl(vinyl)stannane, in the presence of a catalyst such as bis(triphenylphosphine)-palladium(II) dichloride, in a non-reactive solvent such as 1,2-dichloroethane at 120° C. in a microwave reactor, provides a 6-(substituted)picolinate of Formula I-I, wherein Y is alkyl, cycloalkyl, alkenyl, haloalkenyl and halocycloalkyl.

Scheme V

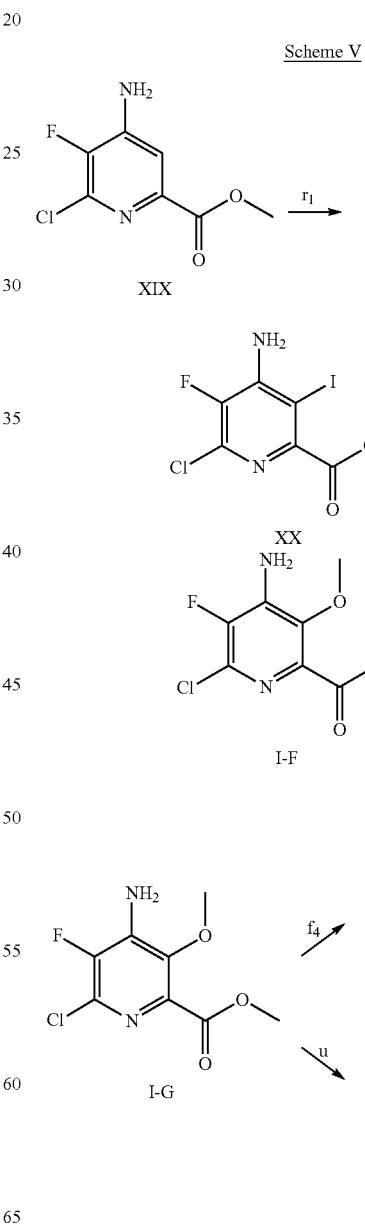

In step $r_1$ of Scheme V, the 4-amino-5-fluoro-6-chloropicolinate of Formula XIX can be transformed into the 3-iodo-4-amino-5-fluoro-6-chloropicolinate of Formula XX via reaction with iodinating reagents such as periodic acid and iodine in a polar, protic solvent such as methyl alcohol at reflux temperature. The 3-iodo-4-amino-5-fluoro-6-chloropicolinate of Formula XX can be treated with cesium carbonate and a catalytic amount of both copper(I) iodide and 1,10-phenanthroline in the presence of a polar, protic solvent such as methyl alcohol at 65° C. to provide a 3-methoxy-4-amino-5-fluoro-6-chloropicolinic acid of Formula I-F, as in step $s_1$ of Scheme V. The resulting picolinic acid of Formula I-F can be In step $f_5$ of Scheme VI, Suzuki coupling of the 3-methoxy-4-amino-5-fluoro-6-chloropicolinate of Formula XIX, with a boronic acid or ester, in the presence of a catalyst such as bis(triphenylphosphine)palladium(II) dichloride, potassium fluoride and a polar protic solvent mixture such as acetonitrile-water at 115° C. in a microwave reactor, provides a 6-arylpicolinate of Formula XXI, wherein Ar is as previously defined. In step $r_2$ of Scheme VI, the 6-arylpicolinate of Formula XXI can be transformed into the 3-iodo-6-arylpicolinate of Formula XXII via reaction with iodinating reagents such as periodic acid and iodine in a polar, protic solvent such as methyl alcohol at reflux temperature. The 3-iodo-6-arylpicolinate of Formula XXII can be treated with cesium carbonate and a catalytic amount of both copper(I) iodide and 1,10-phenanthroline in the presence of a polar, protic solvent such as methyl alcohol at 70° C. to provide a 3-methoxy-6-arylpicolinic acid of Formula I-J, as in step $s_2$ of Scheme VI.

Scheme VI

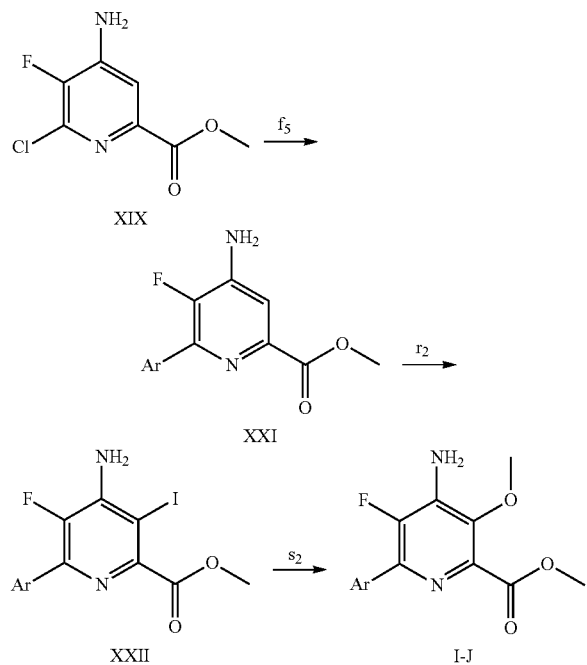

In step $v_1$ of Scheme VII, a 3-iodo-4-amino-5-fluoro-6-arylpicolinate of Formula XXII can be coupled with tributylmethylthiostannane, using a palladium catalyst such as his (triphenylphosphine) palladium (II) chloride in a polar solvent such as dimethylformamide at 100° C. to provide 3-methylthio-4-amino-5-fluoro-6-arylpicolinates of Formula XXIII, wherein Ar is as previously defined. Alternately, in step $v_2$ of Scheme VII, the 3-iodo-4-amino-5-fluoro-6-chloropicolinate of Formula XX, can be coupled with tributylmethylthiostannane, using a palladium catalyst such as his (triphenylphosphine) palladium (II) chloride in a polar solvent such as dimethylformamide at 100° C., to provide the 3-methylthio-4-amino-5-fluoro-6-chloro picolinate of Formula XXIV. In step $f_6$ of Scheme VII, compounds of Formula XXIV can be reacted with a boronic acid or ester, in the presence of a catalyst such as bis(triphenylphosphine)palladium(II) dichloride, potassium fluoride and a polar protic solvent mixture such as acetonitrile-water at 115° C. in a microwave reactor to provide compounds of Formula XXIII.

Scheme VII

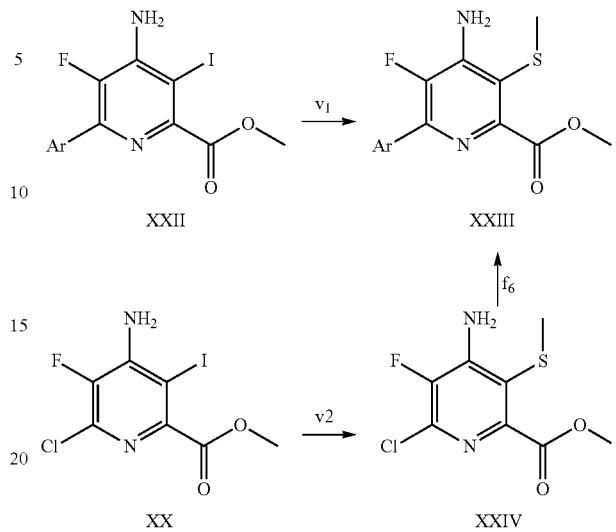

In step $w_1$ of Scheme VIII, the known methyl 4-amino-6-bromo-3-methoxypicolinate of Formula VIII (prepared as described in Fields, S. C. et al. WO 2001051468) can be converted to the 6-vinylpicolinate of Formula XXV via a Stille coupling using vinyltributyltin and a palladium catalyst such as bis(triphenylphosphine)palladium (II) dichloride in a solvent like dichloroethane. In step $x_1$, the amino group can be protected as a bis(tert-butyl carbamate) group in the 6-vinylpicolinate of Formula XXVI in the presence of a catalytic amount of 4-(dimethylamino)pyridine in a solvent like dichloroethane. In step y, the vinyl group can be converted to an aldehyde group via ozonolyzis in a solvent such as dichloromethane and in the presence of a reducing agent like triphenylphosphine to afford the 6-formylpicolinate of Formula XXVII. In step z, the 6-(difluoromethyl)picolinate of Formula XXVIII can be prepared by a one-pot, two step reaction sequence using first bis(2-methoxyethyl)aminosulfur trifluoride (deoxo-fluor) to convert the aldehyde group to the difluoromethyl group in a solvent like dichloromethane, followed by deprotection of the carbamate groups using trifluoro acetic acid.

Scheme VIII

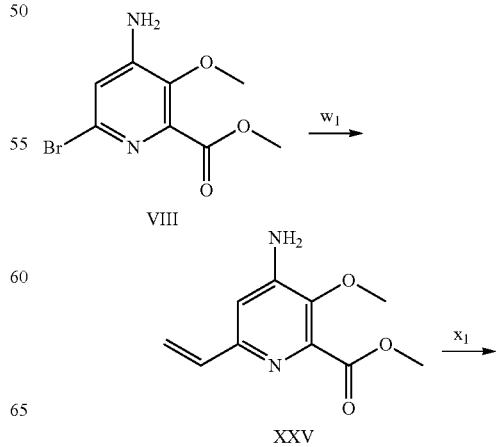

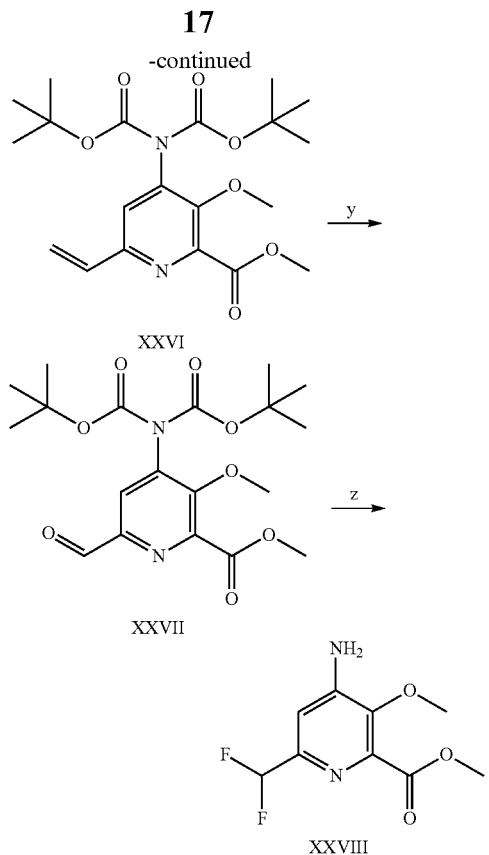

In step w₂ of Scheme IX, methyl 4-amino-6-bromo-3-methoxypicolinate of Formula VIII can be converted to the 6-(1-ethoxyvinyl)picolinate of Formula XXIX via a Stille coupling using (1-ethoxyvinyl)tributyltin and a palladium catalyst such as bis(triphenylphosphine)palladium (II) dichloride in a solvent like dichloroethane. In step aa, the 6-acetylpicolinate of Formula XXX can be prepared by treatment of the 6-(1-ethoxyvinyl)picolinate of Formula XXIX with a 2 N aqueous solution of hydrochloric acid in a solvent like tetrahydrofuran. In step bb, the ketone group can be reduced to the alcohol group in the (1-hydroxyethyl)picolinate of Formula XXXI, by using a reducing agent like sodium borohydride in a solvent like methanol. In step cc, the fluoro group in the 6-(1-fluoroethyl)picolinate of Formula XXXII can be introduced using deoxo-fluor in a solvent like dichoromethane. The 6-(1-fluoroethyl)picolinic acid of Formula XXXIII can be obtained by deesterification of the methyl ester group, as in step dd, using a 2 N aqueous solution of sodium hydroxide in a mixture of solvent like tetrahydrofuran and methanol. In step x₂, the amino group can be protected as a bis(tert-butyl carbamate) group in the 6-acetylpicolinate of Formula XXXIV in the presence of a catalytic amount of 4-(dimethylamino)pyridine in a solvent like dichloroethane. In step ee, the 6-(1,1-difluoroethyl)picolinate of Formula XXXV can be prepared by a one-pot, two step reaction sequence using first deoxo-fluor to convert the methyl ketone group to the difluoroethyl group in a solvent like dichloromethane, followed by deprotection of the carbamate groups using trifluoro acetic acid. The acid can be formed as in step dd.

Scheme IX

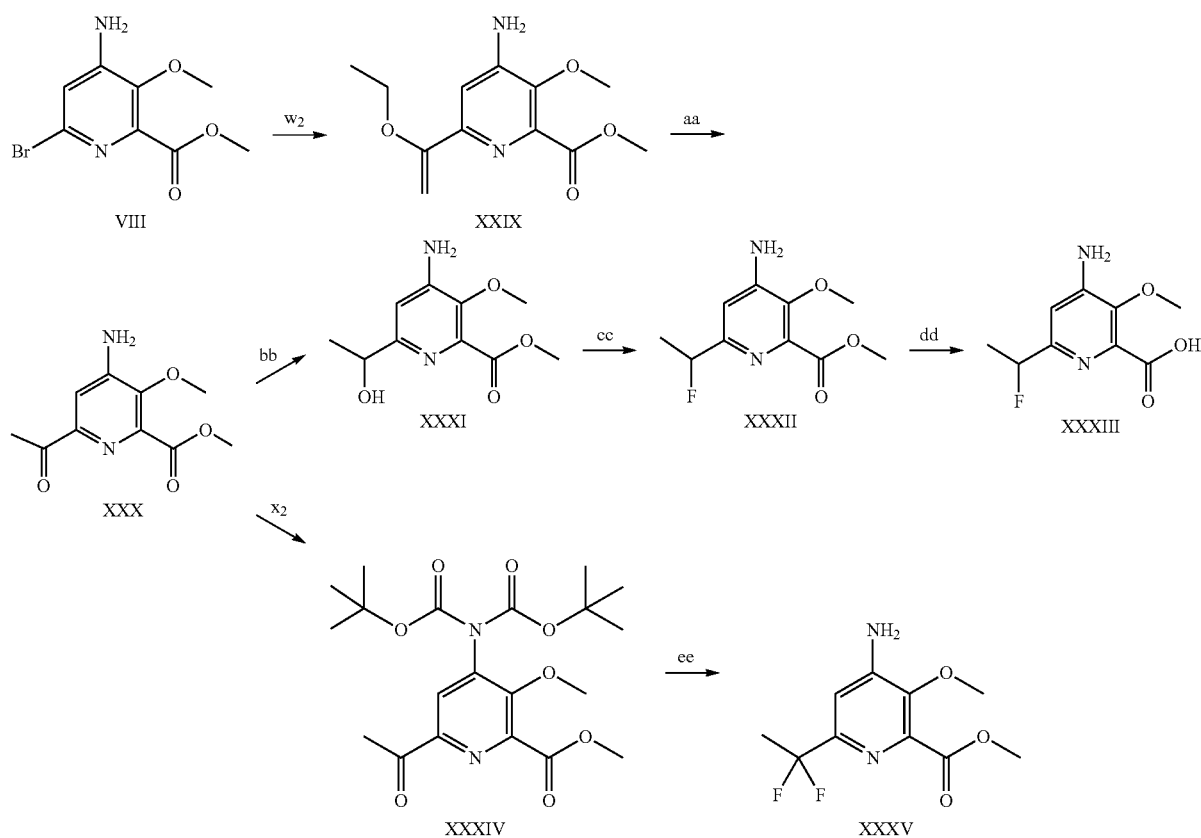

In step ff of Scheme X, the compound of Formula XXXVI, where Ar is as previously defined, X is chloro or bromo and R$_{11}$ is an acid derivative (synthesized as in Renga, J. M. et al. U.S. Patent applications 20100311981 and 20100311594), can be transformed via reaction with an alkoxy, haloalkoxy, alkylthio, haloalkylthio neat or in a polar aprotic solvent such as THF or DMSO to afford the compound of Formula XXXVII, wherein Ar and R$_{11}$ are as previously defined, and Q is alkoxy, haloalkoxy, alkylthio, haloalkylthio.

Scheme X

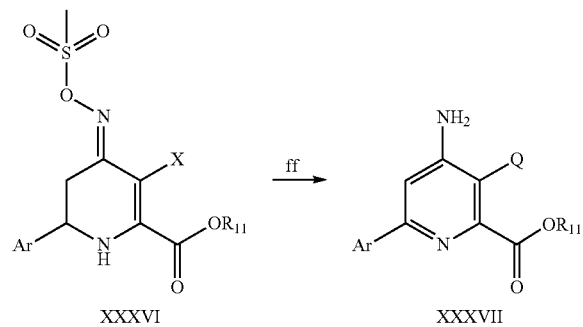

XXXVI → XXXVII

In step gg of Scheme XI, the compound of Formula XXXVI can be converted to a compound of Formula XXXVIII using reagents such as methylamine or dimethylamine, depending on the level of substitution desired.

Scheme XI

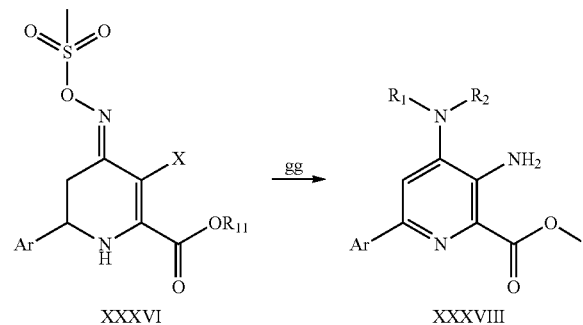

XXXVI → XXXVIII

In step hh of Scheme XII, compounds of Formula XXXVI can be converted to a mixture of picolinate regioisomers of Formula XXXIX and XXXX (XXXIX/XXXX 4:1) via addition of 2,2,2-trifluoroethanethiol in the presence of a base like potassium carbonate.

Scheme XII

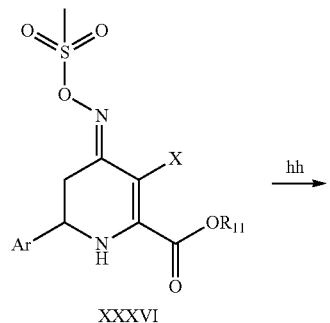

XXXVI

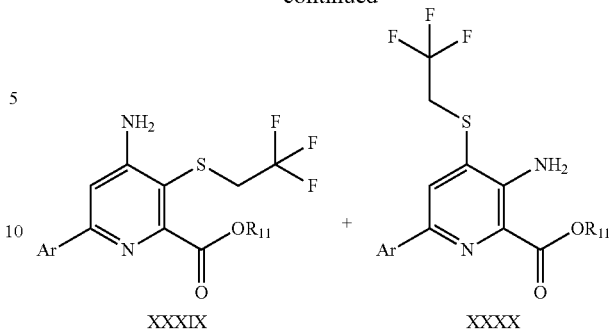

XXXIX + XXXX

The compounds of described herein, obtained by any of these processes, can be recovered by conventional means. Typically, the reaction mixture is acidified with an aqueous acid, such as hydrochloric acid, and extracted with an organic solvent, such as ethyl acetate or dichloromethane. The organic solvent and other volatiles can be removed by distillation or evaporation to obtain the desired compound of Formula A, which can be purified by standard procedures, such as by recrystallization or chromatography.

The compounds described herein have been found to be useful as pre-emergence and post-emergence herbicides. They can be employed at non-selective (higher) rates of application to control a broad spectrum of the vegetation in an area or at lower rates of application for the selective control of undesirable vegetation. Areas of application include pasture and rangelands, roadsides and rights-of-way, power lines and any industrial areas where control of undesirable vegetation is desirable. Another use is the control of unwanted vegetation in crops such as corn, rice and cereals. They can also be used to control undesirable vegetation in tree crops such as citrus, apple, rubber, oil palm, forestry and others. It is usually preferred to employ the compounds post-emergence. It is further usually preferred to use the compounds to control a wide spectrum of woody plants, broadleaf and grass weeds, and sedges.

Use of the compounds to control undesirable vegetation in established crops is especially indicated. While each of the compounds encompassed by Formula A is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings, above and below ground plant parts such as shoots, roots, tubers, rhizomes and the like, and established vegetation.

Herbicidal activity is exhibited by the compounds of the present invention when they are applied directly to the plant or to the locus of the plant, to the soil, or to the flood or irrigation water at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, the water quality, and the like, as well as the amount of chemical applied. These and other factors can be adjusted as is known in the art to promote non-selective or selective herbicidal action. Generally, it is preferred to apply the compounds of described herein post-emergence to relatively immature undesirable vegetation to achieve the maximum control of weeds.

Application rates of about 1 to about 4,000 grams/hectare (g/ha) are generally employed in post-emergence operations; for pre-emergence applications, rates of about 1 to about 4,000 g/ha are generally employed. The higher rates designated generally give non-selective control of a broad variety of undesirable vegetation. The lower rates typically give selective control and can be employed in the locus of crops.

The herbicidal compounds of the present invention are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides or applied sequentially with the other herbicide or herbicides. Some of the herbicides that can be employed in conjunction with the compounds of the present invention include: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlomitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmediphan, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate and xylachlor.

The compounds of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifenethyl, mefenpyr-diethyl, MG 191, MON 4660, naphthalic anhydride (NA), oxabetrinil, R29148 and N-phenylsulfonylbenzoic acid amides, to enhance their selectivity.

The compounds of the present invention can additionally be employed to control undesirable vegetation in many crops that have been made tolerant to or resistant to them or to other herbicides by genetic manipulation or by mutation and selection. The herbicidal compounds of the present invention can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix. Similarly, the herbicidal compounds of the present invention can be used in conjunction with acetolactate synthase inhibitors on acetolactate synthase inhibitor tolerant crops or 4-hydroxyphenyl-pyruvate-dioxygenase inhibitors on hydroxyphenyl-pyruvate-dioxygenase tolerant crops.

While it is possible to utilize the compounds described herein, e.g., 3-alkoxy, thioalkyl and amino-4-amino-6-(substituted)picolinate compounds of Formula A directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds described herein or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions. They can also be provided as a pre-mix or tank mixed.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethylhexyl stearate, n-butyl oleate, isopropyl myristate, propylene glycol dioleate, di-octyl succinate, di-butyl adipate, di-octyl phthalate and the like; esters of mono-, di- and poly-carboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers, and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in *McCutcheon's Detergents and Emulsifiers Annual*, MC Publishing Corp., Ridgewood, N.J., 1998, and in *Encyclopedia of Surfactants*, Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono- and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

Oftentimes, some of these materials, such as vegetable or seed oils and their esters, can be used interchangeably as an agricultural adjuvant, as a liquid carrier or as a surface active agent.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation or flood water, and by other conventional means known to those skilled in the art.

The following Examples are presented to illustrate the various aspects of this invention and should not be construed as limitations to the claims.

EXAMPLES

General Considerations: Fluorine spectra were acquired at 376 MHz on a Bruker DRX400 spectrometer. The spectra were referenced to trichlorofluoromethane (CFCl$_3$) as an external standard and were typically conducted with proton decoupling.

Example 1

Preparation of (4-bromo-2-fluorophenyl)trimethylsilane

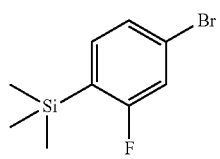

A solution of n-butyllithium (n-BuLi, 2.5 Molar (M) in hexanes; 900 microliters (μL), 2.2 millimoles (mmol), 1.1 equivalents (equiv)) was added to a stirred solution of 1,4-dibromo-2-fluorobenzene (500 milligrams (mg), 2.0 mmol, 1.0 equiv) in diethyl ether (Et$_2$O; 10 milliliters (mL)) at −78° C. The resulting pale yellow solution was stirred at −78° C. for 2 hours (h). Chlorotrimethylsilane (TMSCl; 300 μL, 2.4 mmol, 1.2 equiv) was added, and the resulting pale yellow solution was allowed to slowly warm to 23° C., by allowing the dry ice/acetone bath to melt, and was stirred for 72 h. The reaction mixture was diluted with water (H$_2$O; 50 mL) and was extracted with dichloromethane (CH$_2$Cl$_2$; 3×50 mL). The combined organic layers were dried over magnesium sulfate (MgSO$_4$), gravity filtered, and concentrated by rotary evaporation to afford the title compound as a pale yellow oil (350 mg, 71%): IR (thin film) 3068 (w), 2955 (m), 2927 (m), 2855 (w), 1598 (w), 1567 (w) cm$^{-1}$; $^1$H NMR (400 MHz, DMSO-d$_6$) δ 7.38-7.49 (m, 3H), 0.30 (s, 9H).

Example 2

Preparation of (4-bromo-2,3-difluorophenyl)trimethylsilane

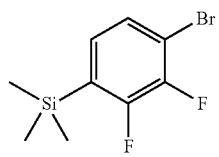

Diisopropylamine (7.86 grams (g), 78 mmol) was dissolved in tetrahydrofuran (THF; 104 mL) and cooled to −75° C. utilizing a dry ice/acetone bath. A solution of n-BuLi (2.5 M in hexanes; 22.80 mL, 57.0 mmol) was added dropwise, and the solution was again cooled to −75° C. 1-Bromo-2,3-difluorobenzene (10 g, 51.8 mmol) was dissolved in THF (25.9 mL), and the solution was added dropwise keeping the temperature below −60° C. The reaction mixture was then allowed to warm to −15° C. before cooling again to −75° C. TMSCl (7.29 mL, 57.0 mmol) was then added dropwise, and the reaction mixture was allowed to warm to 25° C. and then concentrated under vacuum. The residue was partitioned between ethyl acetate (EtOAc) and H$_2$O. The organic phase was washed twice more with H$_2$O and concentrated. Kugelrohr distillation at 88° C. provided the product in greater purity but an impurity was distilling at that temperature. Kugelrohr distillation of that purified distillate at 75° C. led to purer product but some product was left in the pot. This process yielded the title compound as a clear oil (3.0 g, 21.83%, 90% purity): $^1$H NMR (300 MHz, CDCl$_3$) δ 7.28 (ddd, J=7.8, 5.2, 1.3 Hz, 1H), 6.98 (ddd, J=8.0, 4.8, 1.9 Hz, 1H), 0.32 (s, 9H); EIMS m/z 264, 266.

Example 3

Preparation of (4-bromo-2,5-difluorophenyl)trimethylsilane

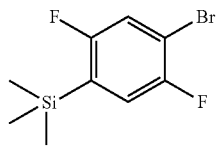

To a solution of 1,4-dibromo-2,5-difluorobenzene (5 g, 18.4 mmol) in anhydrous Et$_2$O (60 mL) at −78° C. (dry ice/acetone bath) was added n-BuLi (7.72 mL, 19.31 mmol) dropwise. The reaction mixture was stirred at −78° C. for 30 minutes (min) (light yellow color), then TMSCl (2.59 mL, 20.23 mmol) was added. The reaction mixture was allowed to slowly warm to 20° C. and was stirred for 12 h. The reaction mixture was poured into a saturated (satd) aqueous (aq) ammonium chloride solution (NH$_4$Cl; 150 mL), and the crude product was extracted with Et$_2$O (3×). The combined organic layers were washed with satd aq NaCl, dried over MgSO$_4$, filtered and concentrated (orange/brown oil). The residue was purified by column chromatography (silica gel (SiO$_2$), eluting with hexanes) to afford the title compound as a colorless oil (4.17 g, 86%): $^1$H NMR (400 MHz, CDCl$_3$) δ 7.20 (dd, J=7.1, 5.1 Hz, 1H), 7.09 (dd, J=8.0, 4.4 Hz, 1H), 0.31 (d, J=0.9 Hz, 9H); $^{19}$F NMR (376 MHz, CDCl$_3$) δ −105.42, −115.48; EIMS m/z 266.

Example 4

Preparation of (2-fluoro-4-(4,4,5,5-tetramethyl-1,3, 2-dioxaborolan-2-yl)-phenyl)trimethylsilane

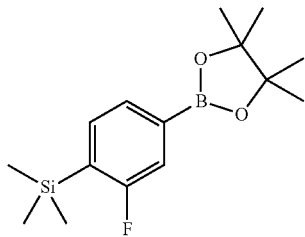

A solution of n-BuLi (2.5 M in hexanes; 8.5 mL, 21 mmol, 1.1 equiv) was added to a stirred solution of (4-bromo-2-fluorophenyl)trimethylsilane (4.8 g, 19 mmol, 1.0 equiv) in THF (80 mL) at −78° C. The resulting orange solution was stirred at −78° C. for 15 min. 2-Isopropoxy-4,4,5,5-tetramethyl-1,3,2-dioxaborolane (4.4 mL, 21 mmol, 1.1 equiv) was added, and the cloudy orange solution was allowed to slowly warm to 23° C., by allowing the dry ice/acetone bath to melt, and was stirred for 20 h. The reaction mixture was diluted with H$_2$O (200 mL), adjusted to approximately pH=4 using 1 M hydrochloric acid (HCl), and extracted with CH$_2$Cl$_2$ (3×100 mL). The combined organic layers were dried (MgSO$_4$), gravity filtered, and concentrated by rotary evaporation to afford the crude product, (2-fluoro-4-(4,4,5,5-tetramethyl-1,3,2-dioxaborolan-2-yl)phenyl)trimethylsilane, as a pale yellow semisolid (6.0 g, 99% crude yield): $^1$H NMR (400 MHz, CDCl$_3$) δ 7.55 (dt, J=7.5, 1 Hz, 1H), 7.38-7.42 (m, 2H), 1.34 (s, 12H), 0.29 (d, J=1 Hz, 9H).

Example 5

Preparation of (3-fluoro-4-(4,4,5,5-tetramethyl-1,3, 2-dioxaborolan-2-yl)-phenyl)trimethylsilane

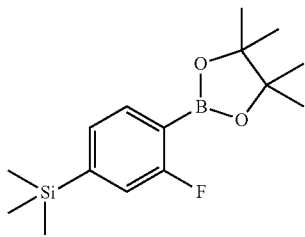

To a −78° C. solution of 1,4-dibromo-2-fluorobenzene (4 g, 15.75 mmol) in THF (52.5 mL) was added a solution of n-BuLi (2.5 M in hexanes; 6.3 mL, 15.75 mmol). The reaction mixture was stirred at −78° C. for 30 min 2-Isopropoxy-4,4, 5,5-tetramethyl-1,3,2-dioxaborolane (3.21 mL, 15.75 mmol) was then added, and the mixture was stirred at −78° C. for an additional 1 h. A solution of n-BuLi (2.5 M in hexanes; 6.3 mL, 15.75 mmol) was then added, followed after 30 min by TMSCl (4.03 mL, 31.5 mmol). The reaction mixture was allowed to warm slowly to room temperature and was stirred overnight. The mixture was then poured into a half saturated NH$_4$Cl solution (300 mL), and the crude product was extracted with Et$_2$O (3×). The combined organic layers were dried over MgSO$_4$, filtered, concentrated and dried in vacuo to afford the title compound as a yellow oil (4.87 g, 11.92 mmol, 76% yield based on a 72% purity): $^1$H NMR (400 MHz, CDCl$_3$) δ 7.71 (dd, J=7.2, 6.0 Hz, 1H), 7.26 (dt, J=7.2, 1.2 Hz, 1H), 7.16 (dd, J=9.6, 0.4 Hz, 1H), 1.36 (s, 12H), 0.26 (s, 9H); $^{19}$F NMR (376 MHz, CDCl$_3$) δ −104.02; EIMS m/z 294.

Example 6

Preparation of (2,3-difluoro-4-(4,4,5,5-tetramethyl-1, 3,2-dioxaborolan-2-yl)phenyl)trimethylsilane

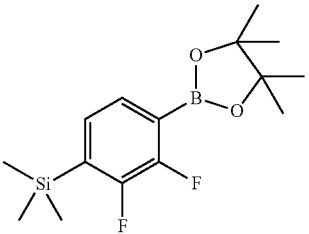

A solution of sec-butyllithium (1.4 M in cyclohexane; 19.17 mL, 26.8 mmol) was added to THF (53.7 mL) cooled to −75° C. To this solution was added (2,3-difluorophenyl)-trimethylsilane (prepared as in Heiss, C. et al. *Eur. J. Org. Chem.* 2007, 4, 669-675; 5.0 g, 26.8 mmol) dropwise keeping the temperature below −70° C. The resulting reaction mixture was stirred at −75° C. for 45 min after which time 2-isopropoxy-4,4,5,5-tetramethyl-1,3,2-dioxaborolane (5.49 g, 29.5 mmol) was added dropwise keeping the temperature below −70° C. The reaction mixture was then allowed to warm to 25° C. and was partitioned between Et$_2$O and H$_2$O. The aqueous phase was acidified to pH 3 with 12 Normal (N) HCl. The product was extracted with Et$_2$O, and the organic phase was dried and concentrated under vacuum to provide the title compound as a white solid (5.03 g, 60%): $^1$H NMR (300 MHz, CDCl$_3$) δ 7.42 (ddd, J=7.3, 4.4, 0.7 Hz, 1H), 7.09 (ddd, J=7.3, 4.1, 0.9 Hz, 1H), 1.36 (s, 12H), 0.32 (d, J=0.9 Hz, 9H); EIMS m/z 312.

Example 7

Preparation of (2,5-difluoro-4-(4,4,5,5-tetramethyl-1, 3,2-dioxaborolan-2-yl)phenyl)trimethylsilane

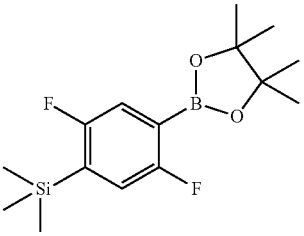

A mixture of (4-bromo-2,5-difluorophenyl)trimethylsilane (10 g, 37.7 mmol), potassium acetate (11.10 g, 113 mmol), 1,1'-bis(diphenylphosphino)ferrocenedichloro palladium(II) dichloromethane complex (2.76 g, 3.77 mmol), and bis(pinacolato)diboron (10.53 g, 41.5 mmol) in dimethyl sulfoxide (DMSO; 126 mL) was stirred at 80° C. for 12 h. The mixture was poured into H$_2$O (600 mL), and the crude product was extracted with Et$_2$O (3×). The combined organic layers were dried over MgSO$_4$, filtered and concentrated to give a black oil. The residue was filtered through a short pad of silica gel and washed with Et$_2$O. After concentration, the title compound was obtained as an orange-brown oil (12.14 g, 31.9 mmol, 85% yield based on an 82% purity), which was used without further purification in the next step: $^1$H NMR (400 MHz, CDCl$_3$) δ 7.30 (dd, J=7.8, 4.1 Hz, 1H), 7.00 (dd, J=8.4, 3.7 Hz, 1H), 1.35 (s, 12H), 0.30 (d, J=0.9 Hz, 9H); $^{19}$F NMR (376 MHz, CDCl$_3$) δ −109.11, −110.92; EIMS m/z 312.

Example 8

Preparation of methyl
4,6-dichloro-3-methoxypicolinate

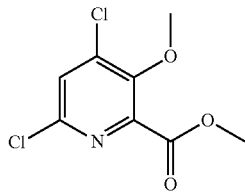

Methyl 6-chloro-3-methoxypicolinate (prepared as in Van Heertum, J. C. et al. U.S. Pat. No. 5,571,775 A, Nov. 5, 1996; 4.0 g, 20 mmol) was dissolved in dry CH$_2$Cl$_2$ (20 mL), treated with urea hydrogen peroxide complex (4.0 g, 43 mmol), cooled to 0-5° C., stirred and treated in portions with trifluoroacetic anhydride (5.6 mL, 40 mmol). The mixture was allowed to warm to 20° C. and stirred for 20 h. An additional portion of the urea hydrogen peroxide complex (2.0 g) and trifluoroacetic anhydride (2.8 mL) were added and stirring was continued for 4 h. The mixture was stirred with 10% sodium bisulfite (NaHSO$_3$) solution until negative to starch-iodide paper. The organic phase was washed with H$_2$O (10 mL), dried (Na$_2$SO$_4$) and evaporated. This material was dissolved in phosphorus oxychloride (POCl$_3$; 30 mL) and heated at 70° C. for 2 h and then at reflux for 3 h to produce a 1:1 mixture of the isomeric 4,5- and 4,6-dichloropicolinates. After cooling, the volatiles were removed under vacuum, the residue was combined with ice and the product was taken up in EtOAc. This solution was washed with H$_2$O, dried (Na$_2$SO$_4$) and evaporated. The crude mixture was purified by reverse-phase high performance liquid chromatography (RP-HPLC; eluting with 60% acetonitrile (CH$_3$CN)—H$_2$O) to provide the title compound (1.1 g, 23%): $^1$H NMR (400 MHz, CDCl$_3$) δ 7.50 (s, 1H), 3.99 (s, 3H), 3.98 (s, 3H); EIMS m/z 235.

Example 9

Preparation of methyl 4-amino-6-chloro-
3-methoxypicolinate (Compound 1)

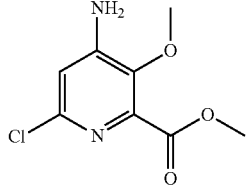

Methyl 4,6-dichloro-3-methoxypicolinate (320 mg, 1.4 mmol) was dissolved in dry N,N-dimethylformamide (DMF; 5 mL), treated with sodium azide (130 mg, 2.0 mmol) and heated at 50° C. for 5 h. After cooling, the mixture was shaken with EtOAc (20 mL) and H$_2$O (10 mL). The organic phase was washed with H$_2$O (2×10 mL) and satd aq NaCl (1×10 mL), dried (Na$_2$SO$_4$) and evaporated. This material was dissolved in methyl alcohol (CH$_3$OH; 15 mL), treated with sodium borohydride (NaBH$_4$; 55 mg, 1.4 mmol) and stirred at 20° C. for 1 h. The mixture was treated with H$_2$O (10 mL), and the volatiles were removed under vacuum. The residue was taken up in EtOAc (25 mL), washed with H$_2$O (10 mL) and satd aq sodium chloride (NaCl; 10 mL), dried (Na$_2$SO$_4$), and evaporated to give the desired product as a white solid (100 mg, 33%): mp 78-79° C.; $^1$H NMR (400 MHz, CDCl$_3$) δ 6.76 (s, 1H), 4.84 (s, 2H), 3.95 (s, 3H), 3.87 (s, 3H); EIMS m/z 216.

Example 10

Preparation of methyl
4-amino-5,6-dichloro-3-methoxypicolinate
(Compound 2)

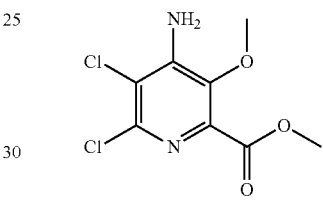

Methyl 4-amino-6-chloro-3-methoxypicolinate (260 mg, 1.2 mmol) was dissolved in dry CH$_3$CN (7 mL), treated with sulfuryl chloride (120 μL, 1.5 mmol) and stirred for 30 min. The solution was stirred with satd aq sodium bicarbonate (NaHCO$_3$; 10 mL) for 20 min and then mixed with EtOAc (20 mL) and satd aq NaCl (10 mL). The aqueous phase was extracted with EtOAc (15 mL), and the combined organic phases were washed with satd aq NaCl (10 mL), dried (Na$_2$SO$_4$) and evaporated to give the title compound as a white solid (240 mg, 80%): mp 119-121° C.; $^1$H NMR (400 MHz, CDCl$_3$) δ 5.04 (s, 2H), 3.97 (s, 3H), 3.93 (s, 3H); EIMS m/z 250.

Example 11

Preparation of methyl 4-acetamido-6-(4-chloro-2-
fluoro-3-methoxyphenyl)-3-hydroxypicolinate

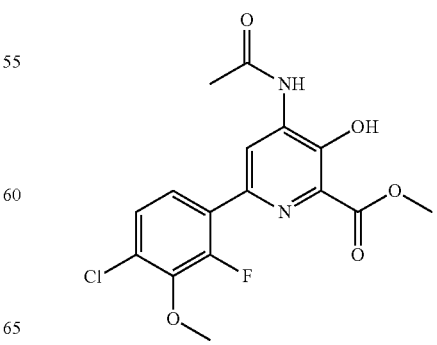

Methyl 4-acetamido-3-(benzyloxy)-6-bromopicolinate (prepared as in Kong, L. C. C. et al. U.S. Patent Application Publication 2005/0176767; 1.5 g, 4.0 mmol), (4-chloro-2-fluoro-3-methoxyphenyl)boronic acid (1.2 g, 5.9 mmol), bis(triphenylphosphine)-palladium(II) dichloride (PdCl$_2$(PPh$_3$)$_2$; 278 mg, 0.4 mmol), cesium fluoride (CsF; 1.2 g, 7.9 mmol), 1,2-dimethoxyethane (DME; 7 mL), and H$_2$O (7 mL) were combined and heated in a Biotage microwave at 100° C. for 15 min. H$_2$O was added to the reaction mixture, and the product was extracted with EtOAc. The combined organic extracts were washed with satd aq NaCl, dried with sodium sulfate (Na$_2$SO$_4$), filtered and concentrated. Flash chromatography (SiO$_2$; 0-45% EtOAc/cyclohexane gradient) afforded methyl 4-acetamido-3-(benzyloxy)-6-(4-chloro-2-fluoro-3-methoxyphenyl)picolinate as a yellow solid: mp 115-120° C.; $^1$H NMR (400 MHz, CDCl$_3$) δ 8.87 (d, J=1.6 Hz, 1H), 7.66 (s, 1H), 7.59 (dd, J=8.5, 7.7 Hz, 1H), 7.45 (s, 5H), 7.24 (dd, J=8.6, 1.7 Hz, 1H), 5.13 (s, 2H), 4.03 (s, 3H), 3.99 (d, J=1.0 Hz, 3H), 1.88 (s, 3H); ESIMS m/z 459 ([M+H]$^+$).

The methyl 4-acetamido-3-(benzyloxy)-6-(4-chloro-2-fluoro-3-methoxyphenyl)-picolinate produced in the first step was dissolved in ethyl alcohol (EtOH; 100 mL), and a catalytic amount of palladium hydroxide (Pd(OH)$_2$) in carbon was added (2 spatula tips). The reaction mixture was stirred under a hydrogen atmosphere for 24 h, and the palladium was removed by filtration. The filtrate was concentrated, and the residue was purified by flash chromatography (SiO$_2$; 0-50% EtOAc/hexane gradient) to provide the title compound as a white solid (0.431 g, 29% yield for the two steps): mp 168-172° C.; $^1$H NMR (400 MHz, CDCl$_3$) δ 11.28 (s, 1H), 8.93 (d, J=1.6 Hz, 1H), 7.98 (s, 1H), 7.49 (dd, J=8.5, 7.6 Hz, 1H), 7.23 (dd, J=8.6, 1.8 Hz, 1H), 4.07 (s, 3H), 3.99 (d, J=1.1 Hz, 3H), 2.30 (s, 3H); ESIMS m/z 369 ([M+H]$^+$).

Methyl 4-acetamido-6-(4-chloro-2-fluorophenyl)-3-hydroxypicolinate

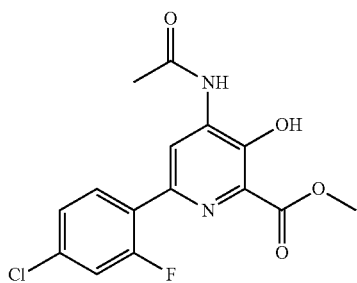 [SMILES: COC(=O)c1nc(-c2ccc(Cl)cc2F)cc(NC(C)=O)c1O]

Using the procedure for Example 11, the title compound was isolated as an off-white solid: mp 201-206° C.; $^1$H NMR (400 MHz, CDCl$_3$) δ 11.27 (s, 1H), 8.95 (d, J=1.5 Hz, 1H), 7.98 (s, 1H), 7.82 (t, J=8.4 Hz, 1H), 7.23 (ddd, J=8.4, 2.0, 0.5 Hz, 1H), 7.18 (dd, J=10.6, 2.0 Hz, 1H), 4.07 (s, 3H), 2.29 (s, 3H); ESIMS m/z 339 ([M+H]$^+$).

Example 12

Preparation of methyl 4-acetamido-6-(4-chloro-2-fluoro-3-methoxyphenyl)-3-methoxypicolinate (Compound 3)

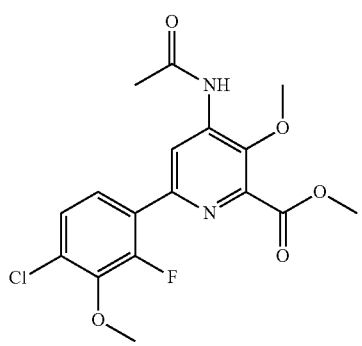 [SMILES: COC(=O)c1nc(-c2ccc(Cl)c(OC)c2F)cc(NC(C)=O)c1OC]

Methyl 4-acetamido-6-(4-chloro-2-fluoro-3-methoxyphenyl)-3-hydroxypicolinate (568 mg, 1.54 mmol), triphenylphosphine (404 mg, 1.54 mmol), diethyl azodicarboxylate (243 μL, 1.54 mmol), and CH$_3$OH (94 μL, 2.31 mmol) were combined in THF and allowed to stir for 24 h. Flash chromatography (SiO$_2$; 0-50% EtOAc/cyclohexane gradient) afforded the title compound as a yellow oil (255 mg, 43%): $^1$H NMR (400 MHz, CDCl$_3$) δ 8.93 (d, J=1.6 Hz, 1H), 8.06 (s, 1H), 7.56 (dd, J=8.5, 7.7 Hz, 1H), 7.23 (dd, J=8.6, 1.7 Hz, 1H), 4.01 (s, 3H), 3.99 (d, J=1.0 Hz, 3H), 3.98 (s, 3H), 2.29 (s, 3H); ESIMS m/z 383 ([M+H]$^+$).

Methyl 4-acetamido-6-(4-chloro-2-fluorophenyl)-3-methoxypicolinate (Compound 4)

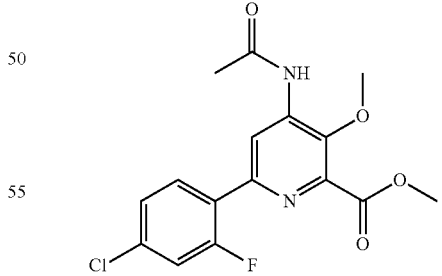

Using the procedure for Example 12, the title compound was isolated as a yellow oil: $^1$H NMR (400 MHz, CDCl$_3$) δ 8.96 (d, J=1.5 Hz, 1H), 7.99 (s, 1H), 7.89 (t, J=8.4 Hz, 1H), 7.23 (ddd, J=8.4, 2.1, 0.6 Hz, 1H), 7.19 (dd, J=10.7, 2.0 Hz, 1H), 4.02 (s, 3H), 3.99 (s, 3H), 2.29 (s, 3H); ESIMS m/z 353 ([M+H]$^+$).

Example 13

Preparation of methyl 4-amino-6-(4-chloro-2-fluoro-3-methoxyphenyl)-3-methoxypicolinate (Compound 5)

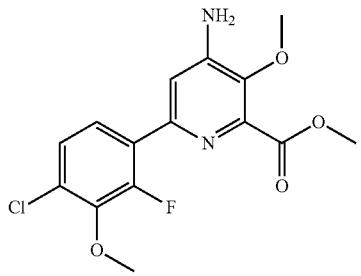 [SMILES: COC(=O)c1nc(-c2ccc(Cl)c(OC)c2F)cc(N)c1OC]

Methyl 4-acetamido-6-(4-chloro-2-fluoro-3-methoxyphenyl)-3-methoxypicolinate (209 mg, 0.55 mmol) was dissolved in CH$_3$OH (10 mL), and acetyl chloride (194 µL, 2.73 mmol) was added dropwise to the mixture. The reaction mixture was allowed to stir at 25° C. for 3 h. Additional acetyl chloride (194 µL, 2.73 mmol) was then added, and the reaction mixture was allowed to stir at 25° C. overnight. The reaction mixture was concentrated to dryness and purified by flash chromatography (SiO$_2$; 0-50% EtOAc/hexane gradient) to provide the title compound as an off-white solid (30 mg, 16%): mp 114-118° C.; $^1$H NMR (400 MHz, CDCl$_3$) δ 7.61 (dd, J=8.5, 7.8 Hz, 1H), 7.22 (dd, J=8.6, 1.8 Hz, 1H), 7.18 (d, J=2.1 Hz, 1H), 4.54 (s, 1H), 3.98 (s, 2H), 3.96 (d, J=0.8 Hz, 2H), 3.92 (s, 2H); ESIMS m/z 341 ([M+H]$^+$), 339 ([M−H]$^−$).

Methyl 4-amino-6-(4-chloro-2-fluorophenyl)-3-methoxypicolinate (Compound 6)

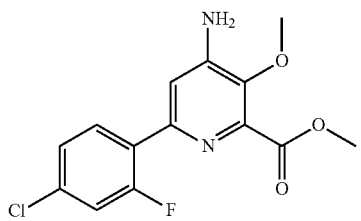

Using the procedure for Example 13, the title compound was isolated as a white solid: mp 139-144° C.; $^1$H NMR (400 MHz, CDCl$_3$) δ 7.96 (t, J=8.5 Hz, 1H), 7.25 (d, J=1.3 Hz, 1H), 7.22 (dd, J=2.0, 0.6 Hz, 1H), 7.15 (dd, J=11.1, 2.0 Hz, 1H), 6.07 (s, 2H), 3.99 (s, 3H), 3.97 (s, 3H); ESIMS m/z 311 ([M+H]$^+$).

Example 14

Preparation of methyl 4-amino-6-(4-chlorophenyl)-3-methoxypicolinate (Compound 7)

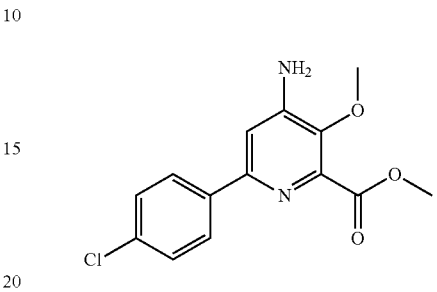

To a solution of methyl 4-amino-6-bromo-3-methoxypicolinate (prepared as in Fields, S. C. et al. U.S. Pat. No. 6,297,197 B1, Oct. 2, 2001; 500 mg, 1.9 mmol) in a 1:1 mixture of DME (4.5 mL) and H$_2$O (4.5 mL) was added 2-(4-chlorophenyl)-1,3,2-dioxaborinane (561 mg, 2.7 mmol), CsF (288 mg, 1.9 mmol) and PdCl$_2$(PPh$_3$)$_2$ (26 mg, 0.1941 mmol). The reaction was heated at 110° C. in a CES microwave for 20 min. The reaction mixture was cooled to ambient temperature and diluted with CH$_2$Cl$_2$, then washed with water, satd aq NaHCO$_3$ and satd aq NaCl. The organic layer was dried with Na$_2$SO$_4$ and filtered. The solvent was removed in vacuo. The residue was purified by normal phase chromatography (eluting with 5% Et$_2$O in CH$_2$Cl$_2$ with 0.05% acetic acid (HOAc)) to afford the title compound as a brown oil (245 mg, 44%): $^1$H NMR (300 MHz, CDCl$_3$) δ 7.90-7.81 (m, 2H), 7.46-7.36 (m, 2H), 7.12 (s, 1H), 4.56 (s, 2H), 4.01 (s, 3H), 3.92 (s, 3H); ESIMS m/z 291 ([M−H]$^−$).

Example 15

Preparation of 4,6-dibromo-2-chloropyridin-3-ol

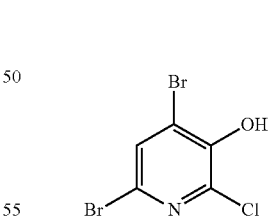

2-Chloropyridin-3-ol (2 g, 15.44 mmol) and N-bromosuccinimide (NBS; 6.05 g, 34.0 mmol) were dissolved in CH$_3$CN (75 mL) and stirred in an aluminum-foil-covered round bottom flask overnight. The reaction mixture was then concentrated under vacuum, and the residue was applied to the top of a silica gel column utilizing CH$_2$Cl$_2$. The product was eluted from the column (5-40% EtOAc/hexanes gradient) to yield the title compound as an oil (4.2 g, 95%): $^1$H NMR (300 MHz, CDCl$_3$) δ 7.60 (s, 1H), 5.85 (s, 1H); ESIMS m/z 286 ([M−H]$^−$).

Example 16

Preparation of 4,6-dibromo-2-chloro-3-(difluoromethoxy)pyridine

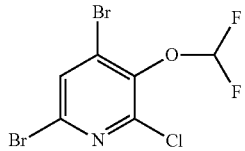 [SMILES: FC(F)Oc1c(Br)cc(Br)nc1Cl]

Potassium carbonate ($K_2CO_3$; 5.01 g, 36.3 mmol) and $H_2O$ (4 mL) were added to a microwave reaction vessel. 4,6-Dibromo-2-chloropyridin-3-ol (0.359 g, 1.25 mmol) was dissolved in $CH_3CN$ (4 mL) and added to the microwave reaction vessel. 2-Chloro-2,2-difluoro-1-phenylethanone (0.953 g, 5.00 mmol) was then added, and the microwave reaction vessel was sealed. The reaction mixture was heated with vigorous stirring with a large stir bar in a Biotage microwave reactor at 100° C. for 4 h. (The reaction mixture is biphasic, and the reaction will not proceed to completion without vigorous stirring.) The reaction mixture was then partitioned between EtOAc and $H_2O$. The organic phase was washed once more with $H_2O$, dried and concentrated. The product was redissolved in $CH_2Cl_2$ and filtered through short plug of silica gel utilizing $CH_2Cl_2$ as the eluting solvent. The eluent was concentrated to provide the title compound as a light yellow low-melting solid (0.325 g, 0.963 mmol, 77%): $^1$H NMR (300 MHz, $CDCl_3$) δ 7.73 (s, 1H), 6.63 (t, J=73.1, 1H); EIMS m/z 337.

Example 17

Preparation of 6-bromo-2-chloro-3-(difluoromethoxy)pyridin-4-amine

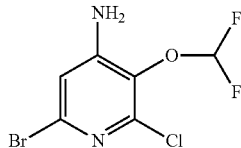 [SMILES: Nc1cc(Br)nc(Cl)c1OC(F)F]

4,6-Dibromo-2-chloro-3-(difluoromethoxy)pyridine (780 mg, 2.312 mmol) was dissolved in DMF (5 mL), and sodium azide (180 mg, 2.77 mmol) was added. The reaction mixture was heated at 65° C. for 2 h and the progress of the reaction was checked by liquid chromatography-mass spectrometry (LC-MS). The reaction appeared to be mostly complete. The product was partitioned between $Et_2O$ and $H_2O$. The aqueous phase was then extracted twice more with $Et_2O$. The organic extracts were combined, diluted with petroleum ether, washed twice with $H_2O$, dried, and concentrated. The product was purified by column chromatography ($SiO_2$, EtOAc/hexane gradient) to yield 4-azido-6-bromo-2-chloro-3-(difluoromethoxy)-pyridine (0.335 g, 48.4%): $^1$H NMR (300 MHz, $CDCl_3$) δ 7.26 (s, 1H), 6.59 (t, J=73.6, 1H).

4-Azido-6-bromo-2-chloro-3-(difluoromethoxy)pyridine (0.563 g, 1.880 mmol) was then dissolved in $CH_3OH$ (15 mL), and $NaBH_4$ (0.107 g, 2.82 mmol) was added. The reaction mixture was stirred at ambient temperature for 15 min at which point thin-layer chromatographic (TLC) analysis indicated complete consumption of starting material. The reaction mixture was concentrated and partitioned between EtOAc and $H_2O$. The organic phase was dried and concentrated. The product was purified by flash chromatography ($SiO_2$, EtOAc/hexane gradient) to yield the title compound as a white solid (0.398 g, 77%): mp 138-140° C.; $^1$H NMR (600 MHz, DMSO-$d_6$) δ 6.98 (t, J=73.1 Hz, 1H), 6.84 (d, J=14.6 Hz, 2H); EIMS m/z 274.

Example 18

Preparation of 2-chloro-6-(4-chloro-2-fluoro-3-methoxyphenyl)-3-(difluoro-methoxy)pyridin-4-amine

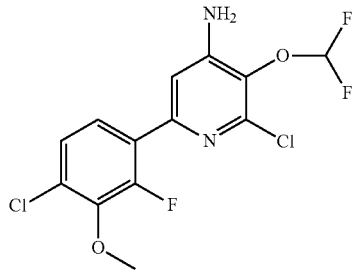 [SMILES: COc1c(Cl)ccc(-c2cc(N)c(OC(F)F)c(Cl)n2)c1F]

6-Bromo-2-chloro-3-(difluoromethoxy)pyridin-4-amine (368 mg, 1.346 mmol), 2-(4-chloro-2-fluoro-3-methoxyphenyl)-1,3,2-dioxaborinane (395 mg, 1.615 mmol), $PdCl_2(PPh_3)_2$ (47.2 mg, 0.067 mmol), and CsF (409 mg, 2.69 mmol) were combined in DME (2 mL) and $H_2O$ (2 mL) and heated in a Biotage microwave reactor at 110° C. for 15 min. The cooled reaction mixture was partitioned between EtOAc and $H_2O$. The organic phase was dried, concentrated onto silica gel, and purified by flash chromatography ($SiO_2$, EtOAc/hexane gradient). This process yielded the title compound as a white solid (0.4 g, 84%): mp 152-154° C.; $^1$H NMR (300 MHz, DMSO-$d_6$) δ 7.63-7.50 (m, 1H), 7.42 (dd, J=8.7, 1.6, 1H), 7.16 (d, J=1.8, 1H), 7.02 (t, J=73.4, 1H), 6.70 (s, 2H), 3.93 (d, J=0.8, 3H); ESIMS m/z 354 ([M+H]$^+$), 352 ([M−H]$^-$).

Example 19

Preparation of ethyl 4-amino-6-(4-chloro-2-fluoro-3-methoxyphenyl)-3-(difluoromethoxy)picolinate (Compound 8)

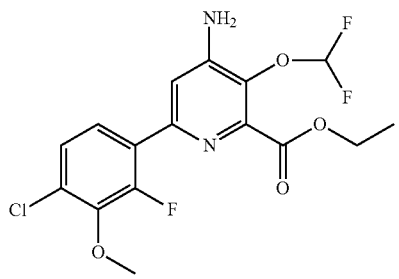 [SMILES: CCOC(=O)c1nc(-c2ccc(Cl)c(OC)c2F)cc(N)c1OC(F)F]

2-Chloro-6-(4-chloro-2-fluoro-3-methoxyphenyl)-3-(difluoromethoxy)pyridin-4-amine (0.2 g, 0.566 mmol), [1,1'-bis (diphenylphosphino)ferrocene]dichloropalladium(II) (($C_{17}H_{14}P)_2$·Fe·PdCl$_2$; 0.041 g, 0.057 mmol), and triethylamine ($Et_3N$, 0.158 mL, 1.133 mmol) were combined in EtOH (5 mL) in a 45 mL bomb reactor. The bomb reactor was pressurized to 400 pounds per square inch (psi) with carbon monoxide (CO) and the reaction was heated at 105° C. for 40 h. The reaction mixture was then filtered through a small plug of silica gel utilizing EtOAc as the eluent. The filtrate was concentrated, and the product was purified by column chromatography (SiO$_2$, hexane/EtOAc gradient) to yield the title compound as a white solid (79 mg, 35.7%): $^1$H NMR (300 MHz, CDCl$_3$) δ 7.66 (dd, J=8.6, 7.7 Hz, 1H), 7.28-7.24 (m, 1H), 7.22 (d, J=1.7 Hz, 1H), 6.72 (t, J=75.1 Hz, 1H), 4.73 (s, 2H), 4.46 (q, J=7.1 Hz, 2H), 3.97 (d, J=0.8 Hz, 3H), 1.42 (t, J=7.2 Hz, 3H); ESIMS m/z 391 ([M+H]$^+$), 389 ([M−H]$^−$); $^{19}$F NMR (376 MHz, CDCl$_3$) δ −79.74, −132.19.

Compound 9 in Table 1 was synthesized as in Example 19.

Example 20

Preparation of propan-2-yl 4,5,6-trichloropicolinate

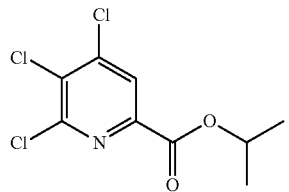

Methyl 4,5,6-trichloropicolinate (prepared as in Balko, T. W. et al. U.S. Pat. No. 6,784,137 B2, Aug. 31, 2004; 14.19 g, 59.0 mmol) was slurried in 2-propanol (150 mL) in a 250 mL round bottom flask equipped with a Dean-Stark trap and a reflux condenser. Sulfuric acid (98% H$_2$SO$_4$; 8.07 g, 82 mmol) was added, and the reaction mixture was heated to reflux. After 20 h at reflux, the majority of the 2-propanol (100 mL) was distilled overhead. The remaining reaction mixture solidified upon cooling to room temperature. The resulting solid was stirred with EtOAc (500 mL) and satd aq NaHCO$_3$ (500 mL). The organic layer was separated, washed with satd aq NaCl, and then filtered through Celite. The organic extract was concentrated to 150 mL by rotary evaporation. Hexane (100 mL) was added, and the solution was stored at −20° C. overnight. Crystals were collected, washed with hexane and dried in air (7.58 g, mp 104.6-105.7° C.). A second crop was obtained by concentration of the filtrate to give a total of 10.36 g (65%): $^1$H NMR (400 MHz, DMSO-d$_6$) δ 8.23 (s, 1H, pyridine H), 5.16 (septet, J=6.3 Hz, 1H, CHMe$_2$), 1.34 (d, J=6.3 Hz, 6H, CHMe$_2$); $^{13}$C{$^1$H} NMR (101 MHz, CDCl$_3$) δ 161.9 (CO$_2$R), 150.6, 145.9, 145.0, 133.1, 125.4 (C3), 70.7 (CHMe$_2$), 21.7 (Me). Anal. Calcd for C$_9$H$_8$Cl$_3$NO$_2$: C, 40.26; H, 3.00; N, 5.22. Found: C, 40.25; H, 3.02; N, 5.22.

Example 21

Preparation of propan-2-yl 4,5,6-trifluoropicolinate

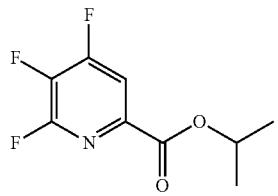

A 250 mL three-neck flask was equipped with a mechanical stirrer, a Dean-Stark trap with nitrogen inlet, and a thermocouple. The flask was purged with nitrogen and CsF (23.38 g, 154 mmol) was added. Anhydrous DMSO (124 mL) was added and the suspension was evacuated/backfilled (5×) with nitrogen. The suspension was heated at 80° C. for 30 min. DMSO (20 mL) was distilled off under vacuum at 75° C. to remove any residual water. Propan-2-yl 4,5,6-trichloropicolinate (13.45 g, 50.1 mmol) was added against a nitrogen purge. The reaction mixture was evacuated/backfilled (3×) and heated at 100° C. for 1 h with vigorous stirring.

A second 250 mL three-neck flask was equipped with a mechanical stirrer, a Dean-Stark trap with nitrogen inlet, and a thermocouple. The flask was purged with nitrogen and CsF (24.41 g, 0.160 mmol) was added. Anhydrous DMSO (30 mL) was added, and the suspension was evacuated/backfilled (5×) with nitrogen. The suspension was heated to 80° C. for 30 min DMSO (22 mL) was distilled off under vacuum at 75° C. to remove residual water. The cooled reaction mixture in the first flask was cannula filtered into the second flask under nitrogen. The reaction mixture was evacuated/backfilled (5×) and then heated at 100° C. for 1 h and then for an additional 90 min at 110° C. Analysis of an aliquot by gas chromatography (GC) showed 96% propan-2-yl 4,5,6-trifluoropicolinate with only 1.4% propan-2-yl 5-chloro-4,6-difluoropicolinate present. The crude product solution was used directly in the amination step without further purification. Alternatively, the product can be isolated by aqueous workup, extraction with EtOAc, and drying to give a light tan oil: $^1$H NMR (400 MHz, CDCl$_3$) δ 7.94 (dd, J$_{F−H}$=4.5, 8.7 Hz, 1H, H3), 5.30 (septet, J$_{H−H}$=6.3 Hz, 1H, CHMe$_2$), 1.44 (d, J$_{H−H}$=6.3 Hz, 6H, CHMe$_2$); $^{13}$C{$^1$H} NMR (101 MHz, CDCl$_3$) δ 161.2 (s, CO$_2$iPr), 157.3 (ddd, J$_{F−C}$=266, 8, 6 Hz, C4/C6), 152.2 (ddd, J$_{F−C}$=241, 12, 5 Hz, C4/C6), 141.1 (dt, J$_{F−C}$=14, 7 Hz, C2), 137.0 (ddd, J$_{F−C}$=270, 31, 13 Hz, C5), 113.8 (dd, J$_{F−C}$=17, 4 Hz, C3), 70.4 (s, CHMe$_2$), 21.33 (s, Me); $^{19}$F NMR (376 MHz, CDCl$_3$) δ −74.29 (dd, J$_{F−F}$=24, 22 Hz, F6), −112.67 (ddd, J$_{F−F}$=22, 19, J$_{F−H}$=8.3 Hz, F4), −151.58 (ddd, J$_{F−F}$=24, 19, J$_{F−H}$=4.7 Hz, F5).

Example 22

Preparation of propan-2-yl 4-amino-5,6-trifluoropicolinate

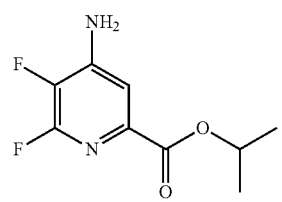

The reaction mixture from Example 21 was filtered to remove Cs salts, and the salts were washed with DMSO (50 mL). The DMSO washing solution was added to the DMSO solution (150 mL) which had been saturated with ammonia (NH$_3$) for 15 min. The flask was kept in a cold bath which kept the temperature near 16° C. NH$_3$ was bubbled through the reaction mixture for 30 min, during which time a white precipitate formed. After 90 min, analysis of an aliquot by GC showed a single major peak for the 4-amino product. The reaction mixture was quenched by addition of satd aq NH$_4$Cl (100 mL), followed by H$_2$O (400 mL). The aqueous solution was extracted into Et$_2$O (3×150 mL) and then EtOAc (3×150 mL). The combined organic extracts were washed with H$_2$O (5×150 mL) and then satd aq NaCl. The extracts were dried (MgSO$_4$) and evaporated to a tan solid, which was washed with 1:1 hexane-Et$_2$O to give a light tan powder (5.57 g, 51.4% overall): mp 168-170° C.; $^1$H NMR (400 MHz, CDCl₃) δ 7.42 (d, $J_{F-H}$=5.5 Hz, 1H, pyridine H), 5.22 (septet, J=6.2 Hz, 1H, CHMe₂), 4.75 (s, 2H, NH₂), 1.35 (d, J=6.2 Hz, 6H, CHMe₂); ¹³C{¹H} NMR (101 MHz, DMSO-d₆) δ 162.8 (CO₂R), 151.2 (dd, $J_{F-C}$=228, 12 Hz, C6), 146.5 (dd, $J_{F-C}$=9, 6 Hz, C2/C4), 139.3 (dd, $J_{F-C}$=16, 5 Hz, C2/C4), 133.8 (dd, $J_{F-C}$=252, 31 Hz, C5), 112.3 (C3), 68.8 (CHMe₂), 21.5 (Me); ¹⁹F NMR (376 MHz, DMSO-d₆) δ −91.9 (d, $J_{F-F}$=26.6 Hz, F6), −163.9 (dd, $J_{F-F}$=26.6, $J_{H-F}$=5.6 Hz, F5). Anal. Calcd for C₉H₁₀F₂N₂O₂: C, 50.00; H, 4.66; N, 12.96. Found: C, 49.96; H, 4.65; N, 12.91.

Example 23

Preparation of propan-2-yl 4-amino-6-chloro-5-fluoropicolinate

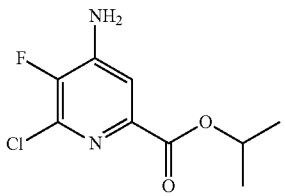

Propan-2-yl 4-amino-5,6-difluoropicolinate (4.25 g, 19.7 mmol) was dissolved in HCl (4 M in dioxane; 65 mL) in a 100 mL Hastalloy stirred Parr reactor. The reactor was heated at 100° C. for 2 h. Upon standing at room temperature overnight, a yellow crystalline solid formed. This solid was not soluble in EtOAc but did dissolve upon shaking with satd aq NaHCO₃ (500 mL) and EtOAc (300 mL). The aqueous layer was extracted with EtOAc (2×250 mL). The combined organic extracts were washed with H₂O (5×50 mL) and then with satd aq NaCl. The extracts were dried (MgSO₄) and concentrated under vacuum to provide an off-white solid. The crude product was purified by column chromatography (120 g silica column; 0-100% hexane-EtOAc gradient) to give a white solid (2.11 g, 46%): mp 190.7-192.4° C.; ¹H NMR (400 MHz, DMSO-d₆) δ 7.543 (d, $J_{F-H}$=5.7 Hz, 1H), 6.91 (br s, 2H, NH₂), 5.09 (septet, J=6 Hz, 1H, CHMe₂), 1.29 (d, J=6 Hz, 6H, CHMe₂); ¹³C{¹H}NMR (101 MHz, DMSO-d₆) δ 162.8 (CO₂R), 144.8 (d, $J_{F-C}$=12 Hz, C2/C4), 143.4 (d, $J_{F-C}$=254 Hz, C5), 142.7 (d, $J_{F-C}$=4.8 Hz, C2/C4), 136.5 (d, $J_{F-C}$=17 Hz, C6), 112.8 (d, $J_{F-C}$=5 Hz, C3), 68.9 (CHMe₂), 21.6 (Me); ¹⁹F NMR (376 MHz, DMSO-d₆) δ −141.0 (d, $J_{F-H}$=6 Hz). Anal. Calcd for C₉H₁₀ClFN₂O₂: C, 46.47; H, 4.33; N, 13.75. Found: C, 46.50; H, 4.33; N, 11.96.

Example 24

Preparation of methyl 4-amino-6-chloro-5-fluoropicolinate

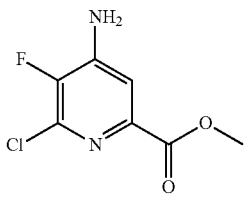

Isopropyl 4-amino-6-chloro-5-fluoropicolinate (1.35 g, 5.80 mmol) was dissolved in anhydrous CH₃OH (50 mL), treated with titanium(IV) isopropoxide (300 mg, 2.2 mmol), and heated at reflux for 4 h. After cooling, the volatiles were removed under vacuum, and the residue was taken up in EtOAc (30 mL). This solution was stirred with H₂O (1 mL) for 20 min and then filtered through diatomaceous earth. The filtrate was washed with satd aq NaCl (10 mL), dried (Na₂SO₄), and evaporated to give the title compound (1.2 g, 97%): mp 180-183° C.; ¹H NMR (400 MHz, DMSO-d₆) δ 7.45 (d, J=6.0 Hz, 1H), 6.93 (s, 2H), 3.83 (s, 3H); ¹⁹F NMR (376 MHz, DMSO-d₆) δ −131.36, −131.42, −135.47, −135.53; EIMS m/z 204.

Another method of producing this intermediate is as follows:

To a solution of 4-amino-6-chloro-5-fluoropicolinic acid (23.8 g, 125 mmol) in MeOH (400 ml), cooled in an ice water bath, thionyl chloride (11.78 ml, 162 mmol) was added. The reaction mixture was heated to an internal temperature of 50° C., for 8 hours. The reaction mixture was then diluted with H₂O, and extracted with EtOAC (3×100 mL). The combined organics were washed with Sat. NaCl, dried over Mg Sulfate, filtered and concentrated under vacuum to give methyl 4-amino-6-chloro-5-fluoropicolinate (21.9 g, 107 mmol, 86% yield).

Example 25

Preparation of methyl 4-amino-6-chloro-5-fluoro-3-iodopicolinate

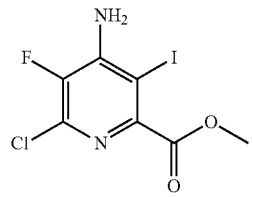

Methyl 4-amino-6-chloro-5-fluoropicolinate (2.2 g, 10.8 mmol) was dissolved in methyl alcohol (20 mL). The solution was treated with periodic acid (880 mg, 3.9 mmol) and iodine (2.2 g, 8.6 mmol) and then heated at reflux for 20 h. The mixture was cooled, and the volatiles were removed under vacuum. The residue was dissolved in EtOAc (50 mL) and then stirred with 10% NaHSO₃ solution (20 mL) for 10 min. The organic phase was separated and washed with satd aq NaCl (10 mL), dried (Na₂SO₄) and evaporated. The residue was purified by silica gel chromatography (5-50% EtOAc-hexane gradient) to give the title compound as a light orange solid (2.5 g, 70%): mp 149-151° C.; ESIMS m/z 330 ([M]⁺); ¹H NMR (400 MHz, CDCl₃) δ 5.17 (s, 2H, NH₂), 3.97 (s, 3H, OMe); ¹⁹F NMR (376 MHz, CDCl₃) δ −135.79 (s).

Example 26

Preparation of methyl 4-amino-6-chloro-5-fluoro-3-methoxypicolinate (Compound 10)

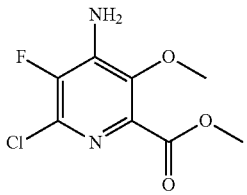

To a dry 1 liter (L) flask was added methyl 4-amino-6-chloro-5-fluoro-3-iodopicolinate (50 g, 151 mmol) and cesium carbonate ($Cs_2CO_3$; 99 g, 303 mmol). $CH_3OH$ (378 mL) was added, and the solution was sparged with nitrogen for 10 min. 1,10-Phenanthroline (6.00 g, 30.3 mmol) and copper(I) iodide (CuI; 2.88 g, 15.13 mmol) were added, and the flask was fitted with a reflux condenser and heated to 65° C. under nitrogen. After 12 h, CuI (2.88 g, 15.13 mmol) was again added to the reaction mixture, and heating was continued until consumption of the iodopicolinate was observed. The reaction mixture was cooled to room temperature, filtered through Celite, and concentrated in vacuo. To the crude residue was added EtOAc (100 mL) and $H_2O$ (100 mL). The layers were separated, and the aqueous phase was acidified to pH=2 with concentrated (conc) HCl and subsequently extracted with EtOAc (3×100 mL). The organic extracts were combined, washed with satd aq NaCl, dried ($Na_2SO_4$), filtered, and concentrated in vacuo to afford 4-amino-6-chloro-5-fluoro-3-methoxypicolinic acid.

The crude acid was treated with $CH_3OH$ (200 mL) saturated with hydrogen chloride (HCl; g), and the reaction mixture was heated at 50° C. for 4 h. Upon consumption of the acid, the mixture was cooled to room temperature and concentrated in vacuo. The residue was dissolved in $Et_2O$ (100 mL) and washed with $H_2O$ (50 mL) and satd aq NaCl (50 mL). The organic extracts were combined, dried ($Na_2SO_4$), filtered, and concentrated in vacuo. The crude ester was purified using a Teledyne ISCO purification system with a gradient eluent system of EtOAc and hexanes, followed by recrystallization from water to provide the title compound as a purple solid (10.1 g, 36% overall yield for the two steps): $^1H$ NMR (400 MHz, $CDCl_3$) δ 4.67 (s, 2H), 3.96 (s, 3H), 3.93 (s, 3H); $^{19}F$ NMR (376 MHz, $CDCl_3$) δ −135.15 (s); EIMS m/z 234.

Example 27

Preparation of methyl 4-amino-5-fluoro-6-(3-fluoro-4-(trifluoromethyl)-phenyl)picolinate

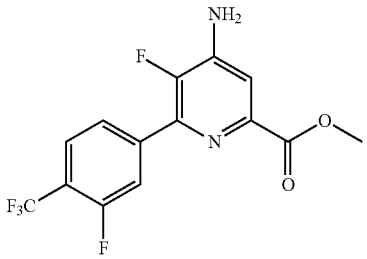 [SMILES: COC(=O)c1cc(N)c(F)c(-c2ccc(C(F)(F)F)c(F)c2)n1]

To a 5 mL microwave vial was added methyl 4-amino-6-chloro-5-fluoropicolinate (500 mg, 2.44 mmol), 2-(3-fluoro-4-(trifluoromethyl)phenyl)-4,4,5,5-tetramethyl-1,3,2-dioxaborolane (851 mg, 2.93 mmol), potassium fluoride (KF; 369 mg, 6.35 mmol), and $PdCl_2(PPh_3)_2$ (172 mg, 0.24 mmol). Subsequently, $CH_3CN$ (3.0 mL) and $H_2O$ (3.0 mL) were added, and the reaction vial was sealed and heated in a Biotage microwave at 115° C. for 20 min. The reaction mixture was cooled to room temperature and diluted with EtOAc (5 mL). The layers were separated and the aqueous phase was extracted with EtOAc (2×2 mL). The organic extracts were combined, dried ($Na_2SO_4$), filtered, and concentrated in vacuo. The crude product was purified using a Teledyne ISCO purification system with a gradient eluent system of EtOAc and hexanes to yield the title compound as a yellow solid (570 mg, 70%): $^1H$ NMR (400 MHz, DMSO-$d_6$) δ 7.94 (dt, J=12.3, 6.2 Hz, 3H), 7.52 (d, J=6.4 Hz, 1H), 6.80 (s, 2H), 3.86 (s, 3H); $^{19}F$ NMR (376 MHz, DMSO-$d_6$) δ −59.96, −59.99, −115.69, −144.18, −144.20; ESIMS m/z 333.21 ([M+H]$^+$).

Methyl 4-amino-6-(4-chlorophenyl)-5-fluoropicolinate

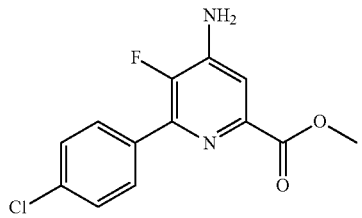 [SMILES: COC(=O)c1cc(N)c(F)c(-c2ccc(Cl)cc2)n1]

Using the procedure for Example 27, the title compound was isolated as an off-white solid: $^1H$ NMR (400 MHz, DMSO-$d_6$) δ 7.88 (d, J=7.4 Hz, 2H), 7.58 (d, J=8.6 Hz, 2H), 7.47 (d, J=6.3 Hz, 1H), 6.67 (s, 2H), 3.84 (s, 3H); $^{19}F$ NMR (376 MHz, DMSO-$d_6$) δ −145.01; ESIMS m/z 281.48 ([M+H]$^+$), 279.85 ([M−H]$^−$).

Example 28

Preparation of methyl 4-amino-5-fluoro-6-(3-fluoro-4-(trifluoromethyl)phenyl)-3-iodopicolinate

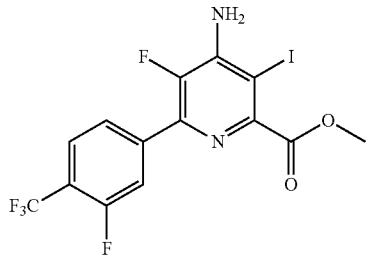 [SMILES: COC(=O)c1nc(-c2ccc(C(F)(F)F)c(F)c2)c(F)c(N)c1I]

Methyl 4-amino-5-fluoro-6-(3-fluoro-4-(trifluoromethyl)phenyl)picolinate (500 mg, 1.51 mmol) was dissolved in $CH_3OH$ (0.6 mL) in a round bottom flask. Periodic acid (123 mg, 0.542 mmol) and iodine (306 mg, 1.204 mmol) were added, and the reaction mixture was heated at reflux with a drying tube for 12 h. The reaction mixture was cooled to room temperature and concentrated in vacuo. The crude product was dissolved in $Et_2O$ and washed with 10% sodium thiosulfate ($Na_2S_2O_3$; 2×5 mL). The organic extracts were combined, dried over anhydrous $Na_2SO_4$, filtered, and concentrated providing methyl 4-amino-5-fluoro-6-(3-fluoro-4-(trifluoromethyl)phenyl)-3-iodopicolinate (635 mg, 92%): $^1H$ NMR (400 MHz, DMSO-$d_6$) δ 7.93 (dd, J=14.8, 6.8 Hz, 1H), 7.90-7.82 (m, 2H), 6.89 (s, 2H), 3.88 (s, 3H); $^{19}$F NMR (376 MHz, DMSO-d$_6$) δ −60.02 (t, J=12.4 Hz), −115.50 (td, J=12.2, 7.6 Hz), −139.91 (s); ESIMS m/z 459.62 ([M+H]$^+$).

Methyl 4-amino-6-(4-chlorophenyl)-5-fluoro-3-iodopicolinate

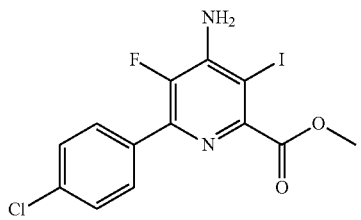 [SMILES: COC(=O)c1nc(-c2ccc(Cl)cc2)c(F)c(N)c1I]

Using the procedure for Example 28, the title compound was isolated as a red semi-solid: $^1$H NMR (400 MHz, DMSO-d$_6$) δ 7.85 (dd, J=8.5, 1.1 Hz, 2H), 7.57 (d, J=8.7 Hz, 2H), 6.75 (s, 2H), 3.87 (s, 3H); $^{19}$F NMR (376 MHz, DMSO-d$_6$) δ −140.67; ESIMS m/z 407.69 ([M+H]$^+$).

Methyl 4-amino-6-(4-chloro-3-fluorophenyl)-5-fluoro-3-iodopicolinate (Compound 91)

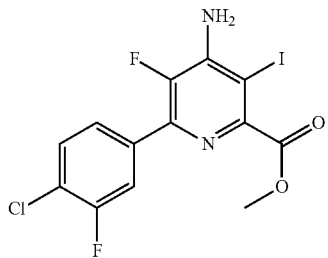 [SMILES: COC(=O)c1nc(-c2ccc(Cl)c(F)c2)c(F)c(N)c1I]

Using the procedure for Example 28, the title compound was isolated as a pale pink solid: $^1$H NMR (400 MHz, CDCl$_3$) δ 7.77-7.84 (m, 1H), 7.68-7.77 (m, 2H), 6.80 (s, 2H), 3.88 (s, 3H). $^{19}$F NMR (376 MHz, DMSO-d6) δ −140.15, −115.85. ESIMS m/z 425 ([M+H]$^+$), 423 ([M−H]$^-$).

Example 29

Preparation of 4-amino-5-fluoro-6-(3-fluoro-4-(trifluoromethyl)phenyl)-3-methoxypicolinic acid (Compound 11)

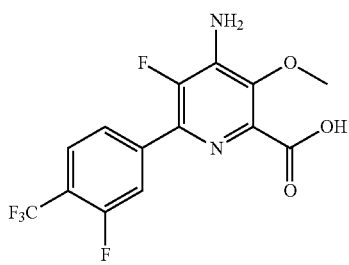 [SMILES: COc1c(C(=O)O)nc(-c2ccc(C(F)(F)F)c(F)c2)c(F)c1N]

Methyl 4-amino-5-fluoro-3-iodopicolinate (0.2 g, 0.437 mmol), Cs$_2$CO$_3$ (0.284 g, 0.873 mmol), 1,10-phenanthroline (17 mg, 0.087 mmol) and CuI (8.3 mg, 0.044 mmol) were added to a dry round bottom flask under nitrogen. CH$_3$OH (4.4 mL) was added, and the reaction was heated at 70° C. until complete consumption of the iodopicolinate. The reaction mixture was cooled to room temperature, filtered through Celite, and concentrated in vacuo. The crude residue was acidified with 2 M HCl and extracted with EtOAc (3×5 mL). The organic extracts were combined, dried (Na$_2$SO$_4$), filtered, and concentrated in vacuo to provide the title compound (0.126 g, 80%) as a red semi-solid: $^1$H NMR (400 MHz, CDCl$_3$) δ 7.83-7.63 (m, 4H), 4.89 (s, 2H), 4.08 (s, 3H); $^{19}$F NMR (376 MHz, DMSO-d$_6$) δ −59.91, −59.93, −59.94, −115.72, −115.75, −140.39; ESIMS m/z 347.81 ([M−H]$^-$).

Example 30

Preparation of methyl 4-amino-5-fluoro-3-methoxy-6-vinylpicolinate (Compound 12)

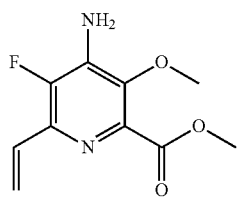

A mixture of methyl 4-amino-6-chloro-5-fluoro-3-methoxypicolinate (405 mg, 1.73 mmol), tributyl(vinyl)stannane (1.097 g, 3.46 mmol), and PdCl$_2$(PPh$_3$)$_2$ (181 mg, 0.26 mmol) in 1,2-dichloroethane (3.5 mL) was heated at 120° C. in a Biotage microwave for 30 min Column chromatography (0-40% EtOAc/hexanes) of the crude reaction mixture provided the title compound as a yellow oil (0.38 g, 97%): $^1$H NMR (400 MHz, CDCl$_3$) δ 6.88 (ddd, J=17.5, 11.1, 1.4 Hz, 1H), 6.33 (dd, J=17.5, 1.6 Hz, 1H), 5.57 (ddd, J=11.1, 1.6, 0.7 Hz, 1H), 4.47 (s, 2H), 3.97 (s, 3H), 3.91 (s, 3H); $^{19}$F NMR (376 MHz, CDCl$_3$) δ −143.2; ESIMS m/z 227 ([M+H]$^+$).

Example 31

Preparation of methyl 4-amino-6-ethyl-5-fluoro-3-methoxypicolinate (Compound 13)

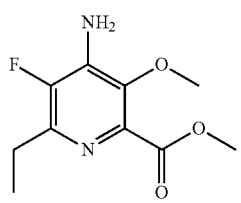

To methyl 4-amino-5-fluoro-3-methoxy-6-vinylpicolinate (0.32 g, 1.42 mmol) in EtOAc (5 mL) was added 10% palladium on carbon (Pd/C, 0.16 g, 0.15 mmol). The mixture was stirred under an atmosphere of hydrogen overnight, filtered through Celite and concentrated to provide methyl 4-amino-6-ethyl-5-fluoro-3-methoxypicolinate (0.21 g, 0.92 mmol) as a white solid: mp 110.5-113.0° C.; $^1$H NMR (400 MHz, CDCl$_3$) δ 4.41 (s, 2H), 3.96 (s, 3H), 3.90 (s, 3H), 2.81 (qd, J=7.6, 2.7 Hz, 2H), 1.26 (t, J=7.6 Hz, 3H); $^{13}$C NMR (101 MHz, CDCl$_3$) δ 165.2, 148.6, 146.2, 144.2, 136.8, 136.1, 61.5, 52.7, 25.3, 12.9; $^{19}$F NMR (376 MHz, CDCl$_3$) δ −142.6; EIMS m/z 228.

Example 32

Preparation of methyl 4-amino-5-fluoro-6-(3-fluoro-4-(trimethylsilyl)phenyl)-3-methoxypicolinate (Compound 14)

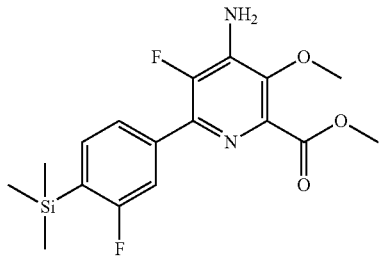

To a 5-mL microwave safe vial were added methyl 4-amino-6-chloro-5-fluoro-3-methoxypicolinate (0.400 g, 1.705 mmol), (2-fluoro-4-(4,4,5,5-tetramethyl-1,3,2-dioxaborolan-2-yl)phenyl)trimethylsilane (0.690 g, 2.344 mmol), KF (0.297 g, 5.11 mmol), and PdCl$_2$(PPh$_3$)$_2$ (0.120 g, 0.170 mmol). A mixture of H$_2$O (1 mL) and CH$_3$CN (2 mL) was added, and the reaction vial was capped and placed in a Biotage Initiator microwave reactor for 20 min at 115° C. with external infrared (IR)-sensor temperature monitoring from the side of the vessel. Upon cooling to room temperature, the reaction mixture was diluted with CH$_2$Cl$_2$ (25 mL) and H$_2$O (25 mL), and the organic layer was filtered through a cotton plug. An additional extraction using EtOAc (25 mL) was combined with the CH$_2$Cl$_2$ and dried over Na$_2$SO$_4$ (50 g). Following filtration of the combined organics through a cotton plug and concentration on a rotary evaporator, the residue was purified using a Teledyne ISCO purification system with a gradient eluent system of CH$_2$Cl$_2$ and EtOAc to yield the title compound as a light pink oil (333 mg, 53%): $^1$H NMR (400 MHz, CDCl$_3$) δ 7.66 (d, J=7.6 Hz, 1H), 7.55 (d, J=9.8 Hz, 1H), 7.46 (dd, J=7.6, 5.9 Hz, 1H), 4.57 (s, 2H), 3.98 (s, 3H), 3.96 (s, 3H), 0.33 (s, 9H); $^{19}$F NMR (376 MHz, CDCl$_3$) δ −100.72, −140.12; ESIMS m/z 367 ([M+H]$^+$).

Example 33

Preparation of methyl 4-amino-6-(2,3-difluoro-4-(trimethylsilyl)phenyl)-5-fluoro-3-methoxypicolinate (Compound 15)

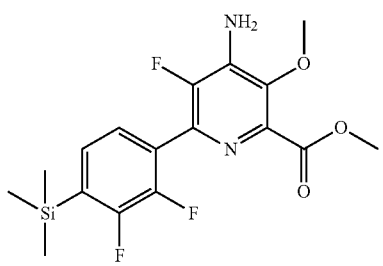

To a 20 mL microwave vial were added methyl 4-amino-6-chloro-5-fluoro-3-methoxypicolinate (0.80 g, 3.41 mmol), (2,3-difluoro-4-(4,4,5,5-tetramethyl-1,3,2-dioxaborolane-2-yl)phenyl)trimethylsilane (1.28 g, 4.09 mmol), sodium carbonate (Na$_2$CO$_3$; 0.36 g, 3.41 mmol), and PdCl$_2$(PPh$_3$)$_2$ (0.24 g, 0.34 mmol). Subsequently, CH$_3$CN (5.7 mL) and H$_2$O (5.7 mL) were added, and the reaction vial was sealed and heated in a Biotage microwave to 115° C. for 20 min. The reaction mixture was cooled to room temperature and diluted with EtOAc (10 mL). The organic layer was separated and the aqueous phase was extracted with EtOAc (2×2 mL). The organic extracts were combined, dried over Na$_2$SO$_4$, filtered, and concentrated in vacuo. The crude product was purified using a Teledyne ISCO purification system with a gradient eluent system of EtOAc and hexanes to yield methyl 4-amino-6-(2,3-difluoro-4-(trimethylsilyl)phenyl)-5-fluoro-3-methoxypicolinate (0.99 g, 75%) as a white solid: mp 123-125° C.; $^1$H NMR (400 MHz, CDCl$_3$) δ 7.32 (ddd, J=7.6, 5.5, 1.1 Hz, 1H), 7.20 (ddd, J=7.7, 4.5, 1.4 Hz, 1H), 4.60 (s, 2H), 3.98 (s, 3H), 3.96 (s, 3H), 0.41-0.28 (m, 9H); $^{19}$F NMR (376 MHz, CDCl$_3$) δ −127.39, −127.45, −127.46, −137.48, −137.56, −140.78, −140.85, −140.86, −140.92; ESIMS m/z 383.20 ([M−H]$^−$).

Methyl 4-amino-5-fluoro-3-methoxy-6-(4-(trimethylsilyl)phenyl)picolinate (Compound 16)

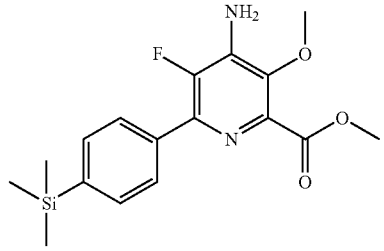

Using the procedure for Example 33, the title compound was isolated as a red solid: $^1$H NMR (400 MHz, DMSO-d$_6$) δ 7.80-7.70 (m, 2H), 7.63 (d, J=8.2 Hz, 2H), 6.49 (s, 2H), 3.85 (s, 3H), 3.77 (s, 3H); $^{19}$F NMR (376 MHz, DMSO-d$_6$) δ −141.15; ESIMS m/z 349.59 ([M+H]$^+$).

Example 34

Preparation of methyl 4-amino-6-(2,5-difluoro-4-(trimethylsilyl)phenyl)-5-fluoro-3-methoxypicolinate (Compound 17)

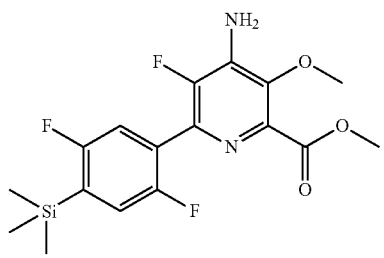

(2,5-Difluoro-4-(4,4,5,5-tetramethyl-1,3,2-dioxaborolan-2-yl)phenyl)trimethylsilane (1.785 g, 4.69 mmol, 82% purity), methyl 4-amino-6-chloro-5-fluoro-3-methoxypicolinate (1 g, 4.26 mmol), Na₂CO₃ (0.542 g, 5.11 mmol), and PdCl₂(PPh₃)₂ (0.299 g, 0.426 mmol) were suspended in a 3:1 mixture of CH₃CN (7.99 mL) and H₂O (2.66 mL) in a microwave vial. The reaction mixture was irradiated at 90° C. for 20 min. The reaction was monitored by TLC and ultra performance liquid chromatography (HPLC). The mixture was poured into a half satd aq NaCl solution and extracted with EtOAc (3×). The combined organic layers were dried over Na₂SO₄, filtered and concentrated. The residue was purified by flash chromatography (SiO₂, ISCO, 120 g column, hexanes/EtOAc gradient) to afford the title compound as a yellow solid (0.977 g, 60%): mp 137-139° C.; ¹H NMR (400 MHz, CDCl₃) δ 7.23 (dd, J=7.9, 5.1 Hz, 1H), 7.12 (dd, J=9.3, 4.0 Hz, 1H), 4.60 (s, 2H), 3.97 (s, 3H), 3.97 (s, 3H), 0.33 (d, J=0.8 Hz, 9H); ¹⁹F NMR (376 MHz, CDCl₃) δ –107.12, –121.88, –137.27; ESIMS m/z 384 ([M]⁺).

Methyl 4-amino-5-fluoro-6-(2-fluoro-4-(trimethylsilyl)phenyl)-3-methoxypicolinate (Compound 18)

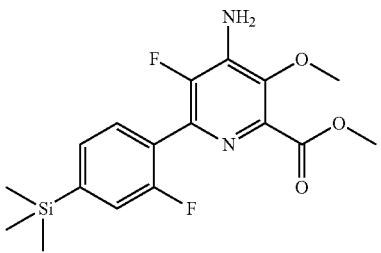

Using the procedure for Example 34, the title compound was isolated as a yellow solid: mp 127-129° C.; ¹H NMR (400 MHz, CDCl₃) δ 7.56 (t, J=7.2 Hz, 1H), 7.37 (dd, J=7.5, 0.7 Hz, 1H), 7.26 (dd, J=10.1, 0.8 Hz, 1H), 4.57 (s, 2H), 3.97 (s, 3H), 3.96 (s, 3H), 0.28 (s, 9H); ¹⁹F NMR (376 MHz, CDCl₃) δ –116.17, –137.36; ESIMS m/z 367 ([M+H]⁺).

Example 35

Preparation of methyl 4-amino-6-(4-bromo-2,3-difluorophenyl)-5-fluoro-3-methoxypicolinate (Compound 19)

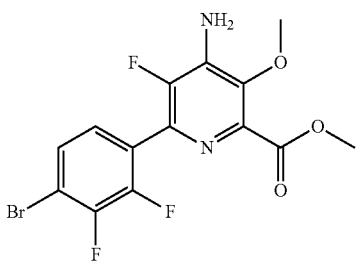

Methyl 4-amino-5-fluoro-3-methoxy-6-(4-(trimethylsilyl)phenyl)picolinate (300 mg, 0.78 mmol) was dissolved in CH₃CN (3.9 mL) and then bromine (0.402 mL, 7.8 mmol) was added. The reaction mixture was stirred at room temperature for 12 h. The mixture was partitioned between CH₂Cl₂ (2 mL) and H₂O (1 mL), and 10% Na₂S₂O₃ (2 mL) was added. The layers were separated, and the aqueous phase was further extracted with CH₂Cl₂ (3×2 mL). The combined organic extracts were dried over Na₂SO₄ and concentrated in vacuo. The product was purified using a Teledyne ISCO purification system with a gradient eluent system of EtOAc and hexanes to yield the title compound as a white solid (123 mg, 40%): ¹H NMR (400 MHz, DMSO-d₆) δ 7.67 (ddd, J=8.3, 6.3, 1.7 Hz, 1H), 7.40-7.27 (m, 1H), 6.68 (s, 2H), 3.84 (s, 3H), 3.79 (s, 3H); ¹⁹F NMR (376 MHz, DMSO-d₆) δ –131.44, –131.45, –131.46, –131.50, –131.50, –131.51, –131.52, –136.12, –136.14, –136.19, –136.20, –136.22, –136.26, –136.28, –138.65, –138.72; ESIMS m/z 392.06 ([M+H]⁺).

Compounds 20-22 in Table 1 were synthesized as in Example 35.

Example 36

Preparation of methyl 4-amino-5-fluoro-6-(4-iodophenyl)-3-methoxypicolinate (Compound 23)

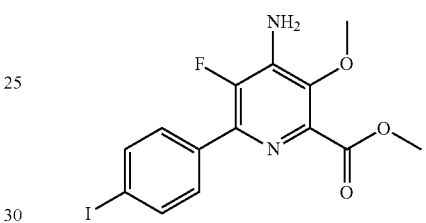

Methyl 4-amino-5-fluoro-3-methoxy-6-(4-(trimethylsilyl)phenyl)picolinate (239 mg, 0.686 mmol) was dissolved in 1,2-dichloroethane (3.4 mL) and iodine monochloride (78 μL, 1.557 mmol). The reaction mixture was stirred at room temperature for 48 h. The mixture was quenched with 10% Na₂S₂O₃ (2 mL) and stirred at room temperature for 1 h. The mixture was extracted with CH₂Cl₂ (3×5 mL), and the combined organic extracts were dried over Na₂SO₄ and concentrated in vacuo. The product was purified via RP-HPLC (CH₃CN/H₂O) to yield the title compound as an orange solid (270 mg, 98%): ¹H NMR (400 MHz, DMSO-d₆) δ 7.86 (d, J=8.5 Hz, 2H), 7.65-7.53 (m, 2H), 6.54 (s, 2H), 3.86 (s, 3H), 3.77 (s, 3H); ¹⁹F NMR (376 MHz, DMSO-d₆) δ –140.64; ESIMS m/z 403.61 ([M+H]⁺).

Compounds 24-28 in Table 1 and methyl 4-amino-6-(4-chloro-2,3-difluorophenyl)-5-fluoro-3-methoxypicolinate were synthesized as in Example 36.

Example 37

Preparation of methyl 4-amino-5-fluoro-6-(4-formylphenyl)-3-methoxypicolinate (Compound 29)

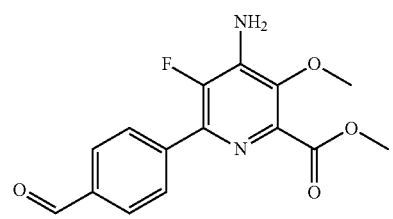 [SMILES: COC(=O)c1nc(-c2ccc(C=O)cc2)c(F)c(N)c1OC]

To a 5-mL microwave safe vial was added methyl 4-amino-6-chloro-5-fluoro-3-methoxypicolinate (0.400 g, 1.705 mmol), 4-(4,4,5,5-tetramethyl-1,3,2-dioxaborolan-2-yl)benzaldehyde (0.435 g, 1.875 mmol), KF (0.297 g, 5.11 mmol), and PdCl$_2$(PPh$_3$)$_2$ (0.120 g, 0.170 mmol). A mixture of H$_2$O (1 mL) and CH$_3$CN (2 mL) was added, and the reaction vial was capped and placed in a Biotage Initiator microwave reactor for 20 min at 115° C. with external IR-sensor temperature monitoring from the side of the vessel. Upon cooling to room temperature, the reaction mixture was diluted with CH$_2$Cl$_2$ (25 mL) and H$_2$O (25 mL), and the organic layer was filtered through a cotton plug. An additional extraction using EtOAc (25 mL) was combined with the CH$_2$Cl$_2$ and dried over Na$_2$SO$_4$ (50 g). Following filtration of the combined organics through a cotton plug and concentration on a rotary evaporator, the residue was purified using a Teledyne ISCO purification system with a gradient eluent system of CH$_2$Cl$_2$ and EtOAc to yield the title compound as a tan solid (335 mg, 65%): $^1$H NMR (400 MHz, CDCl$_3$) δ 10.08 (s, 1H), 8.09 (dd, J=8.3, 1.5 Hz, 2H), 8.03-7.93 (m, 2H), 4.62 (s, 2H), 4.00 (s, 3H), 3.98 (s, 3H); $^{19}$F NMR (376 MHz, CDCl$_3$) δ −139.69; ESIMS m/z 305 ([M+H]$^+$), 303 ([M−H]$^−$).

Example 38

Preparation of methyl 4-amino-6-(4-ethynylphenyl)-5-fluoro-3-methoxypicolinate (Compound 30)

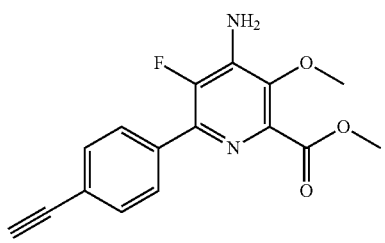 [SMILES: C#Cc1ccc(-c2nc(C(=O)OC)c(OC)c(N)c2F)cc1]

To a 20 mL reaction vial were added methyl 4-amino-5-fluoro-6-(4-formylphenyl)-3-methoxypicolinate (0.41 g, 1.347 mmol), K$_2$CO$_3$ (0.372 g, 2.69 mmol), and CH$_3$OH (20 mL). Dimethyl 1-diazo-2-oxopropylphosphonate (0.311 g, 1.617 mmol) was added in one portion. After stirring for 4 h, the reaction mixture was diluted with Et$_2$O (50 mL) and washed with 5% NaHCO$_3$ (25 mL). The organic layer was dried over MgSO$_4$ (5 g), filtered, and concentrated on a rotary evaporator. The resulting residue was purified using a Teledyne ISCO purification system with a gradient eluent system of CH$_2$Cl$_2$ and EtOAc to yield the title compound as an off-white solid (297 mg, 73%): $^1$H NMR (400 MHz, CDCl$_3$) δ 7.93-7.85 (m, 2H), 7.62-7.53 (m, 2H), 4.57 (s, 2H), 3.98 (s, 3H), 3.96 (s, 3H), 3.15 (s, 1H); $^{19}$F NMR (376 MHz, CDCl$_3$) δ −139.97; ESIMS m/z 301 ([M+H]$^+$), 299 ([M−H]$^−$).

Example 39

Preparation of methyl 4-amino-6-(4-chlorophenyl)-5-fluoro-3-methoxypicolinate (Compound 31)

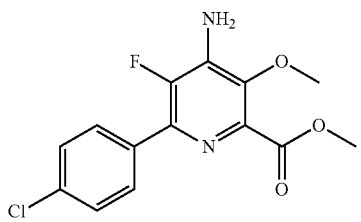 [SMILES: COC(=O)c1nc(-c2ccc(Cl)cc2)c(F)c(N)c1OC]

To a solution of methyl 4-amino-6-chloro-5-fluoro-3-methoxypicolinate (200 mg, 0.852 mmol) in CH$_3$CN (1.246 mL) and H$_2$O (1.246 mL) were added 2-(4-chlorophenyl)-1,3,2-dioxaborinane (251 mg, 1.279 mmol), KF (149 mg, 2.56 mmol), palladium(II) acetate (Pd(OAc)$_2$; 19.14 mg, 0.085 mmol), and triphenylphosphine-3,3′,3″-trisulfonic acid trisodium salt (100 mg, 0.170 mmol). The reaction mixture was then heated in a bench top Biotage microwave at 150° C. for 5 min. The reaction mixture was diluted with CH$_2$Cl$_2$ and washed with H$_2$O. The organic layer was separated, dried over MgSO$_4$, filtered and concentrated. The crude residue was purified by normal phase chromatography (eluting with 10% EtOAc/40% CH$_2$Cl$_2$/50% hexanes) to afford the title compound as a tan solid (191 mg, 72.1%): mp 93-94° C.; $^1$H NMR (400 MHz, acetone-d$_6$) δ 7.96 (dd, J=8.8, 1.4 Hz, 2H), 7.57-7.49 (m, 2H), 5.93 (s, 2H), 3.92 (s, 3H), 3.91 (s, 3H), ESIMS m/z 311 ([M+H]$^+$), 309 ([M−H]$^−$).

Compound 32 in Table 1 was synthesized as in Example 39.

Example 40

Preparation of methyl 4-amino-6-(4-chloro-2-fluoro-3-(1-fluoroethyl)phenyl)-5-fluoro-3-methoxypicolinate (Compound 33)

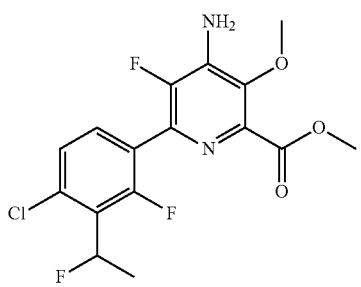 [SMILES: COC(=O)c1nc(-c2ccc(Cl)c(C(C)F)c2F)c(F)c(N)c1OC]

Methyl 4-amino-6-chloro-5-fluoro-3-methoxypicolinate (0.400 g, 1.705 mmol), 2-(4-chloro-2-fluoro-3-(1-fluoroethyl)phenyl)-4,4,5,5-tetramethyl-1,3,2-dioxaborolane (prepared as described in WO2009029735 A1 20090305; 0.671 g, 2.216 mmol), PdCl$_2$(PPh$_3$)$_2$ (0.120 g, 0.170 mmol), and KF (0.258 g, 4.43 mmol) were combined in a 1:1 mixture of CH$_3$CN (2.84 mL) and H$_2$O (2.84 mL). The reaction mixture was irradiated in a Biotage microwave at 115° C. in a sealed vial for 20 min. The cooled reaction mixture was partitioned between EtOAc and H$_2$O. The organic phase was dried and concentrated. The product was purified by flash chromatography (SiO$_2$, 5-40% EtOAc in hexane gradient) to provide the title compound as a sticky brown-orange solid (0.545 g, 81%): $^1$H NMR (400 MHz, CDCl$_3$) δ 7.53-7.46 (m, 1H), 7.29 (dt, J=8.4, 1.1 Hz, 1H), 6.39-6.03 (m, 1H), 4.61 (s, 2H), 3.97 (d, J=2.1 Hz, 6H), 1.85-1.68 (m, 3H); $^{19}$F NMR (376 MHz, CDCl$_3$) δ −113.81, −113.87, −113.90, −113.95, −137.05, −137.14, −175.47, −175.52; ESIMS m/z 375 ([M+H]$^+$), 373 ([M−H]$^−$).

Compounds 34-43 and 69 in Table 1 were synthesized as in Example 40.

Example 41

Preparation of methyl 4-amino-5-chloro-6-(4-chlorophenyl)-3-methoxy-picolinate (Compound 44)

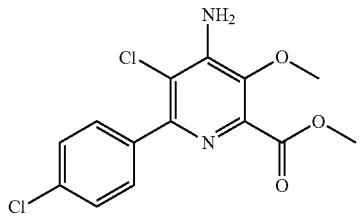

To a 5 mL microwave vial were added methyl 4-amino-6-bromo-5-chloro-3-methoxypicolinate (200 mg, 0.677 mmol), 4-chlorophenylboronic acid (116 mg, 0.744 mmol), KF (102 mg, 1.760 mmol), and PdCl$_2$(PPh$_3$)$_2$ (48 mg, 0.068 mmol). Subsequently, CH$_3$CN (1.1 mL) and H$_2$O (1.1 mL) were added, and the reaction vial was sealed and heated in a Biotage microwave at 115° C. for 20 min. The reaction mixture was cooled to room temperature and diluted with EtOAc (3 mL). The organic phase was separated, and the aqueous phase was washed with EtOAc (2×2 mL). The organic extracts were combined, dried over Na$_2$SO$_4$, filtered, and concentrated in vacuo. The crude product was using a Teledyne ISCO purification system with a gradient eluent system of EtOAc and hexanes to yield the title compound as a white solid (106 mg, 47%): mp 139-141° C.; $^1$H NMR (400 MHz, DMSO-d$_6$) δ 7.60-7.54 (m, 2H), 7.54-7.47 (m, 2H), 6.68 (s, 2H), 3.84 (s, 3H), 3.77 (s, 3H); ESIMS m/z 326.00 ([M−H]$^−$).

Example 42

Preparation of 4-amino-6-(4-chloro-2-fluoro-3-methoxyphenyl)-5-fluoro-3-methoxypicolinic acid (Compound 45)

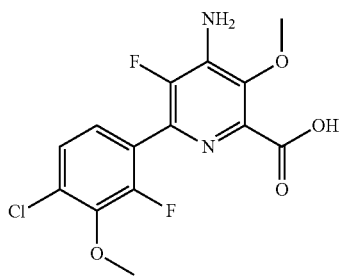 [SMILES: COc1c(C(=O)O)nc(-c2ccc(Cl)c(OC)c2F)c(F)c1N]

Methyl 4-amino-6-(4-chloro-2-fluoro-3-methoxyphenyl)-5-fluoro-3-methoxypicolinate (0.77 g, 2.15 mmol) was dissolved in CH$_3$OH (14 mL) and 2 N sodium hydroxide (NaOH; 4.3 mL) was added. The solution was stirred at room temperature overnight, acidified with 2 N HCl and concentrated to remove the majority of CH$_3$OH. The precipitate that formed was filtered, washed with H$_2$O and dried under vacuum to provide the title compound as a white solid (668 mg, 90%): mp 143-146° C.; $^1$H NMR (400 MHz, CDCl$_3$) δ 7.30 (dd, J=8.5, 1.6 Hz, 1H), 7.19 (dd, J=8.4, 6.8 Hz, 1H), 4.83 (s, 2H), 4.07 (s, 3H), 4.02 (d, J=1.1 Hz, 3H); $^{19}$F NMR (376 MHz, CDCl$_3$) δ −128.66, −128.74, −134.93, −135.01; ESIMS m/z 345 ([M+H]$^+$), 343 ([M−H]$^−$).

Compounds 46-65 and 70-71 in Table 1 were synthesized as in Example 42.

Example 43

Preparation of benzyl 4-amino-6-(4-chloro-2-fluoro-3-methoxyphenyl)-5-fluoro-3-methoxypicolinate (Compound 66)

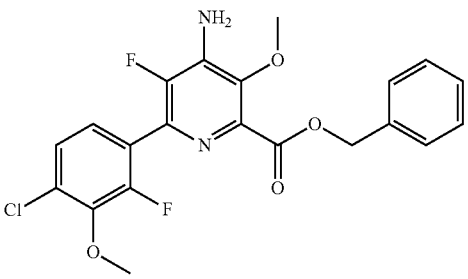 [SMILES: COc1c(C(=O)OCc2ccccc2)nc(-c2ccc(Cl)c(OC)c2F)c(F)c1N]

To a solution of 4-amino-6-(4-chloro-2-fluoro-3-methoxyphenyl)-5-fluoro-3-methoxypicolinic acid (140 mg, 0.406 mmol) in DMSO (1.354 mL) were added K$_2$CO$_3$ (67.4 mg, 0.487 mmol) and (bromomethyl)benzene (76 mg, 0.447 mmol). The reaction mixture was heated at 100° C. for 5 min in a Biotage microwave. The reaction mixture was then diluted with H$_2$O and extracted with CH$_2$Cl$_2$. The organic extracts were separated from the aqueous layer in a Biotage phase separator. The organic layer was then concentrated, and the residue was purified by flash chromatography (eluting with 0-50% acetone in hexanes) to afford a white solid (125 mg, 69%): mp 119° C.; $^1$H NMR (400 MHz, acetone-d$_6$) δ 7.56-7.49 (m, 2H), 7.43-7.27 (m, 5H), 5.98 (s, 2H), 5.40 (s, 2H), 3.97 (d, J=1.1 Hz, 3H), 3.85 (s, 3H), ESIMS m/z 436 ([M+H]$^+$), 434 ([M−H]$^−$).

Example 44

Preparation of ethyl 4-amino-6-(4-chloro-2-fluorophenyl)-3-(2,2,2-trifluoro-ethoxy)picolinate (Compound 67)

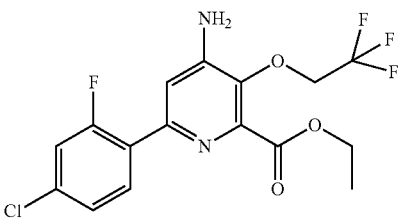 [SMILES: CCOC(=O)c1nc(-c2ccc(Cl)cc2F)cc(N)c1OCC(F)(F)F]

To a mixture of 2,2,2-trifluoroethanol (3.9 mL) and K$_2$CO$_3$ (54 mg, 3.9 mmol) was added (E)-ethyl 3-bromo-6-(4-chloro-2-fluorophenyl)-4-(((methylsulfonyl)oxy)imino)-1,4,5,6-tetrahydropicolinate (prepared as in Renga, J. M. et al. U.S. Patent Appl. Publ. 2010/0311594 A1, Dec. 9, 2010; 450 mg, 1 mmol). The mixture was stirred for 30 min, then diluted with Et$_2$O and washed with 1 M HCl. The organic extracts were dried with Na$_2$SO$_4$, filtered and concentrated in vacuo. The residue was purified by flash chromatography (eluting with 0-50% EtOAc/hexanes affording an off-white solid: (190 mg, 74%): mp 123-135° C.; $^1$H NMR (300 MHz, CDCl$_3$) δ 8.00 (t, J=8.5 Hz, 1H), 7.23 (m, 3H), 7.15 (dd, J=11.1, 2.0 Hz, 1H), 4.59 (s, 2H), 4.46 (m, 4H), 1.44 (t, J=7.1 Hz, 3H); ESIMS m/z 393 ([M+H]$^+$), 391 ([M−H]$^−$).

Compound 68 in Table 1 was synthesized as in Example 44.

Example 45

Preparation of methyl 4-amino-3-methoxy-6-vinylpicolinate (Compound 85)

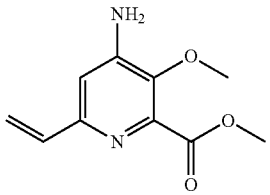

Methyl 4-amino-6-bromo-3-methoxypicolinate (1 g, 3.83 mmol), tributyl(vinyl)stannane (1.822 g, 5.75 mmol) and bis(triphenylphosphine)palladium(II) chloride (0.403 g, 0.575 mmol) in DCE (12.77 ml) were stirred at 70° C. overnight. The mixture was adsorbed onto celite and purified by flash column chromatography (ISCO, SiO2 40 g, hexane/EtOAc 100:0 to 0:100 gradient) to afford methyl 4-amino-3-methoxy-6-vinylpicolinate (263 mg, 1.263 mmol, 33% yield) as a yellow oil. EIMS m/z 208; $^1$H NMR (400 MHz, CDCl$_3$) δ 6.86 (s, 1H), 6.71 (dd, J=17.6, 10.9 Hz, 1H), 5.98 (dd, J=17.6, 1.0 Hz, 1H), 5.42 (dd, J=10.9, 1.0 Hz, 1H), 4.45 (s, 2H), 3.97 (s, 3H), 3.87 (s, 3H). $^{13}$C NMR (101 MHz, CDCl$_3$) δ 165.94, 152.06, 148.02, 143.34, 141.60, 136.73, 118.02, 108.63, 61.49, 52.84.

Example 46

Preparation of methyl 4-[bis(tert-butoxycarbonyl)amino]-6-ethenyl-3-methoxypyridine-2-carboxylate

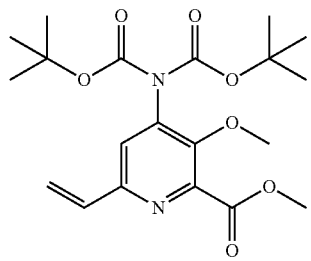 [SMILES: C=Cc1cc(N(C(=O)OC(C)(C)C)C(=O)OC(C)(C)C)c(OC)c(C(=O)OC)n1]

To a solution of methyl 4-amino-3-methoxy-6-vinylpicolinate (0.263 g, 1.263 mmol) in DCE (6.32 ml) was added di-tert-butyl dicarbonate (0.827 g, 3.79 mmol) and N,N-dimethylpyridin-4-amine (0.023 g, 0.189 mmol). The reaction mixture was stirred at room temperature overnight. The mixture was adsorbed onto celite and purified by flash column chromatography (ISCO, SiO2, 24 g, hexane/EtOAc 100:0 to 0:100 gradient) to afford methyl 4-[bis(tert-butoxycarbonyl)amino]-6-ethenyl-3-methoxypyridine-2-carboxylate (382 mg, 0.935 mmol, 74.0% yield) as a colorless oil. ESIMS m/z 409 ([M+H]$^+$); $^1$H NMR (400 MHz, CDCl$_3$) δ 7.30 (s, 1H), 6.81 (dd, J=17.5, 10.9 Hz, 1H), 6.08 (d, J=17.4 Hz, 1H), 5.51 (d, J=11.1 Hz, 1H), 3.99 (s, 3H), 3.86 (s, 3H), 1.42 (s, 18H).

Example 47

Preparation of methyl 4-[bis(tert-butoxycarbonyl)amino]-6-formyl-3-methoxypyridine-2-carboxylate

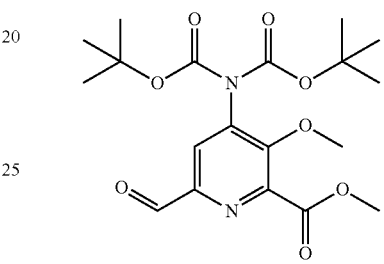

Ozone was bubbled through a solution of methyl 4-[bis(tert-butoxycarbonyl)amino]6-ethenyl-3-methoxypyridine-2-carboxylate (0.382 g, 0.935 mmol) in CH$_2$Cl$_2$ (9.35 ml) at −78° C. until the solution turned blue. Oxygen was bubbled through the reaction mixture until the solution turned yellow and triphenylphosphine (0.294 g, 1.122 mmol) was added. The reaction mixture was allowed to warm to room temperature and was stirred overnight. The reaction mixture was then adsorbed onto celite and the residue was purified by flash column chromatography (ISCO, SiO2 24 g, hexanes/EtOAc 100:0 to 0:100 gradient) to afford methyl 4-[bis(tert-butoxycarbonyl)amino]-6-formyl-3-methoxypyridine-2-carboxylate (279 mg, 0.680 mmol, 72.7% yield) as a light yellow oil. ESIMS m/z 411 ([M−H]$^+$); $^1$H NMR (400 MHz, CDCl$_3$) δ 10.03 (s, 1H), 7.88 (s, 1H), 4.05 (s, 3H), 3.95 (s, 3H), 1.43 (s, 18H).

Example 48

Preparation of 4-amino-6-(difluoromethyl)-3-methoxypicolinate (Compound 92)

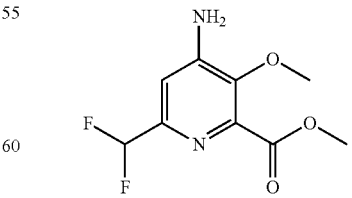

To a 0° C. solution of methyl 4-[bis(tert-butoxycarbonyl)amino]-6-formyl-3-methoxypyridine-2-carboxylate (0.279 g, 0.680 mmol) in CH$_2$Cl$_2$ (2.72 ml) was added DEOXO-FLUOR® (0.251 ml, 1.360 mmol). The mixture was stirred at 0° C. for 1 h (reaction completed based on TLC and LC). TFA (1 mL) was then added and the reaction mixture was allowed to slowly warm to room temperature and was stirred overnight. The mixture was poured into saturated NaHCO₃ and extracted with EtOAc (2×). The combined organic layers were dried over MgSO4, filtered and concentrated. The residue was purified by flash column chromatography (ISCO, SiO2 12 g, hexanes/EtOAc 100:0 to 0:100 gradient) to afford methyl 4-amino-6-(difluoromethyl)-3-methoxypicolinate (89 mg, 0.383 mmol, 56.4% yield) as a white solid. ESIMS m/z 233 ([M+H]$^+$); $^1$H NMR (400 MHz, CDCl$_3$) δ 7.06 (s, 1H), 6.54 (t, J=55.4 Hz, 1H), 4.69 (s, 2H), 3.98 (s, 3H), 3.90 (s, 3H); $^{19}$F NMR (376 MHz, CDCl$_3$) δ −114.65.

Example 49

Preparation of 4-amino-6-(1-ethoxyvinyl)-3-methoxypicolinate

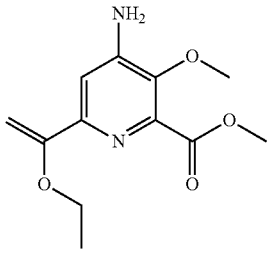 [SMILES: C=C(OCC)c1cc(N)c(OC)c(C(=O)OC)n1]

Methyl 4-amino-6-bromo-3-methoxypicolinate (2 g, 7.66 mmol), tributyl(1-ethoxyvinyl)stannane (4.15 g, 11.49 mmol) and bis(triphenylphosphine)palladium(ii) chloride (0.807 g, 1.149 mmol) in DCE (19.15 ml) were stirred under microwave irradiation (120° C., 30 min). The reaction was not completed (LC). Additional tin reagent (1 equiv) and palladium catalyst (0.15 equiv) were added and the reaction mixture was stirred under microwave irradiation (120° C., 30 min). The mixture was adsorbed onto celite and purified by flash column chromatography (ISCO, SiO2 80 g, hexane/EtOAc 100:0 to 0:100 gradient) to afford methyl 4-amino-6-(1-ethoxyvinyl)-3-methoxypicolinate (1.68 g, 6.66 mmol, 87% yield) as a yellow solid. Mp 72-73° C.; EIMS m/z 253 ([M+H]$^+$); $^1$H NMR (400 MHz, CDCl$_3$) δ 7.15 (s, 1H), 5.34 (d, J=2.0 Hz, 1H), 4.45 (s, 2H), 4.31 (d, J=1.9 Hz, 1H), 3.96 (s, 3H), 3.92 (q, J=7 Hz, 2H), 3.86 (s, 3H), 1.41 (t, J=7.0 Hz, 3H).

Example 50

Preparation of methyl 6-acetyl-4-amino-3-methoxypicolinate

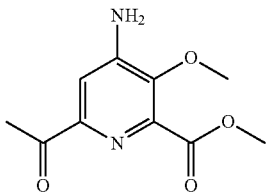 [SMILES: COC(=O)c1nc(C(C)=O)cc(N)c1OC]

To a solution of methyl 4-amino-6-(1-ethoxyvinyl)-3-methoxypicolinate (1.68 g, 6.66 mmol) in THF (44.4 ml) was added a 2 N solution of hydrochloric acid (6.66 ml, 13.32 mmol). The milky solution was stirred at room temperature overnight. The clear yellow reaction mixture was concentrated. The residue was poured into saturated NaHCO3 and extracted with EtOAc (3×). The combined organic layers were dried over MgSO4, filtered, concentrated and dried in vacuo to afford methyl 6-acetyl-4-amino-3-methoxypicolinate (1.55 g, 6.91 mmol, 104% yield) as an orange solid which was used without further purification in the next step. ESIMS m/z 223 ([M−H]$^−$); $^1$H NMR (400 MHz, CDCl$_3$) δ 7.47 (s, 1H), 4.59 (s, 2H), 4.01 (s, 3H), 3.90 (s, 3H), 2.67 (s, 3H).

Example 51

Preparation of methyl 4-amino-6-(1-hydroxyethyl)-3-methoxypicolinate

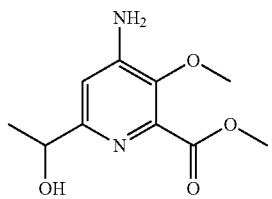 [SMILES: COC(=O)c1nc(C(C)O)cc(N)c1OC]

To a 0° C. solution of methyl 6-acetyl-4-amino-3-methoxypicolinate (0.75 g, 3.35 mmol) in MeOH (11.15 ml) was added sodium borohydride (0.127 g, 3.35 mmol) by portion. The reaction mixture was stirred at room temperature (TLC monitoring). After 2 h, the reaction mixture was poured into saturated NaHCO3 and extracted with EtOAc (2×) and CH$_2$Cl$_2$ (1×). The combined organic layers were dried over MgSO4, filtered, concentrated and dried in vacuo to afford methyl 4-amino-6-(1-hydroxyethyl)-3-methoxypicolinate (0.548 g, 2.422 mmol, 72.4% yield) as a brown oil, which was used without further purification in the next step. $^1$H NMR (400 MHz, CDCl$_3$) δ 6.72 (s, 1H), 4.76 (q, J=6.4 Hz, 1H), 4.52 (s, 2H), 3.96 (s, 3H), 3.94 (s, 1H), 3.86 (s, 3H), 1.45 (d, J=6.5 Hz, 3H).

Example 52

Preparation of methyl 4-amino-6-(1-fluoroethyl)-3-methoxypicolinate (Compound 83)

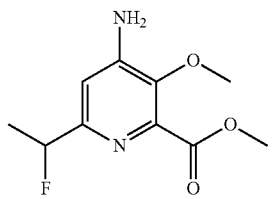 [SMILES: COC(=O)c1nc(C(C)F)cc(N)c1OC]

To a −10° C. (ice+NaCl) suspension of methyl 4-amino-6-(1-hydroxyethyl)-3-methoxypicolinate (0.3 g, 1.326 mmol) in Chloroform (6.63 ml) was added dropwise Triflic Acid (0.141 ml, 1.591 mmol) followed by Deoxo-Fluor® (0.257 ml, 1.392 mmol). The suspension was stirred at −10° C. (LC monitoring). After 2 h, the reaction mixture was poured into saturated NaHCO3 and extracted with EtOAc (3×). The combined organic layers were dried over MgSO4, filtered and concentrated. The residue was purified by flash column chromatography (ISCO, SiO2 24 g, hexane/EtOAc 100:0 to 0:100 gradient) to afford methyl 4-amino-6-(1-fluoroethyl)-3-methoxypicolinate (175 mg, 0.767 mmol, 57.8% yield) as a white solid. ESIMS m/z 227 ([M−H]$^-$); $^1$H NMR (400 MHz, CDCl$_3$) δ 6.91 (s, 1H), 5.59 (dq, J=47.6, 6.3 Hz, 1H), 4.53 (s, 2H), 3.97 (s, 3H), 3.87 (s, 3H), 1.62 (dd, J=24.6, 6.4 Hz, 3H); $^{19}$F NMR (376 MHz, CDCl$_3$) δ −176.20.

Example 53

Preparation of 4-amino-6-(1-fluoroethyl)-3-methoxypicolinic acid (Compound 84)

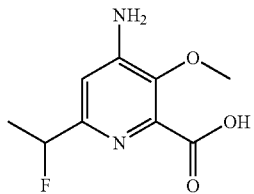

To a solution of methyl 4-amino-6-(1-fluoroethyl)-3-methoxypicolinate (0.125 g, 0.548 mmol) in THF (2.74 ml) and MeOH (2.74 ml) was added a 2 N solution of sodium hydroxide (0.822 ml, 1.643 mmol). The reaction mixture was stirred at room temperature (LC monitoring). After 4 h, the reaction mixture was acidified with a 2 N solution of HCl (1 mL) and then concentrated (rotavap). The resulting white solid was dissolved into DMF+a few drops of water and was purified by preparative HPLC (reverse phase, C18 column) to afford 4-amino-6-(1-fluoroethyl)-3-methoxypicolinic acid (98 mg, 0.458 mmol, 84% yield) as an orange solid. ESIMS m/z 213 ([M−H]$^-$); $^1$H NMR (400 MHz, DMSO) δ 9.06 (s, 1H), 6.82 (s, 1H), 6.47 (s, 2H), 5.49 (dq, J=47.7, 6.3 Hz, 1H), 3.69 (s, 3H), 2.51 (d, J=24.0 Hz, 1H), 1.52 (dd, J=24.5, 6.4 Hz, 3H); $^{19}$F NMR (376 MHz, DMSO) δ −171.64.

Example 54

Preparation of methyl 6-acetyl-4-[bis(tert-butoxycarbonyl)amino]-3-methoxypyridine-2-carboxylate

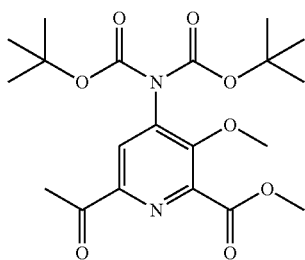 [SMILES: COC(=O)c1nc(C(C)=O)cc(N(C(=O)OC(C)(C)C)C(=O)OC(C)(C)C)c1OC]

To a solution of methyl 6-acetyl-4-amino-3-methoxypicolinate (0.800 g, 3.57 mmol) in DCE (11.89 ml) was added di-tert-butyl dicarbonate (2.336 g, 10.70 mmol) and N,N-dimethylpyridin-4-amine (0.065 g, 0.535 mmol). The reaction mixture was stirred at room temperature overnight. The mixture was adsorbed onto celite and purified by flash column chromatography (ISCO, SiO2, 40 g, hexane/EtOAc 100:0 to 0:100 gradient) to afford methyl 6-acetyl-4-[bis(tert-butoxycarbonyl)amino]-3-methoxypyridine-2-carboxylate (1.34 g, 3.16 mmol, 88% yield) as a colorless oil. ESIMS m/z 425 ([M+H]+); $^1$H NMR (400 MHz, CDCl$_3$) δ 7.95 (s, 1H), 4.02 (s, 3H), 3.92 (s, 3H), 2.71 (s, 3H), 1.42 (s, 18H); $^{13}$C NMR (101 MHz, CDCl$_3$) δ 198.07, 165.21, 154.04, 150.15, 148.89, 143.72, 142.39, 124.67, 84.30, 62.27, 53.11, 27.90, 25.60.

Example 55

Preparation of methyl 4-amino-6-(1,1-difluoroethyl)-3-methoxypicolinate (Compound 81)

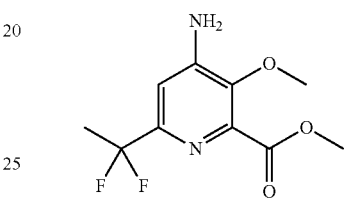

To a solution of methyl 6-acetyl-4-[bis(tert-butoxycarbonyl)amino]-3-methoxypyridine-2-carboxylate (0.7 g, 1.649 mmol) in DCE (3.30 ml) was added Deoxo-Fluor® (1.520 ml, 8.25 mmol) and the reaction mixture was stirred at 80° C. overnight. The mixture was allowed to cool down to room temperature and TFA (2 mL) was added. The reaction mixture was stirred at room temperature (LC monitoring). After 12 h, the reaction was completed and extracted with EtOAc (2×). The combined organic layers were dried over MgSO4, filtered and concentrated. The residue was purified by flash column chromatography (ISCO, SiO2 24 g, hexane/EtOAc 100:0 to 0:100 gradient) to afford methyl 4-amino-6-(1,1-difluoroethyl)-3-methoxypicolinate (336 mg, 1.365 mmol, 83% yield) as an orange oil. ESIMS m/z 245 ([M−H]$^-$); $^1$H NMR (400 MHz, CDCl$_3$) δ 7.06 (s, 1H), 4.59 (s, 2H), 3.97 (s, 3H), 3.88 (s, 3H), 1.98 (t, J=18.7 Hz, 3H); $^{19}$F NMR (376 MHz, CDCl$_3$) δ −89.99.

Example 56

Preparation of 4-amino-6-(1,1-difluoroethyl)-3-methoxypicolinic acid (Compound 82)

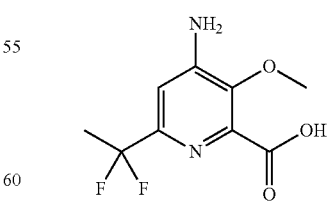

To a solution of methyl 4-amino-6-(1,1-difluoroethyl)-3-methoxypicolinate (0.229 g, 0.930 mmol) in THF (2.325 ml) and MeOH (2.325 ml) was added a 2 N solution of sodium hydroxide (1.395 ml, 2.79 mmol). The reaction mixture was stirred at room temperature (LC monitoring). After 4 h, the reaction mixture was acidified with a 2 N solution of HCl (2 mL) and then concentrated (rotavap). The resulting white solid was dissolved into DMF and a few drops of water and was purified by preparative HPLC (reverse phase, C18 column) to afford 4-amino-6-(1,1-difluoroethyl)-3-methoxypicolinic acid (188 mg, 0.810 mmol, 87% yield) as an orange oil. EIMS m/z 208; $^1$H NMR (400 MHz, CDCl$_3$) δ 6.86 (s, 1H), 6.71 (dd, J=17.6, 10.9 Hz, 1H), 5.98 (dd, J=17.6, 1.0 Hz, 1H), 5.42 (dd, J=10.9, 1.0 Hz, 1H), 4.45 (s, 2H), 3.97 (s, 3H), 3.87 (s, 3H); $^{13}$C NMR (101 MHz, CDCl$_3$) δ 165.94, 152.06, 148.02, 143.34, 141.60, 136.73, 118.02, 108.63, 61.49, 52.84.

Example 57

Preparation of Ethyl 4-amino-6-(4-chloro-2-fluoro-3-methoxyphenyl)-3-(methylthio)picolinate (Compound 88)

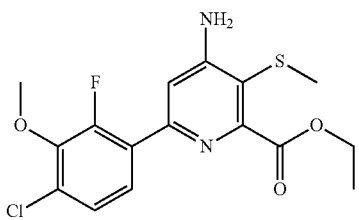

To a solution of (E)-methyl 3-chloro-6-(4-chloro-2-fluoro-3-methoxyphenyl)-4-(((methylsulfonyl)oxy)imino)-1,4,5,6-tetrahydropyridine-2-carboxylate (200 mg, 0.44 mmol) in DMSO (1.4 mL) was added K$_2$CO$_3$ (181 mg, 1.3 mmol) followed by sodium thiomethoxide (93 mg, 1.3 mmol). After 10 min the reaction was quenched with 1 M HCl solution and then extracted with diethyl ether. The organics were washed with brine, dried with Na$_2$SO$_4$, filtered and purified by silica gel chromatography eluting with 30% Et$_2$O in pentane to yielded to afford a brown solid (56 mg, 34%): mp 93-94° C.; $^1$H NMR (300 MHz, CDCl$_3$) δ 7.67 (dd, J=8.6, 7.7 Hz, 1H), 7.22 (m, 1H), 7.11 (d, J=1.9 Hz, 1H), 5.16 (s, 2H), 4.47 (q, J=7.1 Hz, 2H), 3.96 (d, J=0.9 Hz, 3H), 2.30 (d, J=1.7 Hz, 3H), 1.43 (t, J=7.1 Hz, 3H); ESIMS m/z 369 ([M−H]$^-$).

Example 58

Methyl 3-amino-6-(4-chlorophenyl)-4-(methylamino)picolinate (Compound 86)

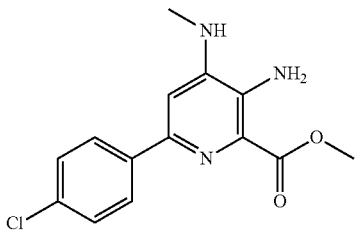 [SMILES: CNc1cc(-c2ccc(Cl)cc2)nc(C(=O)OC)c1N]

To a solution (E)-methyl 3-chloro-6-(4-chlorophenyl)-4-(((methylsulfonyl)oxy)imino)-1,4,5,6-tetrahydropyridine-2-carboxylate (100 mg, 0.254 mmol) in DMSO (2 mL) was added 2 M methanamine in THF (0.8 mL, 1.6 mmol). The reaction mixture was stirred at ambient temp for 30 min, and then it was diluted with H$_2$O. The product crashed out of solution, and was collect in a Buchner funnel, and dried under vacuum to yielded a brown solid (49 mg, 66%): mp 178-200° C.; $^1$H NMR (300 MHz, CDCl$_3$) δ 7.88 (d, J=8.4 Hz, 1H), 7.39 (d, J=8.5 Hz, 1H), 6.95 (s, 1H), 5.39 (s, 1H), 4.07 (s, 1H), 3.98 (s, 1H), 2.98 (d, J=5.1 Hz, 1H); ESIMS m/z 292 ([M+H]$^+$), 290 ([M−H]$^-$).

Example 59

Methyl 3-amino-6-(4-chlorophenyl)-4-(dimethylamino)picolinate (Compound 87)

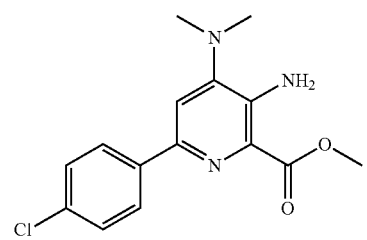 [SMILES: COC(=O)c1nc(-c2ccc(Cl)cc2)cc(N(C)C)c1N]

To a solution (E)-methyl 3-chloro-6-(4-chlorophenyl)-4-(((methylsulfonyl)oxy)imino)-1,4,5,6-tetrahydropyridine-2-carboxylate (100 mg, 0.254 mmol) in DMSO (2 mL) was added 2 M dimethylamine in THF (0.8 mL, 1.6 mmol). The reaction mixture was stirred at ambient temperature for 30 min, and then it was diluted with H$_2$O. The resulting mixture was extracted with Et$_2$O, dried, concentrated and purified by silica gel chromatography eluting with 20% EtOAc in pentane to afford a brown solid. (45 mg, 58%): mp 153-154° C., $^1$H NMR (300 MHz, CDCl$_3$) δ 7.85 (d, J=8.5 Hz, 2H), 7.39 (d, J=8.7 Hz, 2H), 7.34 (s, 1H), 6.06 (s, 2H), 3.98 (s, 3H), 2.79 (s, 6H); ESIMS m/z 306 ([M+H]$^+$).

Example 60

Ethyl 4-amino-6-(4-chloro-2-fluorophenyl)-3-((2,2,2-trifluoroethyl)thio)picolinate (Compound 89)

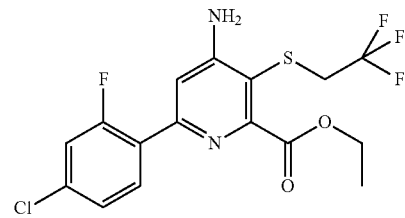

To a solution of (E)-ethyl 3-bromo-6-(4-chloro-2-fluorophenyl)-4-(((methylsulfonyl)oxy)imino)-1,4,5,6-tetrahydropyridine-2-carboxylate (200 mg, 0.43 mmol) in 2,2,2-trifluoroethanethiol (1.4 mL) was added K$_2$CO$_3$ (235 mg, 1.7 mmol). The solution were stirred for 1 h then diluted with H$_2$O, extracted with EtOAc, dried with Na$_2$SO$_4$ filtered and concentrated in vacuo. The residues were purified by silica gel chromatography to afford a yellow solid (130 mg, 75%, 80% pure, remaining 20% is ethyl 3-amino-6-(4-chloro-2-fluorophenyl)-4-((2,2,2-trifluoroethyl)thio)picolinate): $^1$H NMR (400 MHz, CDCl$_3$) δ 8.02 (m, 1H), 7.23 (m, 1H), 7.16 (m, 16H), 5.20 (s, 2H), 4.48 (q, J=7.1 Hz, 2H), 3.42 (q, J=10.0

Hz, 2H), 1.44 (t, J=7.1 Hz, 3H); $^{19}$F NMR (376 MHz, CDCl$_3$) δ −66.36 (s), −113.57 (s); ESIMS m/z 409 ([M+H]$^+$), 407 ([M−H]$^−$).

Example 61

Preparation of Methyl 4-amino-6-(4-chloro-3-fluorophenyl)-5-fluoro-3-(methylthio)picolinate (Compound 93)

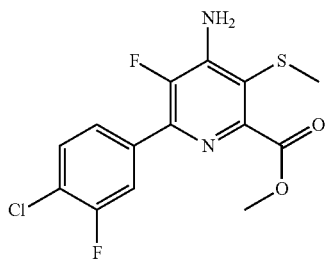

Methyl 4-amino-6-(4-chloro-3-fluorophenyl)-5-fluoro-3-iodopicolinate (420 mg, 0.99 mmol) and tri-n-butylmethylthiostannane (530 mg, 1.6 mmol) were dissolved in 5 ml dry DMF. The solution was purged with a nitrogen stream for 10 m, treated with his (triphenylphosphine) palladium (II) chloride (70 mg, 0.01 mmol) and copper (I) iodide (19 mg, 0.01 mmol) and heated to 100° C. After 5 h, an additional 350 mg, 1.0 mmol, of the stannane were added and heating was continued for 8 h more. After cooling, the mixture was stirred with 10 ml water and 50 ml ethyl acetate and then filtered through a glass wool plug to remove yellow solids. The organic phase was separated and stirred with 25 ml 10% aq. potassium bifluoride solution for 30 m. After filtration through diatomaceous earth, the solution was washed with 10 ml water, 10 ml sat. NaCl, dried (Na$_2$SO$_3$) and evaporated. The crude material was purified by silica gel chromatography using a 0-40% ethyl acetate-hexane gradient. After evaporation of the solvents the oily product was stirred with hexane to produce a white solid which was collected by filtration and dried under vacuum to give 260 mg of the written product as a white solid: mp 125-126° C.; $^1$H NMR (400 MHz, CDCl$_3$) δ 7.77 (dd, J=28.9, 9.5 Hz, 2H), 7.47 (m, 1H), 5.28 (s, 2H), 3.99 (s, 3H), 2.35 (s, 3H). $^{19}$F NMR (376 MHz, CDCl$_3$) δ −115.10, −143.40; ESIMS m/z 345 ([M+H]$^+$), 343 ([M−H]$^−$).

Example 62

Preparation of Methyl 4-amino-6-chloro-5-fluoro-3-(methylthio)picolinate (Compound 74)

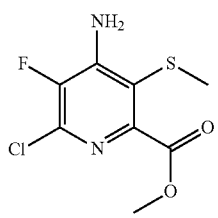

Methyl 4-amino-6-chloro-5-fluoro-3-iodopicolinate (1.5 g, 4.6 mmol), tri-n-butylmethylthiostannane (2.5 g, 7.3 mmol), his (triphenylphosphine) palladium (II) chloride (320 mg, 0.46 mmol) and copper (I) iodide (90 mg, 0.46 mmol) were combined 15 ml dry, deaerated DMF and heated to 80° C. After 3 h another 2.5 g portion of the stannane were added and heating was continued for 18 h. After cooling, the mixture was stirred with 25 ml 10% potassium bifluoride solution for 20 ml. The heterogeneous mixture was stirred with 100 ml ethyl acetate and filtered through diatomaceous earth to remove curdy solids. The separated organic phase was washed twice with 15 ml water, 15 ml sat. NaCl, dried (Na$_2$SO$_3$) and evaporated. The product was purified by silica gel chromatography eluting with a 0-25% ethyl acetate-DCM gradient. The gummy residue was stirred with hexane to produce the written product as a white solid, 800 mg. Mp: 75-77° C. $^1$H NMR (400 MHz, CDCl$_3$) δ 5.35 (s, 2H), 3.96 (s, 3H), 2.33 (s, 3H). $^{19}$F NMR (376 MHz, CDCl$_3$) δ −138.81. EIMS m/z 250.

Example 63

Preparation of Methyl 4-amino-6-(4-chloro-2-fluoro-3-methoxyphenyl)-5-fluoro-3-(methylthio)picolinate (Compound 94)

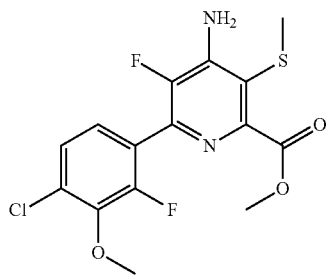 [SMILES: COC(=O)c1nc(-c2ccc(Cl)c(OC)c2F)c(F)c(N)c1SC]

Methyl 4-amino-6-chloro-5-fluoro-3-(methylthio)picolinate (300 mg, 1.2 mmol), 2-(4-chloro-2-fluoro-3-methoxyphenyl)-4,4,5,5-tetramethyl-1,3,2-dioxaborolane (450 mg, 1.6 mmol) Cesium fluoride (370 mg, 2.4 mmol) and his (triphenylphosphine) palladium (II) chloride (84 mg, 0.12 mmol) were combined in 5 ml 1:1 acetonitrile-water and heated in a microwave reactor at 115° C. for 30 m. The mixture was shaken with 30 ml ethyl acetate and 10 ml water. The org. phase was washed with 10 ml sat. NaCl, dried (Na$_2$SO$_3$) and evaporated. The residue was chromatographed on silica with a 0-40% ethyl acetate-hexane gradient. The gummy material was stirred with hexane to produce the written compound as a white solid, 60 mg. Mp: 113-117° C. $^1$H NMR (400 MHz, CDCl$_3$) δ 7.27-7.24 (m, 2H), 5.31 (s, 2H), 3.98 (d, J=1.1 Hz, 3H), 3.96 (s, 3H), 2.32 (s, 3H). $^{19}$F NMR (376 MHz, CDCl$_3$) δ −127.97, −128.06, −140.43, −140.52. ESIMS m/z 375 ([M+H]$^+$), 373 ([M−H]$^−$).

Example 64

Preparation of methyl 4-amino-3-fluoro-5,6'-dimethoxy-[2,3'-bipyridine]-6-carboxylate (Compound 75)

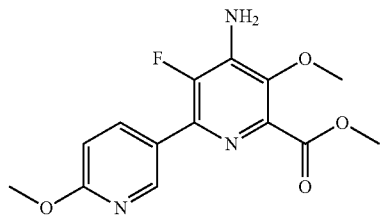

To a tube, methyl 4-amino-6-chloro-5-fluoro-3-methoxypicolinate (500 mg, 2.131 mmol), (6-methoxypyridin-3-yl)boronic acid (391 mg, 2.56 mmol), [1,1'-Bis(diphenylphosphino)ferrocene]dichloropalladium(II) (78 mg, 0.107 mmol) and Cesium Fluoride (647 mg, 4.26 mmol) were charged as solids. The tube was sealed and charged with inert atmosphere. The solids were then diluted with Dioxane (5700 µl) and Water (1400 µl). The resulting suspension was heated to 85° C. for 18 hrs. The reaction solution was poured in to a brine solution. The aqueous phase was extracted with EtOAc (3×25 mL). The combined organic layers were dried over MgSO$_4$, filtered and concentrated under vacuum. The product was purified (flash chromatography: silica, 5-50% EtOAc in Hex 16 CV; C$_{18}$ 5-100% ACN in H$_2$O 16 CV) to yield methyl 4-amino-3-fluoro-5,6'-dimethoxy-[2,3'-bipyridine]-6-carboxylate (186 mg, 0.605 mmol, 28.4% yield). ESIMS for m/z 308 (M+H)$^+$. $^1$H NMR (400 MHz, DMSO-d$_6$) δ 3.77 (s, 3H), 3.86 (s, 3H), 3.92 (s, 3H), 6.53 (s, 2H), 6.95 (dd, J=8.6, 0.8 Hz, 1H), 8.10 (ddd, J=8.6, 2.4, 1.1 Hz, 1H), 8.58 (t, J=2.0 Hz, 1H). $^{19}$F NMR (376 MHz, DMSO-d$_6$) δ −141.20.

Example 65

Preparation of 4-amino-3-fluoro-5,6'-dimethoxy-[2,3'-bipyridine]-6-carboxylic acid (Compound 78)

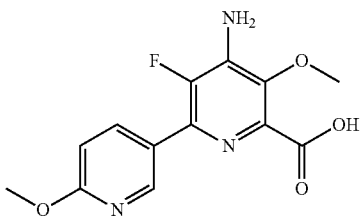 [SMILES: COc1ccc(-c2nc(C(=O)O)c(OC)c(N)c2F)cn1]

To a solution of methyl 4-amino-3-fluoro-5,6'-dimethoxy-[2,3'-bipyridine]-6-carboxylate (100 mg, 0.325 mmol) in THF (1.0 mL), MeOH (1.000 mL), and Water (0.500 mL), lithium hydroxide hydrate (60 mg, 1.430 mmol) was added as a solid. The solution was stirred at room temperature for 18 hrs. The reaction solution was then concentrated under vacuum to dryness. The resulting solid was suspended in H$_2$O and the pH was adjusted to 3.8, forming a ppt. The suspension was extracted with EtOAc (3×25 mL). The combined organic layers were dried over MgSO$_4$, filtered and concentrated under vacuum to yield 4-amino-3-fluoro-5,6'-dimethoxy-[2,3'-bipyridine]-6-carboxylic acid (80.1 mg, 0.273 mmol, 84% yield).). ESIMS for m/z 294 (M+H)$^+$. $^1$H NMR (400 MHz, DMSO-d$_6$) δ 3.78 (s, 3H), 3.92 (s, 3H), 6.47 (s, 2H), 6.95 (dd, J=8.7, 0.8 Hz, 1H), 8.15 (ddd, J=8.7, 2.4, 1.1 Hz, 1H), 8.61 (t, J=2.1 Hz, 1H), 13.02 (s, 1H). $^{19}$F NMR (376 MHz, DMSO-d$_6$) δ −141.78.

Example 66

Preparation of methyl 4-amino-6'-cyclopropyl-3-fluoro-5-methoxy-[2,3'-bipyridine]-6-carboxylate (Compound 76)

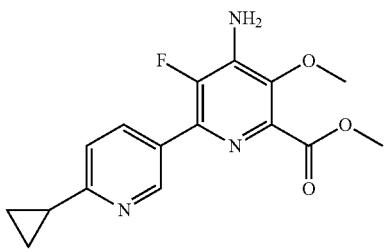 [SMILES: COC(=O)c1nc(-c2ccc(C3CC3)nc2)c(F)c(N)c1OC]

To a tube, methyl 4-amino-6-chloro-5-fluoro-3-methoxypicolinate (500 mg, 2.131 mmol) (~90% pure), (6-cyclopropylpyridin-3-yl)boronic acid (417 mg, 2.56 mmol), [1,1'-Bis(diphenylphosphino)ferrocene]dichloropalladium(II) (78 mg, 0.107 mmol), and Cesium Fluoride (647 mg, 4.26 mmol) were charged as solids. The tube was sealed and charged with inert atmosphere. The solids were then diluted with Dioxane (5.7 ml) and Water (1.4 ml). The resulting suspension was heated to 85° C. for 18 hrs. The reaction solution was poured in to a brine solution. The aqueous phase was extracted with EtOAc (3×25 mL). The combined organic layers were dried over MgSO$_4$, filtered and concentrated under vacuum. The product was purified (flash chromatography: silica, 5-50% EtOAc in Hex 16 CV; C$_{18}$ 5-100% ACN in H$_2$O 16 CV) to yield methyl 4-amino-6'-cyclopropyl-3-fluoro-5-methoxy-[2,3'-bipyridine]-6-carboxylate (0.218 g, 0.687 mmol, 32.2% yield). ESIMS for m/z 318 (M+H)$^+$. $^1$H NMR (400 MHz, DMSO-d$_6$) δ 0.99 (tt, J=7.6, 2.7 Hz, 4H), 2.17 (tt, J=7.8, 5.1 Hz, 1H), 3.77 (s, 3H), 3.86 (s, 3H), 6.55 (s, 2H), 7.42 (d, J=8.9 Hz, 1H), 8.00 (ddd, J=8.2, 2.3, 1.2 Hz, 1H), 8.77 (t, J=2.0 Hz, 1H). $^{19}$F NMR (376 MHz, DMSO-d$_6$) δ −141.19.

Example 67

Preparation of 4-amino-6'-cyclopropyl-3-fluoro-5-methoxy-[2,3'-bipyridine]-6-carboxylic acid (Compound 77)

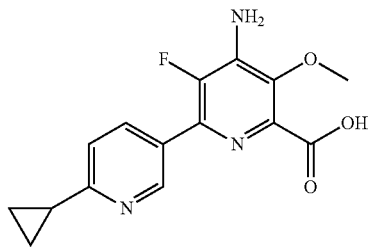 [SMILES: COc1c(C(=O)O)nc(-c2ccc(C3CC3)nc2)c(F)c1N]

To a solution of methyl 4-amino-6'-cyclopropyl-3-fluoro-5-methoxy-[2,3'-bipyridine]-6-carboxylate (100 mg, 0.315 mmol) in THF (1.00 mL), MeOH (1.000 mL), and Water (0.500 mL), lithium hydroxide hydrate (65 mg, 1.549 mmol) was added as a solid. The reaction was allowed to stir at room temperature for 18 hrs. The reaction solution was then concentrated under vacuum to dryness. The resulting solid was suspended in H$_2$O and the pH was adjusted to 4.0, forming a ppt. The suspension was extracted with EtOAc (3×25 mL). The combined organic layers were dried over MgSO$_4$, filtered and concentrated under vacuum to yield 4-amino-6'-cyclopropyl-3-fluoro-5-methoxy-[2,3'-bipyridine]-6-carboxylic acid (50.0 mg, 0.165 mmol, 52.3% yield). ESIMS for m/z 304 (M+H)$^+$. $^1$H NMR (400 MHz, DMSO-d$_6$) δ 0.92-1.06 (m, 4H), 2.17 (tt, J=7.8, 5.1 Hz, 1H), 3.78 (s, 3H), 6.49 (s, 2H), 7.42 (dd, J=8.3, 0.9 Hz, 1H), 8.05 (ddd, J=8.2, 2.2, 1.1 Hz, 1H), 8.81 (t, J=2.0 Hz, 1H), 13.03 (s, 1H). $^{19}$F NMR (376 MHz, DMSO-d$_6$) δ −141.73.

Example 68

Preparation of 4-amino-5-fluoro-3-methoxy-6-vinylpicolinic acid (Compound 95)

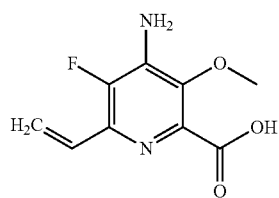

To a solution of methyl 4-amino-5-fluoro-3-methoxy-6-vinylpicolinate (140.0 mg, 0.619 mmol) in THF (1.2 mL), MeOH (1.200 mL), Water (0.600 mL), lithium hydroxide hydrate (78 mg, 1.857 mmol) was charged as a solid. The reaction was allowed to stir at room temperature for 18 hrs. The reaction was concentrated to dryness. The resulting residue was diluted with 2 N HCl and MeOH. The product was purified ($C_{18}$ 10-80% ACN in H2O 12 CV) to yield 4-amino-5-fluoro-3-methoxy-6-vinylpicolinic acid (79 mg, 0.372 mmol, 60.2% yield). ESIMS for m/z 213 (M+H)$^+$. $^1$H NMR (400 MHz, DMSO-$d_6$) δ 3.73 (s, 3H), 5.50 (dd, J=11.0, 2.2 Hz, 1H), 6.20 (dd, J=17.3, 2.2 Hz, 1H), 6.35 (s, 2H), 6.83 (ddd, J=17.3, 10.9, 1.7 Hz, 1H), 12.98 (s, 1H). $^{19}$F NMR (376 MHz, DMSO-$d_6$) δ −145.09.

TABLE 1

Structures of Compounds in Examples

| Compound Number | Structure | Prepared as described in Example: | Precursor |
|---|---|---|---|
| 1 | 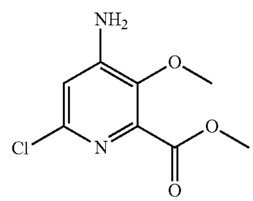 | 9 | Methyl 4,6-dichloro-3-methoxypicolinate |
| 2 | 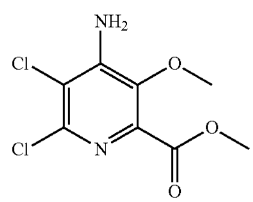 | 10 | Compound 1 |
| 3 | 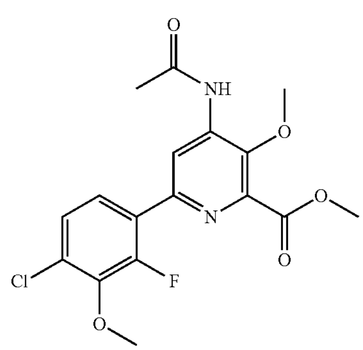 [SMILES: COC(=O)c1nc(-c2ccc(Cl)c(OC)c2F)cc(NC(C)=O)c1OC] | 12 | Methyl 4-acetamido-6-(4-chloro-2-fluoro-3-methoxyphenyl)-3-hydroxypicolinate |
| 4 | 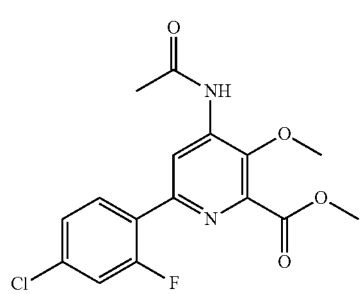 [SMILES: COC(=O)c1nc(-c2ccc(Cl)cc2F)cc(NC(C)=O)c1OC] | 12 | Methyl 4-acetamido-6-(4-chloro-2-fluorophenyl)-3-hydroxypicolinate |

TABLE 1-continued

Structures of Compounds in Examples

| Compound Number | Structure | Prepared as described in Example: | Precursor |
|---|---|---|---|
| 5 | 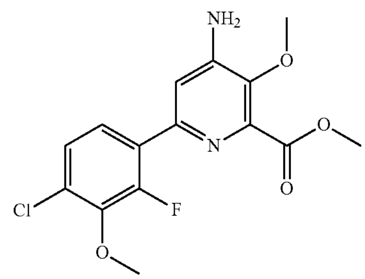 [SMILES: COC(=O)c1nc(-c2ccc(Cl)c(OC)c2F)cc(N)c1OC] | 13 | Compound 3 |
| 6 | 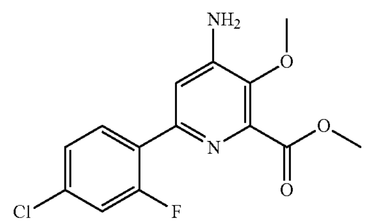 [SMILES: COC(=O)c1nc(-c2ccc(Cl)cc2F)cc(N)c1OC] | 13 | Compound 4 |
| 7 | 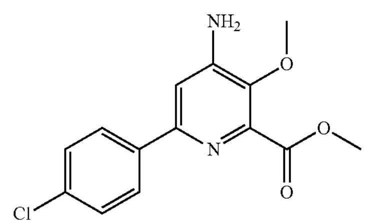 [SMILES: COC(=O)c1nc(-c2ccc(Cl)cc2)cc(N)c1OC] | 14 | methyl 4-amino-6-bromo-3-methoxypicolinate |
| 8 | 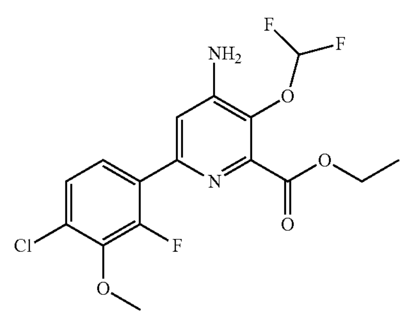 [SMILES: CCOC(=O)c1nc(-c2ccc(Cl)c(OC)c2F)cc(N)c1OC(F)F] | 19 | 2-Chloro-6-(4-chloro-2-fluoro-3-methoxyphenyl)-3-(difluoromethoxy)-pyridin-4-amine |
| 9 | 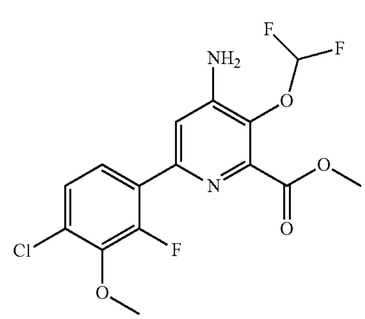 [SMILES: COC(=O)c1nc(-c2ccc(Cl)c(OC)c2F)cc(N)c1OC(F)F] | 19 | 2-Chloro-6-(4-chloro-2-fluoro-3-methoxyphenyl)-3-(difluoromethoxy)-pyridin-4-amine |

TABLE 1-continued

Structures of Compounds in Examples

| Compound Number | Structure | Prepared as described in Example: | Precursor |
|---|---|---|---|
| 10 | 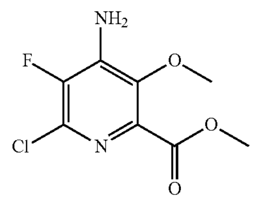 | 26 | methyl 4-amino-6-chloro-5-fluoro-3-iodopicolinate |
| 11 | 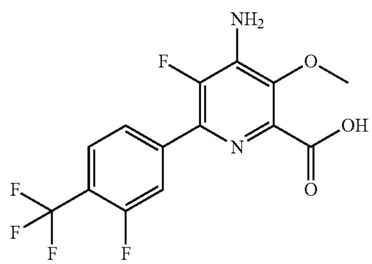 [SMILES: COc1c(C(=O)O)nc(-c2ccc(C(F)(F)F)c(F)c2)c(F)c1N] | 29 | Methyl 4-amino-5-fluoro-3-iodopicolinate |
| 12 | 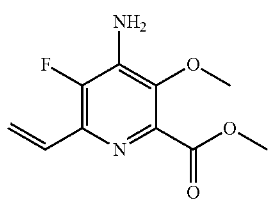 [SMILES: C=Cc1nc(C(=O)OC)c(OC)c(N)c1F] | 30 | Compound 10 |
| 13 | 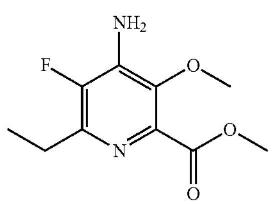 [SMILES: CCc1nc(C(=O)OC)c(OC)c(N)c1F] | 31 | Compound 12 |
| 14 | 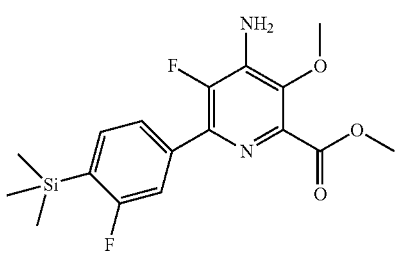 | 32 | Compound 10; (2-fluoro-4-(4,4,5,5-tetramethyl-1,3,2-dioxaborolan-2-yl)phenyl)-trimethylsilane |
| 15 | 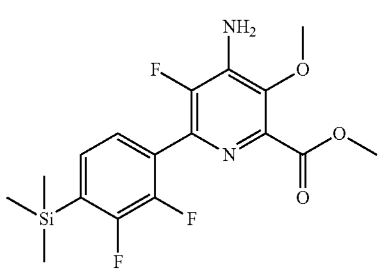 | 33 | Compound 10; (2,3-difluoro-4-(4,4,5,5-tetramethyl-1,3,2-dioxaborolane-2-yl)phenyl)-trimethylsilane |

TABLE 1-continued

Structures of Compounds in Examples

| Compound Number | Structure | Prepared as described in Example: | Precursor |
|---|---|---|---|
| 16 | 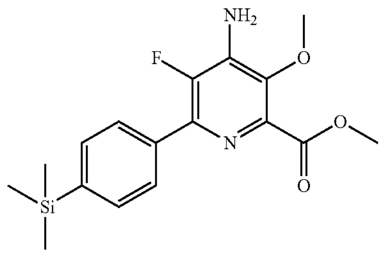 | 33 | Compound 10 |
| 17 | 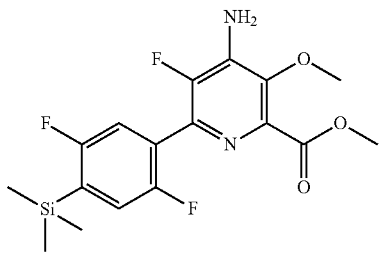 | 34 | Compound 10; (2,5-Difluoro-4-(4,4,5,5-tetramethyl-1,3,2-dioxaborolan-2-yl)phenyl)-trimethylsilane |
| 18 | 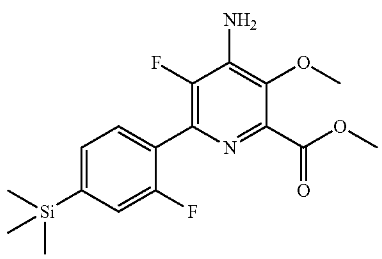 | 34 | Compound 10; (3-fluoro-4-(4,4,5,5-tetramethyl-1,3,2-dioxaborolan-2-yl)-phenyl)-trimethylsilane |
| 19 | 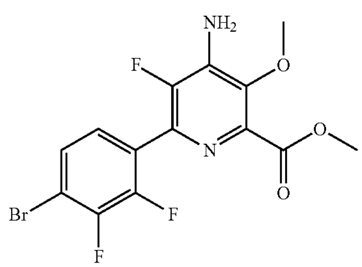 [SMILES: COC(=O)c1nc(-c2ccc(Br)c(F)c2F)c(F)c(N)c1OC] | 35 | Compound 15 |
| 20 | 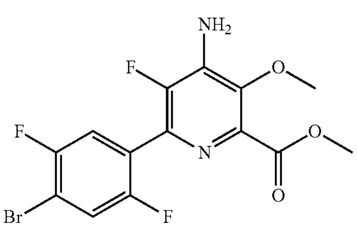 | 35 | Compound 17 |
| 21 | 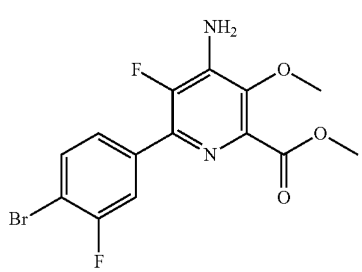 [SMILES: COC(=O)c1nc(-c2ccc(Br)c(F)c2)c(F)c(N)c1OC] | 35 | Compound 14 |

TABLE 1-continued

Structures of Compounds in Examples

| Compound Number | Structure | Prepared as described in Example: | Precursor |
|---|---|---|---|
| 22 | 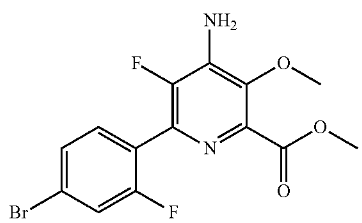 [SMILES: COC(=O)c1nc(-c2ccc(Br)cc2F)c(F)c(N)c1OC] | 35 | Compound 18 |
| 23 | 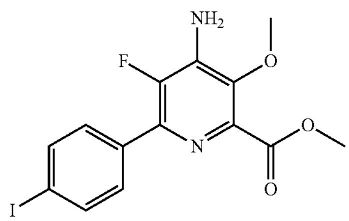 [SMILES: COC(=O)c1nc(-c2ccc(I)cc2)c(F)c(N)c1OC] | 36 | Compound 16 |
| 24 | 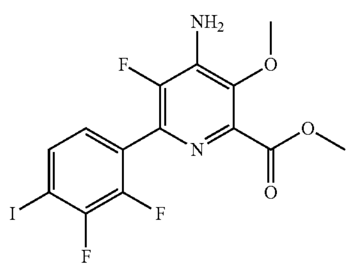 [SMILES: COC(=O)c1nc(-c2ccc(I)c(F)c2F)c(F)c(N)c1OC] | 36 | Compound 15 |
| 25 | 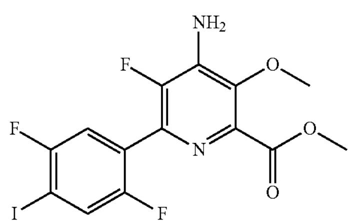 [SMILES: COC(=O)c1nc(-c2cc(F)c(I)cc2F)c(F)c(N)c1OC] | 36 | Compound 17 |
| 26 | 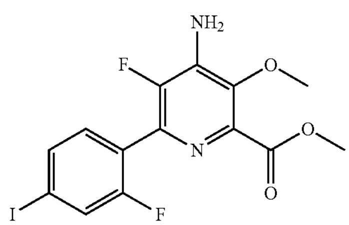 [SMILES: COC(=O)c1nc(-c2ccc(I)cc2F)c(F)c(N)c1OC] | 36 | Compound 18 |
| 27 | 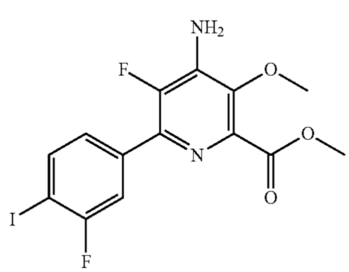 [SMILES: COC(=O)c1nc(-c2ccc(I)c(F)c2)c(F)c(N)c1OC] | 36 | Compound 14 |

TABLE 1-continued

Structures of Compounds in Examples

| Compound Number | Structure | Prepared as described in Example: | Precursor |
|---|---|---|---|
| 28 | 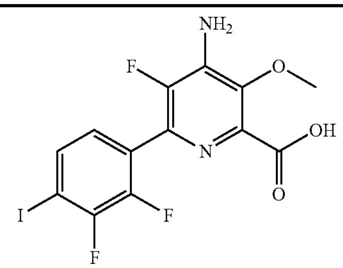 | 42 | Compound 24 |
| 29 | 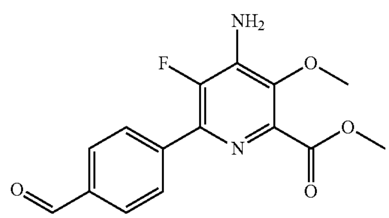 [SMILES: COC(=O)c1nc(-c2ccc(C=O)cc2)c(F)c(N)c1OC] | 37 | Compound 10 |
| 30 | 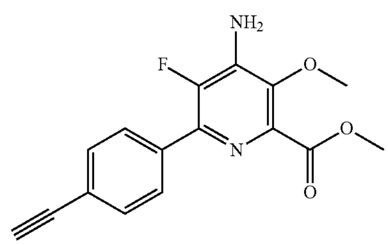 [SMILES: C#Cc1ccc(-c2nc(C(=O)OC)c(OC)c(N)c2F)cc1] | 38 | Compound 29 |
| 31 | 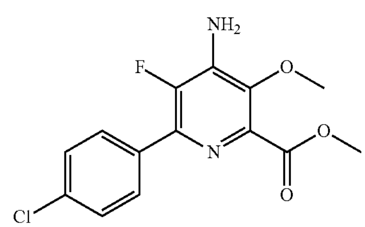 [SMILES: COC(=O)c1nc(-c2ccc(Cl)cc2)c(F)c(N)c1OC] | 39 | Compound 10 |
| 32 | 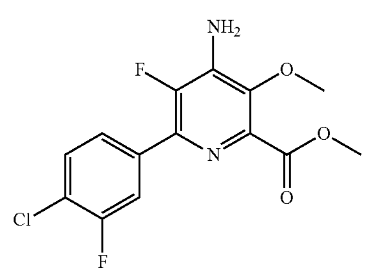 | 39 | Compound 10 |
| 33 | 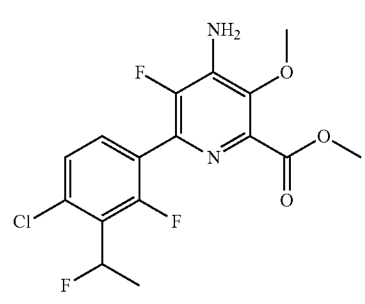 [SMILES: COC(=O)c1nc(-c2ccc(Cl)c(C(C)F)c2F)c(F)c(N)c1OC] | 40 | Compound 10 |

TABLE 1-continued

Structures of Compounds in Examples

| Compound Number | Structure | Prepared as described in Example: | Precursor |
|---|---|---|---|
| 34 | 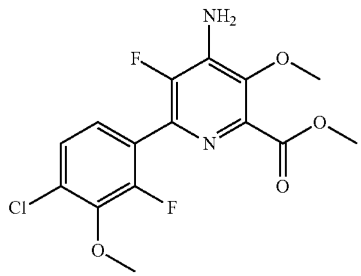 [SMILES: COC(=O)c1nc(-c2ccc(Cl)c(OC)c2F)c(F)c(N)c1OC] | 40 | Compound 10 |
| 35 | 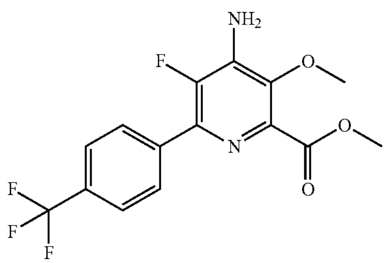 [SMILES: COC(=O)c1nc(-c2ccc(C(F)(F)F)cc2)c(F)c(N)c1OC] | 40 | Compound 10 |
| 36 | 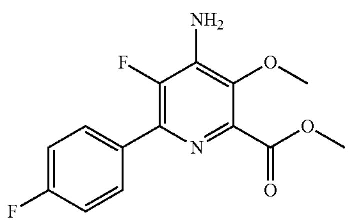 [SMILES: COC(=O)c1nc(-c2ccc(F)cc2)c(F)c(N)c1OC] | 40 | Compound 10 |
| 37 | 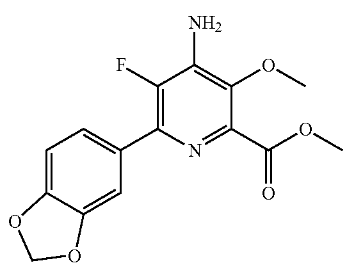 [SMILES: COC(=O)c1nc(-c2ccc3c(c2)OCO3)c(F)c(N)c1OC] | 40 | Compound 10 |
| 38 | 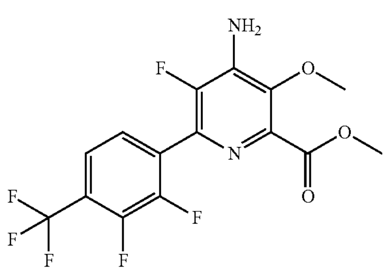 [SMILES: COC(=O)c1nc(-c2ccc(C(F)(F)F)c(F)c2F)c(F)c(N)c1OC] | 40 | Compound 10 |
| 39 | 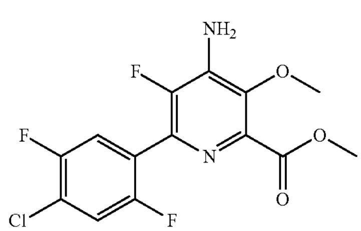 [SMILES: COC(=O)c1nc(-c2cc(F)c(Cl)cc2F)c(F)c(N)c1OC] | 40 | Compound 10 |

TABLE 1-continued

Structures of Compounds in Examples

| Compound Number | Structure | Prepared as described in Example: | Precursor |
|---|---|---|---|
| 40 | 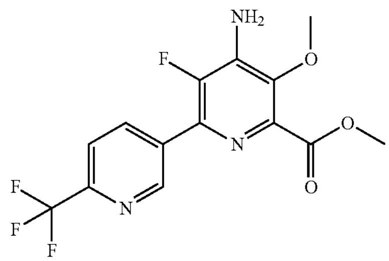 [SMILES: COC(=O)c1nc(-c2ccc(C(F)(F)F)nc2)c(F)c(N)c1OC] | 40 | Compound 10 |
| 41 | 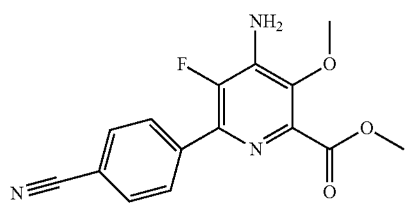 [SMILES: COC(=O)c1nc(-c2ccc(C#N)cc2)c(F)c(N)c1OC] | 40 | Compound 10 |
| 42 | 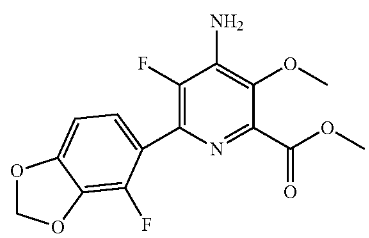 [SMILES: COC(=O)c1nc(-c2ccc3c(c2F)OCO3)c(F)c(N)c1OC] | 40 | Compound 10 |
| 43 | 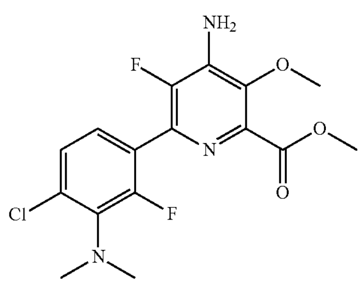 [SMILES: COC(=O)c1nc(-c2ccc(Cl)c(N(C)C)c2F)c(F)c(N)c1OC] | 40 | Compound 10 |
| 44 | 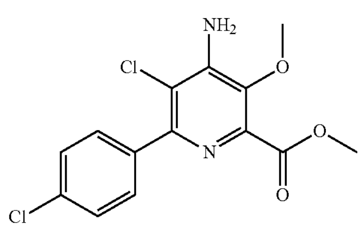 [SMILES: COC(=O)c1nc(-c2ccc(Cl)cc2)c(Cl)c(N)c1OC] | 41 | methyl 4-amino-6-bromo-5-chloro-3-methoxypicolinate |
| 45 | 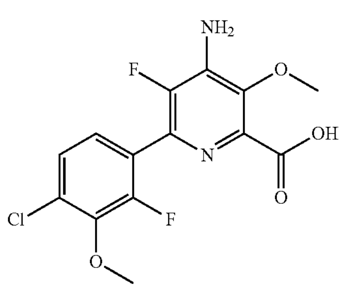 [SMILES: COc1c(C(=O)O)nc(-c2ccc(Cl)c(OC)c2F)c(F)c1N] | 42 | Compound 5 |

TABLE 1-continued

Structures of Compounds in Examples

| Compound Number | Structure | Prepared as described in Example: | Precursor |
|---|---|---|---|
| 46 | 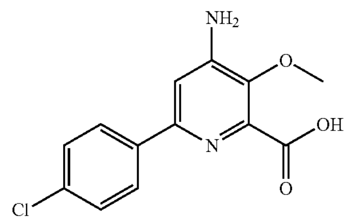 [SMILES: COc1c(N)cc(-c2ccc(Cl)cc2)nc1C(=O)O] | 42 | Compound 7 |
| 47 | 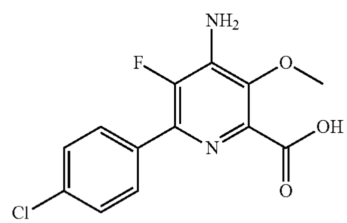 [SMILES: COc1c(C(=O)O)nc(-c2ccc(Cl)cc2)c(F)c1N] | 42 | Compound 31 |
| 48 | 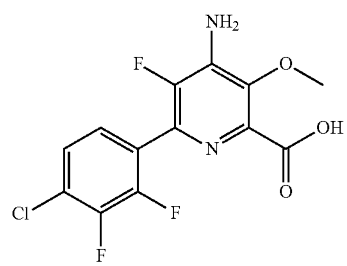 [SMILES: COc1c(C(=O)O)nc(-c2ccc(Cl)c(F)c2F)c(F)c1N] | 42 | Methyl 4-amino-6-(4-chloro-2,3-difluorophenyl)-5-fluoro-3-methoxypicolinate |
| 49 | 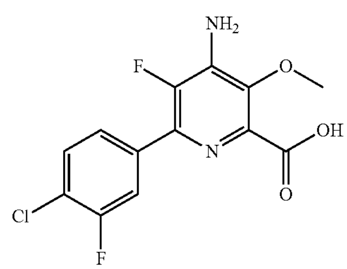 [SMILES: COc1c(C(=O)O)nc(-c2ccc(Cl)c(F)c2)c(F)c1N] | 42 | Compound 32 |
| 50 | 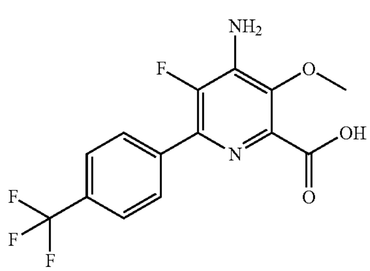 [SMILES: COc1c(C(=O)O)nc(-c2ccc(C(F)(F)F)cc2)c(F)c1N] | 42 | Compound 35 |
| 51 | 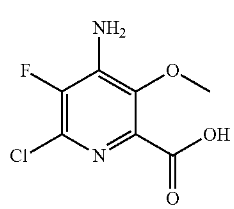 | 42 | Compound 10 |

TABLE 1-continued

Structures of Compounds in Examples

| Compound Number | Structure | Prepared as described in Example: | Precursor |
|---|---|---|---|
| 52 | 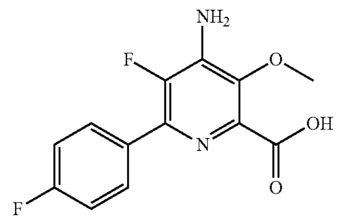 | 42 | Compound 36 |
| 53 | 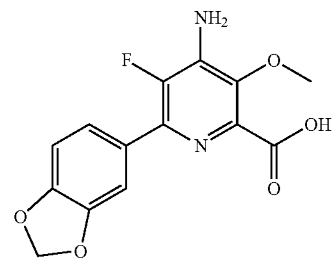 [SMILES: COc1c(C(=O)O)nc(-c2ccc3c(c2)OCO3)c(F)c1N] | 42 | Compound 37 |
| 54 | 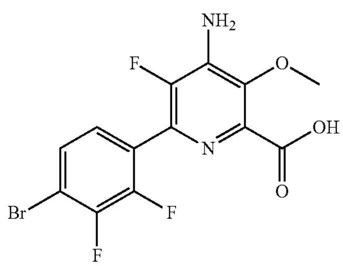 | 42 | Compound 19 |
| 55 | 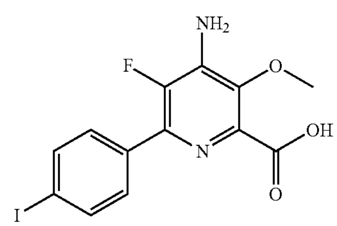 [SMILES: COc1c(C(=O)O)nc(-c2ccc(I)cc2)c(F)c1N] | 42 | Compound 23 |
| 56 | 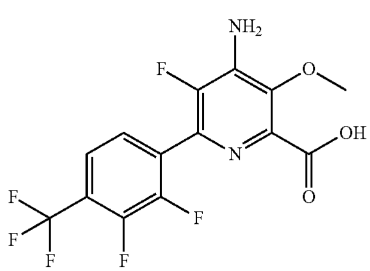 | 42 | Compound 38 |
| 57 | 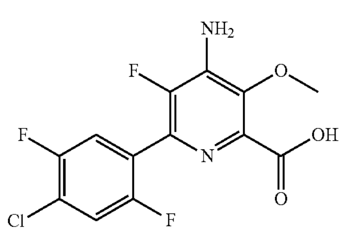 | 42 | Compound 39 |

TABLE 1-continued

Structures of Compounds in Examples

| Compound Number | Structure | Prepared as described in Example: | Precursor |
| --- | --- | --- | --- |
| 58 | 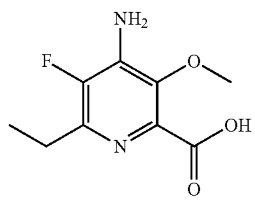 | 42 | Compound 13 |
| 59 | 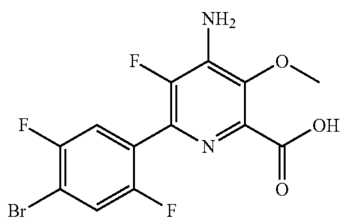 [SMILES: COc1c(C(=O)O)nc(-c2cc(F)c(Cl)cc2F)c(F)c1N] | 42 | Compound 20 |
| 60 | 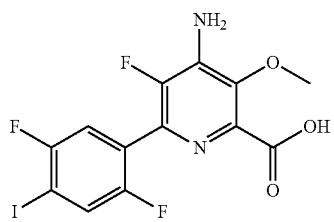 [SMILES: COc1c(C(=O)O)nc(-c2cc(F)c(I)cc2F)c(F)c1N] | 42 | Compound 25 |
| 61 | 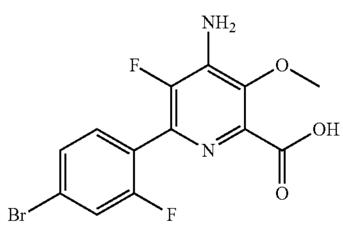 | 42 | Compound 22 |
| 62 | 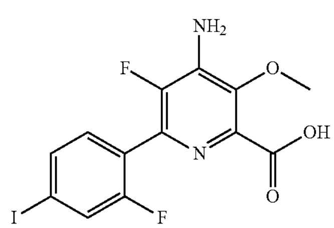 [SMILES: COc1c(C(=O)O)nc(-c2ccc(I)cc2F)c(F)c1N] | 42 | Compound 26 |
| 63 | 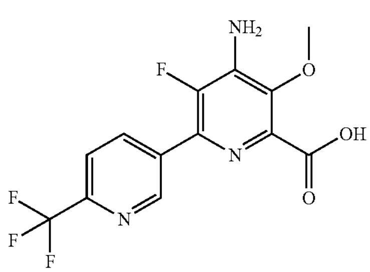 [SMILES: COc1c(C(=O)O)nc(-c2ccc(C(F)(F)F)nc2)c(F)c1N] | 42 | Compound 40 |

TABLE 1-continued

Structures of Compounds in Examples

| Compound Number | Structure | Prepared as described in Example: | Precursor |
|---|---|---|---|
| 64 | 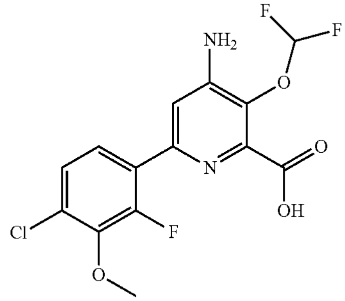 [SMILES: COc1c(Cl)ccc(-c2cc(N)c(OC(F)F)c(C(=O)O)n2)c1F] | 42 | Compound 9 |
| 65 | 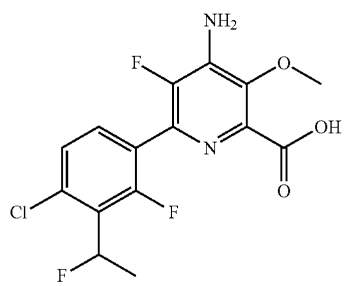 [SMILES: COc1c(C(=O)O)nc(-c2ccc(Cl)c(C(C)F)c2F)c(F)c1N] | 42 | Compound 33 |
| 66 | 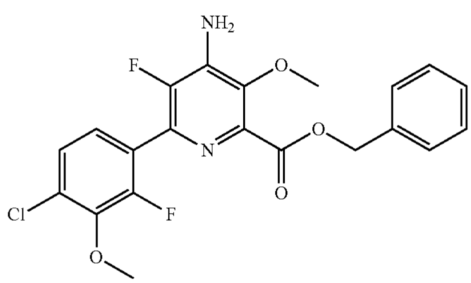 [SMILES: COc1c(C(=O)OCc2ccccc2)nc(-c2ccc(Cl)c(OC)c2F)c(F)c1N] | 43 | Compound 45 |
| 67 | 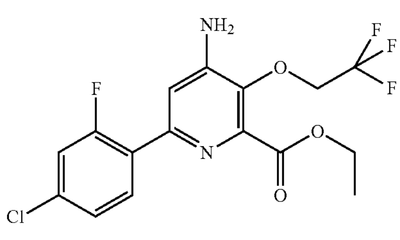 | 44 | (E)-ethyl 3-bromo-6-(4-chloro-2-fluorophenyl)-4-(((methylsulfonyl)oxy)imino)-1,4,5,6-tetrahydropicolinate |
| 68 | 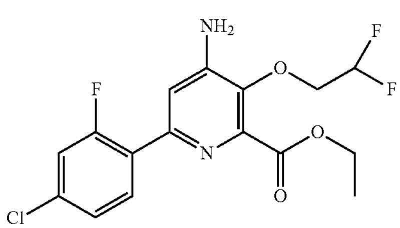 [SMILES: CCOC(=O)c1nc(-c2ccc(Cl)cc2F)cc(N)c1OCC(F)F] | 44 | (E)-ethyl 3-bromo-6-(4-chloro-2-fluorophenyl)-4-(((methylsulfonyl)oxy)imino)-1,4,5,6-tetrahydropicolinate |

TABLE 1-continued

Structures of Compounds in Examples

| Compound Number | Structure | Prepared as described in Example: | Precursor |
|---|---|---|---|
| 69 | 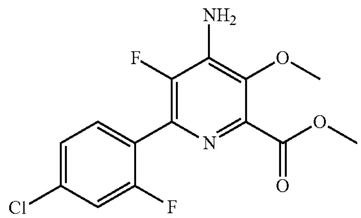 [SMILES: COC(=O)c1nc(-c2ccc(Cl)cc2F)c(F)c(N)c1OC] | 40 | Compound 10 |
| 70 | 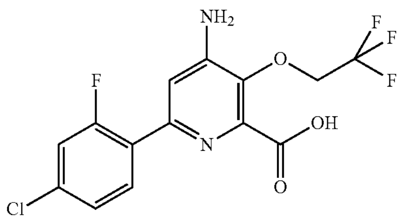 [SMILES: Nc1cc(-c2ccc(Cl)cc2F)nc(C(=O)O)c1OCC(F)(F)F] | 42 | Compound 67 |
| 71 | 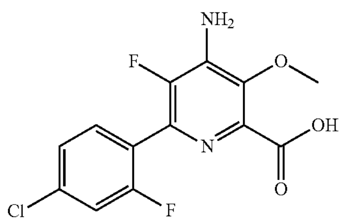 [SMILES: COc1c(C(=O)O)nc(-c2ccc(Cl)cc2F)c(F)c1N] | 42 | Compound 69 |
| 72 | 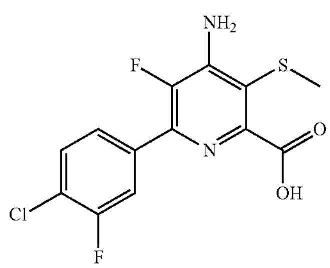 [SMILES: CSc1c(C(=O)O)nc(-c2ccc(Cl)c(F)c2)c(F)c1N] | 42 | Compound 93 |
| 73 | 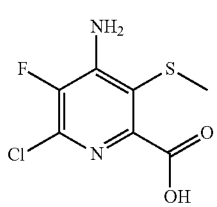 | 42 | Compound 74 |
| 74 | 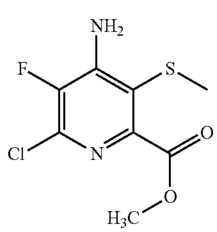 | 62 | methyl 4-amino-6-chloro-5-fluoro-3-iodopicolinate |

TABLE 1-continued

Structures of Compounds in Examples

| Compound Number | Structure | Prepared as described in Example: | Precursor |
|---|---|---|---|
| 75 | 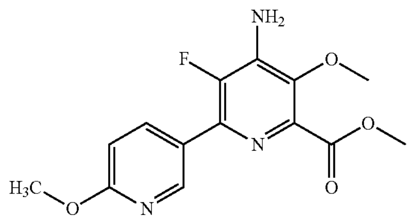 | 64 | Compound 10 |
| 76 | 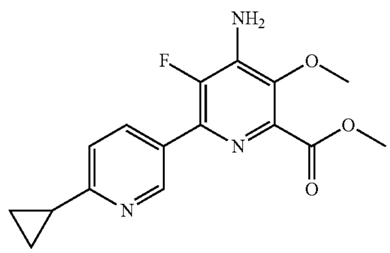 [SMILES: COC(=O)c1nc(-c2ccc(C3CC3)nc2)c(F)c(N)c1OC] | 66 | Compound 10 |
| 77 | 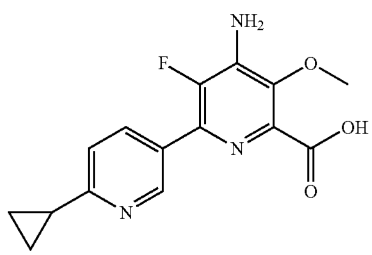 [SMILES: COc1c(C(=O)O)nc(-c2ccc(C3CC3)nc2)c(F)c1N] | 67 | Compound 76 |
| 78 | 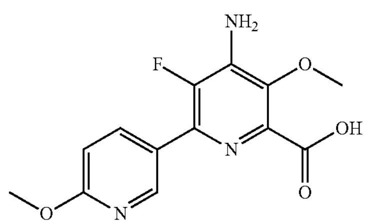 [SMILES: COc1ccc(-c2nc(C(=O)O)c(OC)c(N)c2F)cn1] | 65 | Compound 75 |
| 79 | 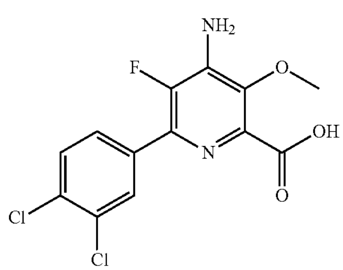 | 65 | Compound 80 |
| 80 | 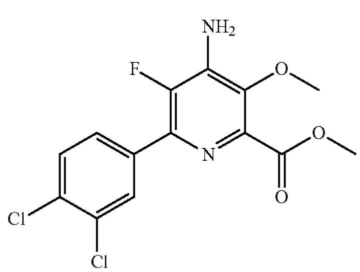 [SMILES: COC(=O)c1nc(-c2ccc(Cl)c(Cl)c2)c(F)c(N)c1OC] | 66 | Compound 10 |

TABLE 1-continued

Structures of Compounds in Examples

| Compound Number | Structure | Prepared as described in Example: | Precursor |
|---|---|---|---|
| 81 | 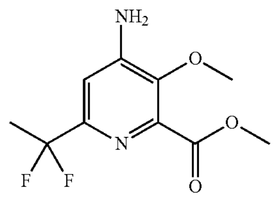 [SMILES: COC(=O)c1nc(C(C)(F)F)cc(N)c1OC] | 55 | methyl 6-acetyl-4-[bis(tert-butoxycarbonyl)-amino]-3-methoxypyridine-2-carboxylate |
| 82 | 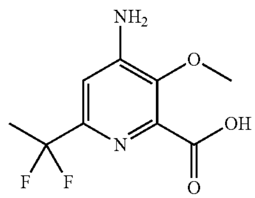 [SMILES: COc1c(N)cc(C(C)(F)F)nc1C(=O)O] | 56 | Compound 81 |
| 83 | 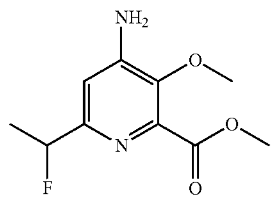 [SMILES: COC(=O)c1nc(C(C)F)cc(N)c1OC] | 52 | methyl 4-amino-6-(1-hydroxyethyl)-3-methoxypicolinate |
| 84 | 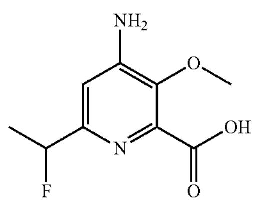 | 53 | Compound 83 |
| 85 | 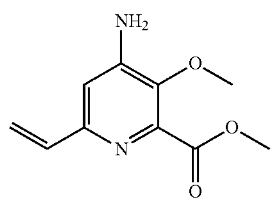 | 45 | Methyl 4-amino-6-bromo-3-methoxypicolinate |
| 86 | 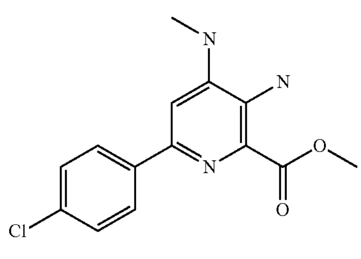 [SMILES: CNc1cc(-c2ccc(Cl)cc2)nc(C(=O)OC)c1N] | 58 | (E)-methyl 3-chloro-6-(4-chlorophenyl)-4-(((methylsulfonyl)-oxy)imino)-1,4,5,6-tetrahydropyridine-2-carboxylate |
| 87 | 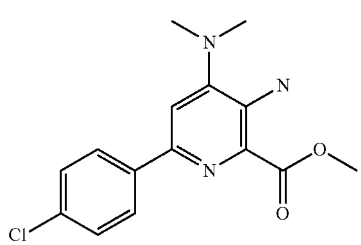 [SMILES: COC(=O)c1nc(-c2ccc(Cl)cc2)cc(N(C)C)c1N] | 59 | (E)-methyl 3-chloro-6-(4-chlorophenyl)-4-(((methylsulfonyl)-oxy)imino)-1,4,5,6-tetrahydropyridine-2-carboxylate |

TABLE 1-continued

Structures of Compounds in Examples

| Compound Number | Structure | Prepared as described in Example: | Precursor |
|---|---|---|---|
| 88 | 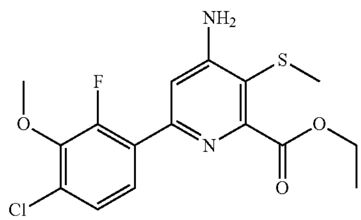 [SMILES: CCOC(=O)c1nc(-c2ccc(Cl)c(OC)c2F)cc(N)c1SC] | 57 | (E)-methyl 3-chloro-6-(4-chloro-2-fluoro-3-methoxyphenyl)-4-(((methylsulfonyl)-oxy)imino)-1,4,5,6-tetrahydropyridine-2-carboxylate |
| 89 | 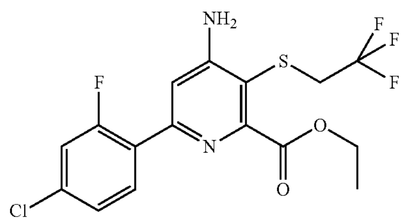 [SMILES: CCOC(=O)c1nc(-c2ccc(Cl)cc2F)cc(N)c1SCC(F)(F)F] | 60 | (E)-ethyl 3-bromo-6-(4-chloro-2-fluorophenyl)-4-(((methylsulfonyl)-oxy)imino)-1,4,5,6-tetrahydropyridine-2-carboxylate |
| 91 | 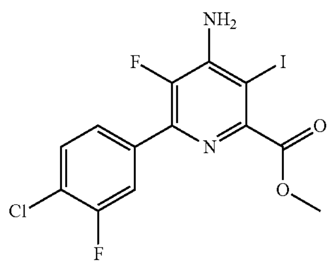 [SMILES: COC(=O)c1nc(-c2ccc(Cl)c(F)c2)c(F)c(N)c1I] | 28 | methyl 4-amino-6-(4-chloro-3-fluorophenyl)-5-fluoropicolinate |
| 92 | 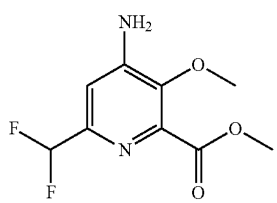 [SMILES: COC(=O)c1nc(C(F)F)cc(N)c1OC] | 48 | methyl 4-[bis(tert-butoxycarbonyl)-amino]-6-formyl-3-methoxypyridine-2-carboxylate |
| 93 | 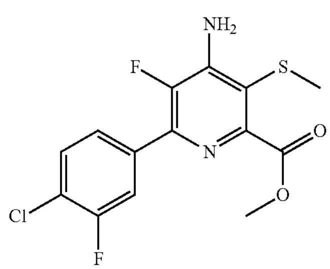 [SMILES: COC(=O)c1nc(-c2ccc(Cl)c(F)c2)c(F)c(N)c1SC] | 61 | Compound 91 |
| 94 | 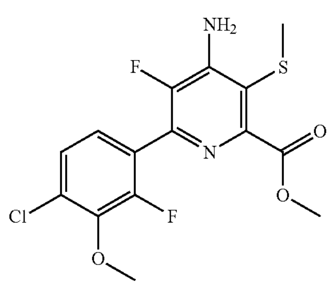 [SMILES: COC(=O)c1nc(-c2ccc(Cl)c(OC)c2F)c(F)c(N)c1SC] | 63 | Compound 74 |

TABLE 1-continued

Structures of Compounds in Examples

| Compound Number | Structure | Prepared as described in Example: | Precursor |
|---|---|---|---|
| 95 | 4-amino-5-fluoro-3-methoxy-6-vinylpyridine-2-carboxylic acid | 68 | Compound 12 |

TABLE 2

Analytical Data for Compounds in Table 1

| Compound Number | Appearance | mp (° C.) | ESIMS[1] m/z | $^1$H NMR (field strength, solvent) δ | Other NMR (field strength, solvent) δ |
|---|---|---|---|---|---|
| 1 | White Solid | 78-79 | EIMS m/z 216 | (400 MHz, CDCl$_3$) 6.76 (s, 1H), 4.84 (s, 2H), 3.95 (s, 3H), 3.87 (s, 3H) | |
| 2 | White Solid | 119-121 | EIMS m/z 250 | (400 MHz, CDCl$_3$) 5.04 (s, 2H), 3.97 (s, 3H), 3.93 (s, 3H) | |
| 3 | Yellow Oil | | 383 ([M + H]$^+$) | (400 MHz, CDCl$_3$) 8.93 (d, J = 1.6 Hz, 1H), 8.06 (s, 1H), 7.56 (dd, J = 8.5, 7.7 Hz, 1H), 7.23 (dd, J = 8.6, 1.7 Hz, 1H), 4.01 (s, 3H), 3.99 (d, J = 1.0 Hz, 3H), 3.98 (s, 3H), 2.29 (s, 3H) | |
| 4 | Yellow Oil | | 353 ([M + H]$^+$) | (400 MHz, CDCl$_3$) 8.96 (d, J = 1.5 Hz, 1H), 7.99 (s, 1H), 7.89 (t, J = 8.4 Hz, 1H), 7.23 (ddd, J = 8.4, 2.1, 0.6 Hz, 1H), 7.19 (dd, J = 10.7, 2.0 Hz, 1H), 4.02 (s, 3H), 3.99 (s, 3H), 2.29 (s, 3H) | |
| 5 | Off-White Solid | 114-118 | 341 ([M + H]$^+$), 339 ([M − H]$^−$) | (400 MHz, CDCl$_3$) 7.61 (dd, J = 8.5, 7.8 Hz, 1H), 7.22 (dd, J = 8.6, 1.8 Hz, 1H), 7.18 (d, J = 2.1 Hz, 1H), 4.54 (s, 1H), 3.98 (s, 2H), 3.96 (d, J = 0.8 Hz, 2H), 3.92 (s, 2H) | |
| 6 | White Solid | 139-144 | 311 ([M + H]$^+$) | (400 MHz, CDCl$_3$) 7.96 (t, J = 8.5 Hz, 1H), 7.25 (d, J = 1.3 Hz, 1H), 7.22 (dd, J = 2.0, 0.6 Hz, 1H), 7.15 (dd, J = 11.1, 2.0 Hz, 1H), 6.07 (s, 2H), 3.99 (s, 3H), 3.97 (s, 3H) | |
| 7 | Brown Oil | | 291 ([M − H]$^−$) | (300 MHz, CDCl$_3$) 7.90-7.81 (m, 2H), 7.46-7.36 (m, 2H), 7.12 (s, 1H), 4.56 (s, 2H), 4.01 (s, 3H), 3.92 (s, 3H) | |
| 8 | White Solid | | 391 ([M + H]$^+$), 389 ([M − H]$^−$) | (300 MHz, CDCl$_3$) 7.66 (dd, J = 8.6, 7.7 Hz, 1H), 7.28-7.24 (m, 1H), 7.22 (d, J = 1.7 Hz, 1H), 6.72 (t, J = 75.1 Hz, 1H), 4.73 (s, 2H), 4.46 (q, J = 7.1 Hz, 2H), 3.97 (d, J = 0.8 Hz, 3H), 1.42 (t, J = 7.2 Hz, 3H) | $^{19}$F NMR (376 MHz, CDCl$_3$) −79.74, −132.19 |
| 9 | White Solid | 162-164 | 375 ([M − H]$^+$) | (300 MHz, DMSO-d$_6$) 7.63 (m, 1H), 7.23 (m, 1H), 6.75 (t, J = 57 Hz, | |

TABLE 2-continued

Analytical Data for Compounds in Table 1

| Compound Number | Appearance | mp (° C.) | ESIMS[1] m/z | $^1$H NMR (field strength, solvent) δ | Other NMR (field strength, solvent) δ |
|---|---|---|---|---|---|
| | | | | 1H), 4.74 (s, 2H), 3.975 (d, J = 3 Hz, 3H) | |
| 10 | Purple Solid | | EIMS m/z 234 | (400 MHz, CDCl$_3$) 4.67 (s, 2H), 3.96 (s, 3H), 3.93 (s, 3H) | $^{19}$F NMR (376 MHz, CDCl$_3$) −135.15 (s) |
| 11 | Red Semi-Solid | | 347.81 ([M − H]−) | (400 MHz, CDCl$_3$) 7.83-7.63 (m, 4H), 4.89 (s, 2H), 4.08 (s, 3H) | $^{19}$F NMR (376 MHz, DMSO-d$_6$) −59.91, −59.93, −59.94, −115.72, −115.75, −140.39 |
| 12 | Yellow Liquid | | 227 ([M + H]+) | (400 MHz, CDCl$_3$) 6.88 (ddd, J = 17.5, 11.1, 1.4 Hz, 1H), 6.33 (dd, J = 17.5, 1.6 Hz, 1H), 5.57 (ddd, J = 11.1, 1.6, 0.7 Hz, 1H), 4.47 (s, 2H), 3.97 (s, 3H), 3.91 (s, 3H) | $^{19}$F NMR (376 MHz, CDCl$_3$) −143.2 |
| 13 | White Solid | 110.5-113.0 | EIMS m/z 228 | (400 MHz, CDCl$_3$) 4.41 (s, 2H), 3.96 (s, 3H), 3.90 (s, 3H), 2.81 (qd, J = 7.6, 2.7 Hz, 2H), 1.26 (t, J = 7.6 Hz, 3H) | $^{13}$C NMR (101 MHz, CDCl$_3$) 146.2, 144.2, 136.8, 136.1, 61.5, 52.7, 25.3, 12.9; $^{19}$F NMR (376 MHz, CDCl$_3$) −142.6 |
| 14 | Light Pink Oil | | 367 ([M + H]+) | (400 MHz, CDCl$_3$) 7.66 (d, J = 7.6 Hz, 1H), 7.55 (d, J = 9.8 Hz, 1H), 7.46 (dd, J = 7.6, 5.9 Hz, 1H), 4.57 (s, 2H), 3.98 (s, 3H), 3.96 (s, 3H), 0.33 (s, 9H) | $^{19}$F NMR (376 MHz, CDCl$_3$) −100.72, −140.12 |
| 15 | White Solid | 123-125 | 383.20 ([M − H]−) | (400 MHz, CDCl$_3$) 7.32 (ddd, J = 7.6, 5.5, 1.1 Hz, 1H), 7.20 (ddd, J = 7.7, 4.5, 1.4 Hz, 1H), 4.60 (s, 2H), 3.98 (s, 3H), 3.96 (s, 3H), 0.41-0.28 (m, 9H) | $^{19}$F NMR (376 MHz, CDCl$_3$) −127.39, −127.45, −127.46, −137.48, −137.56, −140.78, −140.85, −140.86, −140.92 |
| 16 | Red Solid | | 349.59 ([M + H]+) | (400 MHz, DMSO-d$_6$) 7.80-7.70 (m, 2H), 7.63 (d, J = 8.2 Hz, 2H), 6.49 (s, 2H), 3.85 (s, 3H), 3.77 (s, 3H) | $^{19}$F NMR (376 MHz, DMSO-d$_6$) −141.15 |
| 17 | Yellow Solid | 137-139 | 384 ([M]+) | (400 MHz, CDCl$_3$) 7.23 (dd, J = 7.9, 5.1 Hz, 1H), 7.12 (dd, J = 9.3, 4.0 Hz, 1H), 4.60 (s, 2H), 3.97 (s, 3H), 3.97 (s, 3H), 0.33 (d, J = 0.8 Hz, 9H) | $^{19}$F NMR (376 MHz, CDCl$_3$) −107.12, −121.88, −137.27 |
| 18 | Yellow Solid | 127-129 | 367 ([M + H]+) | (400 MHz, CDCl$_3$) 7.56 (t, J = 7.2 Hz, 1H), 7.37 (dd, J = 7.5, 0.7 Hz, 1H), 7.26 (dd, J = 10.1, 0.8 Hz, 1H), 4.57 (s, 2H), 3.97 (s, 3H), 3.96 (s, 3H), 0.28 (s, 9H) | $^{19}$F NMR (376 MHz, CDCl$_3$) −116.17, −137.36 |
| 19 | White Solid | | 392.06 ([M + H]+) | (400 MHz, DMSO-d$_6$) 7.67 (ddd, J = 8.3, 6.3, 1.7 Hz, 1H), 7.40-7.27 (m, 1H), 6.68 (s, 2H), 3.84 (s, 3H), 3.79 (s, 3H) | $^{19}$F NMR (376 MHz, DMSO-d$_6$) −131.44, −131.45, −131.46, −131.50, −131.50, −131.51, −131.52, −136.12, −136.14, −136.19, −136.20, −136.22, −136.26, −136.28, −138.65, −138.72 |
| 20 | Orange Solid | 116-118 | 391 ([M]+) | (400 MHz, CDCl$_3$) 7.40 (d, J = 6.0, 8.4 Hz, 1H), 7.37 (d, J = 6.0, 8.4 Hz, 1H), 4.62 (s, 2H), 3.98 (s, 3H), 3.97 (s, 3H) | $^{19}$F NMR (376 MHz, CDCl$_3$) −113.12, −117.61, −137.22 |
| 21 | White Solid | | 375 ([M + H]+), 372 ([M − H]−) | (400 MHz, CDCl$_3$) 7.75 (d, J = 9.6 Hz, 1H), 7.65-7.57 (m, 2H), 4.59 (s, 2H), 3.99 (s, 3H), 3.96 (s, 3H) | $^{19}$F NMR (376 MHz, CDCl$_3$) −107.19, −139.83 |

TABLE 2-continued

Analytical Data for Compounds in Table 1

| Compound Number | Appearance | mp (° C.) | ESIMS[1] m/z | $^1$H NMR (field strength, solvent) δ | Other NMR (field strength, solvent) δ |
|---|---|---|---|---|---|
| 22 | Orange Gummy Oil | | 373 ([M]+) | (400 MHz, CDCl$_3$) 7.48 (t, J = 7.8 Hz, 1H), 7.40 (dd, J = 8.3, 1.5 Hz, 1H), 7.34 (dd, J = 9.4, 1.5 Hz, 1H), 4.60 (s, 2H), 3.97 (s, 6H) | $^{19}$F NMR (376 MHz, CDCl$_3$) −111.54, −137.36 |
| 23 | Orange Solid | | 403.61 ([M + H]+) | (400 MHz, DMSO-d$_6$) 7.86 (d, J = 8.5 Hz, 2H), 7.65-7.53 (m, 2H), 6.54 (s, 2H), 3.86 (s, 3H), 3.77 (s, 3H) | $^{19}$F NMR (376 MHz, DMSO-d$_6$) −140.64 |
| 24 | White Solid | | EIMS m/z 439.33 ([M + H]+) | (400 MHz, DMSO-d$_6$) 7.84-7.70 (m, 1H), 7.23-7.12 (m, 1H), 6.66 (s, 2H), 3.84 (s, 3H), 3.78 (s, 3H) | $^{19}$F NMR (376 MHz, DMSO-d$_6$) −119.00, −119.06, −136.73, −136.80, −136.81, −136.87, −138.61, −138.69 |
| 25 | White Solid | 127-129 | 439 ([M + H]+) | (400 MHz, CDCl$_3$) 7.54 (dd, J = 8.5, 5.0 Hz, 1H), 7.32 (dd, J = 7.6, 5.8 Hz, 1H), 4.62 (s, 2H), 3.98 (s, 3H), 3.97 (s, 3H) | $^{19}$F NMR (376 MHz, CDCl$_3$) −100.21, −118.29, −137.17 |
| 26 | Brown Solid | dec | 421 ([M + H]+) | (400 MHz, CDCl$_3$) 7.60 (dd, J = 8.2, 1.6 Hz, 1H), 7.52 (dd, J = 9.2, 1.6 Hz, 1H), 7.32 (t, J = 7.8 Hz, 1H), 4.59 (s, 2H), 3.97 (s, 6H) | $^{19}$F NMR (376 MHz, CDCl$_3$) −111.86, −137.30 |
| 27 | Sticky Orange Solid | | 421 ([M + H]+), 420 ([M − H]−) | (400 MHz, CDCl$_3$) 7.82 (dd, J = 8.3, 6.5 Hz, 1H), 7.68 (ddd, J = 9.3, 1.9, 1.1 Hz, 1H), 7.50 (dt, J = 8.3, 1.7 Hz, 1H), 4.60 (s, 2H), 3.99 (s, 3H), 3.96 (s, 3H) | $^{19}$F NMR (376 MHz, CDCl$_3$) −93.82, −139.71 |
| 28 | Off-White Solid | 145-147 | 425.22 ([M + H]+) | (400 MHz, DMSO-d$_6$) 13.15 (s, 1H), 7.86-7.71 (m, 1H), 7.21 (ddd, J = 8.3, 6.5, 1.7 Hz, 1H), 6.59 (s, 2H), 3.79 (s, 3H) | $^{19}$F NMR (376 MHz, DMSO-d$_6$) −119.08, −119.14, −136.61, −136.67, −136.69, −136.75, −139.25, −139.33 |
| 29 | Tan Solid | | 305 ([M + H]+), 303 ([M − H]−) | (400 MHz, CDCl$_3$) 10.08 (s, 1H), 8.09 (dd, J = 8.3, 1.5 Hz, 2H), 8.03-7.93 (m, 2H), 4.62 (s, 2H), 4.00 (s, 3H), 3.98 (s, 3H) | $^{19}$F NMR (376 MHz, CDCl$_3$) −139.69 |
| 30 | Off-White Solid | | 301 ([M + H]+), 299 ([M − H]−) | (400 MHz, CDCl$_3$) 7.93-7.85 (m, 2H), 7.62-7.53 (m, 2H), 4.57 (s, 2H), 3.98 (s, 3H), 3.96 (s, 3H), 3.15 (s, 1H) | $^{19}$F NMR (376 MHz, CDCl$_3$) −139.97 |
| 31 | Tan Solid | 93-94 | 311 ([M + H]+), 309 ([M − H]−) | (400 MHz, acetone-d$_6$) 7.96 (dd, J = 8.8, 1.4 Hz, 1H), 7.57-7.49 (m, 1H), 5.93 (s, 1H), 3.92 (s, 1H), 3.91 (s, 1H) | |
| 32 | Pinkish Solid | 109-110 | EIMS m/z 328 | (400 MHz, acetone-d$_6$) 7.93-7.78 (m, 2H), 7.72-7.61 (m, 1H), 5.99 (s, 1H), 3.93 (s, 3H), 3.92 (s, 3H) | |
| 33 | Sticky Brown-Orange Solid | | 375 ([M + H]+), 373 ([M − H]−) | (400 MHz, CDCl$_3$) 7.53-7.46 (m, 1H), 7.29 (dt, J = 8.4, 1.1 Hz, 1H), 6.39-6.03 (m, 1H), 4.61 (s, 2H), 3.97 (d, J = 2.1 Hz, 6H), 1.85-1.68 (m, 3H) | $^{19}$F NMR (376 MHz, CDCl$_3$) −113.81, −113.87, −113.90, −113.95, −137.05, −137.14, −175.47, −175.52 |
| 34 | Off-White Solid | 133.5-135.5 | 360 ([M + H]+), 358 ([M − H]−) | (400 MHz, CDCl$_3$) 7.27-7.21 (m, 2H), 4.60 (s, 2H), 3.98-3.97 (m, 9H) | $^{19}$F NMR (376 MHz, CDCl$_3$) −128.8, −137.4 |
| 35 | Off-White Solid | 97-99 | 343.24 ([M − H]−) | (400 MHz, CDCl$_3$) 8.03 (d, J = 8.1 Hz, 2H), 7.76-7.66 (m, 2H), 4.61 (s, 2H), 3.99 (s, 3H), 3.97 (d, J = 3.5 Hz, 3H) | $^{19}$F NMR (376 MHz, CDCl$_3$) −62.71, −140.31 |
| 36 | White Solid | 141-143 | 295.49 ([M + H]+), | (400 MHz, DMSO-d$_6$) 7.92-7.75 (m, 2H), 7.32 | $^{19}$F NMR (376 MHz, DMSO-d$_6$) |

TABLE 2-continued

Analytical Data for Compounds in Table 1

| Compound Number | Appearance | mp (° C.) | ESIMS[1] m/z | $^1$H NMR (field strength, solvent) δ | Other NMR (field strength, solvent) δ |
|---|---|---|---|---|---|
| | | | 293.04 ([M − H]−) | (t, J = 8.9 Hz, 2H), 6.52 (s, 2H), 3.86 (s, 3H), 3.77 (s, 3H) | −112.76, −141.18 |
| 37 | Off-White Solid | 110-112 | 321.1 ([M + H]+) | (400 MHz, DMSO-d$_6$) 7.38-7.25 (m, 2H), 7.02 (d, J = 8.1 Hz, 1H), 6.45 (s, 2H), 6.09 (s, 2H), 3.85 (s, 3H), 3.76 (s, 3H) | $^{19}$F NMR (376 MHz, DMSO-d$_6$) −140.87 |
| 38 | White Solid | 139-141 | 379.57 ([M + H]+), 377.49 ([M − H]−) | (400 MHz, DMSO-d$_6$) 7.75 (t, J = 7.2 Hz, 1H), 7.60 (t, J = 7.2 Hz, 1H), 6.75 (s, 2H), 3.85 (s, 3H), 3.80 (s, 3H) | $^{19}$F NMR (376 MHz, DMSO-d$_6$) −59.83 (d, J = 12.5 Hz), −136.46- −138.21 (m), −138.55 (d, J = 28.4 Hz), −140.24--141.37 (m) |
| 39 | Pink Solid | 120-123 | 347 ([M + H]+), 346 ([M − H]−) | (400 MHz, CDCl$_3$) 7.42 (dd, J = 8.9, 6.1 Hz, 1H), 7.23 (dd, J = 8.8, 6.0 Hz, 1H), 4.63 (s, 2H), 3.98 (m, 6H) | $^{19}$F NMR (376 MHz, CDCl$_3$) −117.4, −120.8, −137.2 |
| 40 | White Solid | 130-132 | 344 ([M − H]−) | (400 MHz, CDCl$_3$) 9.25 (s, 1H), 8.43 (d, J = 8.2 Hz, 1H), 7.78 (d, J = 8.2 Hz, 1H), 4.67 (s, 2H), 4.00 (s, 3H), 3.98 (s, 3H) | $^{19}$F NMR (376 MHz, CDCl$_3$) −67.96, −140.19, −140.20, −140.21 |
| 41 | Yellow-Orange Solid | | 302 ([M + H]+), 300 ([M − H]−) | (400 MHz, CDCl$_3$) 8.08- 8.00 (m, 2H), 7.78- 7.69 (m, 2H), 4.62 (s, 2H), 3.99 (s, 3H), 3.97 (s, 3H) | $^{19}$F NMR (376 MHz, CDCl$_3$) −139.91 |
| 42 | Tan Solid | | 339 ([M + H]+), 337 ([M − H]−) | (400 MHz, CDCl$_3$) 7.07 (dd, J = 8.2, 6.4 Hz, 1H), 6.75 (dd, J = 8.2, 0.6 Hz, 1H), 6.08 (s, 2H), 4.56 (s, 2H), 3.97 (s, 3H), 3.96 (s, 3H) | $^{19}$F NMR (376 MHz, CDCl$_3$) −137.74, −139.47 |
| 43 | Brown Solid | 113-115 | 372.44 ([M + H]+), 370.49 ([M − H]−) | (400 MHz, DMSO-d$_6$) 7.38 (dd, J = 8.4, 1.3 Hz, 1H), 7.22 (dd, J = 8.4, 7.3 Hz, 1H), 6.58 (s, 2H), 3.84 (s, 3H), 3.78 (s, 3H) | $^{19}$F NMR (376 MHz, DMSO-d$_6$) −120.48, −120.55, −138.35, −138.42 |
| 44 | White Solid | 139-141 | 326.00 ([M − H]−) | (400 MHz, DMSO-d$_6$) 7.60-7.54 (m, 2H), 7.54- 7.47 (m, 2H), 6.68 (s, 2H), 3.84 (s, 3H), 3.77 (s, 3H) | |
| 45 | White Solid | 143-146 | 345 ([M + H]+), 343 ([M − H]−) | (400 MHz, CDCl$_3$) 7.30 (dd, J = 8.5, 1.6 Hz, 1H), 7.19 (dd, J = 8.4, 6.8 Hz, 1H), 4.83 (s, 2H), 4.07 (s, 3H), 4.02 (d, J = 1.1 Hz, 3H) | $^{19}$F NMR (376 MHz, CDCl$_3$) −128.66, −128.74, −134.93, −135.01 |
| 46 | Off-white Solid | 165 | 279 ([M + H]+), 277 ([M − H]−) | (300 MHz, DMSO-d$_6$) 7.88 (m, 2H), 7.48 (d, J = 8.5 Hz, 2H), 7.18 (s, 1H), 6.30 (s, 2H), 3.70 (s, 3H) | |
| 47 | White Solid | | 297 ([M + H]+), 295 ([M − H]−) | (400 MHz, DMSO-d$_6$) 13.06 (s, 1H), 7.86 (dd, J = 8.6, 1.3 Hz, 2H), 7.59- 7.51 (m, 2H), 6.46 (s, 2H), 3.78 (d, J = 5.5 Hz, 3H) | |
| 48 | Off-White Solid | 151 | 333 ([M + H]+), 331 ([M − H]−) | (400 MHz, acetone-d$_6$) 7.58-7.48 (m, 2H), 6.22 (s, 1H), 3.97 (s, 3H) | |
| 49 | Off-White Solid | 137 | 315 ([M + H]+), 313 ([M − H]−) | (400 MHz, DMSO-d$_6$) 7.89-7.82 (m, 1H), 7.72 (d, J = 4.9 Hz, 1H), 6.57 (s, 1H), 3.78 (s, 3H) | |
| 50 | White Solid | 135-137 | 330.234 ([M + H]+), 329.98 ([M − H]−) | (400 MHz, CDCl$_3$) 7.97 (d, J = 8.1 Hz, 2H), 7.77 (d, J = 8.2 Hz, 2H), 4.86 (s, 2H), 4.07 (s, 3H), 1.67 (s, 1H) | $^{19}$F NMR (376 MHz, CDCl$_3$) −62.81, −137.90 |
| 51 | Off-White Solid | | 221.46 ([M + H]+) | (400 MHz, DMSO-d$_6$) 13.22 (d, J = 68.3 Hz, 1H), 6.75 (s, 2H), 3.74 (s, 3H) | $^{19}$F NMR (376 MHz, DMSO-d$_6$) −137.53 (s) |
| 52 | Off-White Solid | 149-151 | 281.8 ([M + H]+), | (400 MHz, DMSO-d$_6$) 12.97 (s, 1H), 7.88 (dd, J = | $^{19}$F NMR (376 MHz, DMSO-d$_6$) |

TABLE 2-continued

Analytical Data for Compounds in Table 1

| Compound Number | Appearance | mp (° C.) | ESIMS[1] m/z | $^1$H NMR (field strength, solvent) δ | Other NMR (field strength, solvent) δ |
|---|---|---|---|---|---|
| 53 | White Solid | 223-225 | 279.7 ([M − H]−) 308.1 ([M + H]+) | 7.6, 5.7 Hz, 2H), 6.45 (s, 2H), 3.78 (s, 3H) (400 MHz, DMSO-d6) 7.32 (d, J = 9.0 Hz, 2H), 6.97 (d, J = 7.9 Hz, 1H), 6.06 (s, 2H), 5.70 (s, 2H), 3.74 (s, 3H) | −112.85, −141.74 $^{19}$F NMR (376 MHz, DMSO-d6) −147.68 |
| 54 | White Solid |  | 375.98 ([M − H]−) | (400 MHz, DMSO-d6) 7.67 (ddd, J = 8.3, 6.3, 1.7 Hz, 1H), 7.37 (ddd, J = 8.6, 6.9, 1.9 Hz, 1H), 6.56 (s, 2H), 3.79 (s, 3H), 3.37 (s, 2H) | $^{19}$F NMR (376 MHz, DMSO-d6) −131.62 (ddd, J = 22.9, 6.3, 1.7 Hz), −135.83- −136.35 (m), −139.80 (d, J = 27.9 Hz) |
| 55 | Orange Solid |  | 387.87 ([M − H]−) | (400 MHz, DMSO-d6) 12.99 (d, J = 70.4 Hz, 1H), 7.96-7.77 (m, 2H), 7.71-7.54 (m, 2H), 6.46 (s, 2H), 3.77 (s, 3H) | $^{19}$F NMR (376 MHz, DMSO-d6) −141.18 (s) |
| 56 | White Solid | 133-135 | 367.2 ([M + H]+) | (400 MHz, DMSO-d6) 13.14 (d, J = 72.7 Hz, 1H), 7.76 (t, J = 7.2 Hz, 1H), 7.61 (dd, J = 19.3, 11.7 Hz, 1H), 6.66 (s, 2H), 3.80 (s, 3H) | $^{19}$F NMR (376 MHz, DMSO-d6) −59.81 (d, J = 12.6 Hz), −137.11- −138.15 (m), −139.22 (d, J = 29.8 Hz), −140.65 (dt, J = 25.2, 12.5 Hz) |
| 57 | White Solid | 153.5-155.0 | 333 ([M + H]+), 331 ([M − H]−) | (400 MHz, CDCl3) 7.36 (dd, J = 8.7, 6.0 Hz, 1H), 7.30 (dd, J = 9.0, 5.9 Hz, 1H), 4.86 (s, 2H), 4.07 (s, 3H) | $^{19}$F NMR (376 MHz, CDCl3) −117.2, −120.2, −135.0 |
| 58 | White Solid | 148.5-150.5 | 215 ([M + H]+) | (400 MHz, DMSO-d6) 6.26 (s, 2H), 3.71 (s, 3H), 2.64 (qd, J = 7.6, 2.6 Hz, 2H), 1.15 (t, J = 7.6 Hz, 3H) | $^{19}$F NMR (376 MHz, DMSO-d6) −139.6 |
| 59 | Yellow Solid | 147-148 | 376 ([M − H]−) | (400 MHz, DMSO-d6) 7.88 (dd, J = 9.0, 5.7 Hz, 1H), 7.59 (dd, J = 8.7, 6.1 Hz, 1H), 6.58 (s, 2H), 3.78 (s, 3H) | $^{19}$F NMR (376 MHz, DMSO-d6) −113.74, −117.64, −138.88 |
| 60 | White Solid | 132-134 | 425 ([M + H]+) | (400 MHz, DMSO-d6) 7.91 (dd, J = 8.8, 5.1 Hz, 1H), 7.44 (dd, J = 8.0, 5.9 Hz, 1H), 6.57 (s, 2H), 3.78 (s, 3H) | $^{19}$F NMR (376 MHz, DMSO-d6) −101.29, −118.82, −138.86 |
| 61 | Light Brown Solid | dec | 359 ([M]+) | (400 MHz, DMSO-d6) 7.69 (d, J = 9.8 Hz, 1H), 7.58-7.47 (m, 2H), 6.54 (s, 2H), 3.78 (s, 3H) | $^{19}$F NMR (376 MHz, DMSO-d6) −111.91, −139.22 |
| 62 | Light Brown Solid | 143-145 | 407 ([M + H]+) | (400 MHz, DMSO-d6) 7.79 (dd, J = 9.6, 1.6 Hz, 1H), 7.72 (dd, J = 8.1, 1.6 Hz, 1H), 7.33 (t, J = 7.9 Hz, 1H), 6.53 (s, 2H), 3.78 (s, 3H) | $^{19}$F NMR (376 MHz, DMSO-d6) −112.65, −139.16 |
| 63 | White Solid | 160-162 | 332 ([M + H]+), 330 ([M − H]−) | (400 MHz, DMSO-d6) 13.19 (s, 1H), 9.17 (s, 1H), 8.49 (d, J = 8.2 Hz, 1H), 8.05 (d, J = 8.2 Hz, 1H), 6.63 (s, 2H), 3.80 (s, 3H) | $^{19}$F NMR (376 MHz, DMSO-d6) −66.41, −141.10 |
| 64 | White Solid | 169-171 | 363 ([M + H]+) | (300 MHz, DMSO-d6) 7.62-7.53 (m, 1H), 7.42 (dd, J = 8.7, 1.6 Hz, 1H), 7.16 (d, J = 1.8 Hz, 1H), 7.02 (t, J = 73.4 Hz, 1H), 6.70 (s, 2H), 3.92 (d, J = 0.8 Hz, 3H) |  |
| 65 | Brown Solid |  | 361 ([M + H]+), 359 ([M − H]−) | (400 MHz, DMSO-d6) 7.58 (t, J = 7.8 Hz, 1H), 7.50 (d, J = 8.4 Hz, 1H), 6.56 (s, 2H), 6.17 (dq, J = 19.8, 6.4 Hz, 1H), 3.79 (s, 3H), 1.73 (dd, J = 23.1, 6.6 Hz, 3H) | $^{19}$F NMR (376 MHz, DMSO-d6) −114.32, −114.37, −114.39, −114.44, −139.01, −139.09, −172.70, −172.75 |
| 66 | White Solid | 118 | 436 ([M + H]+), 434 | (400 MHz, acetone-d6) 7.56-7.49 (m, 2H), 7.43-7.27 (m, 5H), 5.98 (s, |  |

TABLE 2-continued

Analytical Data for Compounds in Table 1

| Compound Number | Appearance | mp (° C.) | ESIMS[1] m/z | $^1$H NMR (field strength, solvent) δ | Other NMR (field strength, solvent) δ |
|---|---|---|---|---|---|
| | | | | ([M − H]−) 2H), 5.40 (s, 2H), 3.97 (d, J = 1.1 Hz, 3H), 3.85 (s, 3H) | |
| 67 | Off-White Solid | 123-125 | 393 ([M + H]+), 391 ([M − H]−) | (300 MHz, CDCl$_3$) 8.00 (t, J = 8.5 Hz, 1H), 7.23 (m, 3H), 7.15 (dd, 7 = 11.1, 2.0 Hz, 1H), 4.59 (s, 2H), 4.46 (m, 4H), 1.44 (t, J = 7.1 Hz, 3H) | |
| 68 | Tan Solid | | | (300 MHz, CDCl$_3$) 7.99 (dd, J = 11.9, 5.1 Hz, 1H), 7.25-7.11 (m, 3H), 6.13 (tt, J = 55.0, 3.9 Hz, 1H), 4.74 (d, J = 80.7 Hz, 2H), 4.47 (tt, J = 12.3, 6.2 Hz, 2H), 4.27 (td, J = 13.9, 3.9 Hz, 2H), 1.44 (t, J = 7.1 Hz, 3H) | |
| 69 | Off-White Semi-Solid | | 329.0 ([M + H]+) | (400 MHz, DMSO-d$_6$) 7.62-7.51 (m, 2H), 7.42 (dd, J = 8.3, 1.9 Hz, 1H), 6.60 (s, 2H), 3.84 (s, 3H), 3.78 (s, 3H) | $^{19}$F NMR (376 MHz, DMSO-d$_6$) −112.06, −112.14, −138.59, −138.67 |
| 70 | Slight Brown Solid | | 365 ([M + H]+), 363 ([M − H]−) | (300 MHz, DMSO-d$_6$) 7.95 (t, J = 8.6 Hz, 1H), 7.55 (dd, J = 11.3, 2.0 Hz, 1H), 7.40 (dd, J = 8.5, 2.0 Hz, 1H), 7.24 (d, 7 = 1.9 Hz, 1H), 6.34 (s, 2H), 4.56 (q, J = 9.0 Hz, 2H) | |
| 71 | White Solid | | 315.47 ([M + H]+), 313.99 ([M − H]−) | (400 MHz, CDCl$_3$) 7.62-7.54 (m, 2H), 7.42 (dd, J = 8.2, 2.0 Hz, 1H), 6.53 (s, 2H), 3.78 (s, 3H) | $^{19}$F NMR (376 MHz, CDCl$_3$) −107.18, −107.26, −134.44, −134.52 |
| 72 | Off-White Solid | 168-170 | 331 ([M + H]+) | (400 MHz, DMSO) δ 13.38 (s, 1H), 7.81 (d, J = 11.1 Hz, 1H), 7.73 (s, 2H), 6.92 (s, 2H), 2.26 (s, 3H) | $^{19}$F NMR (376 MHz, DMSO) δ −115.93, −143.45 |
| 73 | White Solid | 176-178 | 237 ([M + H]+), 235 ([M − H]−) | (400 MHz, DMSO) δ 13.58 (s, 1H), 7.13 (s, 1H), 2.23 (s, 2H) | $^{19}$F NMR (376 MHz, DMSO) δ −140.08 |
| 74 | White Solid | 75-77 | EIMS m/z 250 | (400 MHz, CDCl3) δ 5.35 (s, 2H), 3.96 (s, 3H), 2.33 (s, 3H) | $^{19}$F NMR (376 MHz, CDCl3) δ −138.81 |
| 75 | | | 308 ([M + H]+) | (400 MHz, DMSO-d6) δ 3.77 (s, 3H), 3.86 (s, 3H), 3.92 (s, 3H), 6.53 (s, 2H), 6.95 (dd, J = 8.6, 0.8 Hz, 1H), 8.10 (ddd, J = 8.6, 2.4, 1.1 Hz, 1H), 8.58 (t, J = 2.0 Hz, 1H) | $^{19}$F NMR (376 MHz, DMSO-d6) δ −141.20 |
| 76 | | | 318 ([M + H]+) | (400 MHz, DMSO-d6) δ 0.99 (tt, J = 7.6, 2.7 Hz, 4H), 2.17 (tt, J = 7.8, 5.1 Hz, 1H), 3.77 (s, 3H), 3.86 (s, 3H), 6.55 (s, 2H), 7.42 (d, J = 8.9 Hz, 1H), 8.00 (ddd, J = 8.2, 2.3, 1.2 Hz, 1H), 8.77 (t, J = 2.0 Hz, 1H) | $^{19}$F NMR (376 MHz, DMSO-d6) δ −141.19 |
| 77 | | | 304 ([M + H]+) | (400 MHz, DMSO-d6) δ 0.92-1.06 (m, 4H), 2.17 (tt, J = 7.8, 5.1 Hz, 1H), 3.78 (s, 3H), 6.49 (s, 2H), 7.42 (dd, J = 8.3, 0.9 Hz, 1H), 8.05 (ddd, J = 8.2, 2.2, 1.1 Hz, 1H), 8.81 (t, J = 2.0 Hz, 1H), 13.03 (s, 1H) | $^{19}$F NMR (376 MHz, DMSO-d6) δ −141.73 |
| 78 | | | 294 ([M + H]+) | (400 MHz, DMSO-d6) δ 3.78 (s, 3H), 3.92 (s, 3H), 6.47 (s, 2H), 6.95 (dd, J = 8.7, 0.8 Hz, 1H), 8.15 (ddd, J = 8.7, 2.4, 1.1 Hz, | $^{19}$F NMR (376 MHz, DMSO-d6) δ −141.78 |

TABLE 2-continued

Analytical Data for Compounds in Table 1

| Compound Number | Appearance | mp (° C.) | ESIMS[1] m/z | $^1$H NMR (field strength, solvent) δ | Other NMR (field strength, solvent) δ |
|---|---|---|---|---|---|
| 79 | | | 331 ([M + H]+) | 1H), 8.61 (t, J = 2.1 Hz, 1H), 13.02 (s, 1H) (400 MHz, DMSO-d6) δ 3.78 (s, 3H), 6.54 (s, 2H), 7.76 (d, J = 8.5 Hz, 1H), 7.84 (dt, J = 8.5, 1.7 Hz, 1H), 8.07 (d, J = 1.8 Hz, 1H), 13.10 (s, 1H) | $^{19}$F NMR (376 MHz, DMSO-d6) δ −140.72 |
| 80 | | | 331 ([M + H]+) | (400 MHz, DMSO-d6) δ 3.78 (s, 3H), 3.87 (s, 3H), 6.61 (s, 2H), 7.70-7.88 (m, 2H), 7.95-8.05 (m, 1H) | $^{19}$F NMR (376 MHz, DMSO-d6) δ −140.26 |
| 81 | Orange Oil | | 245 ([M − H]−) | (400 MHz, CDCl$_3$) δ 7.06 (s, 1H), 4.59 (s, 2H), 3.97 (s, 3H), 3.88 (s, 3H), 1.98 (t, J = 18.7 Hz, 3H) | $^{19}$F NMR (376 MHz, CDCl3) δ −89.99 |
| 82 | Orange Oil | | 231 ([M − H]−) | (400 MHz, DMSO) δ 6.99 (s, 1H), 6.50 (s, 2H), 3.70 (s, 3H), 1.89 (t, J = 19.1 Hz, 3H) | $^{19}$F NMR (376 MHz, DMSO) δ −87.92 |
| 83 | White Solid | | 227 ([M − H]−) | (400 MHz, CDCl$_3$) δ 6.91 (s, 1H), 5.59 (dq, J = 47.6, 6.3 Hz, 1H), 4.53 (s, 2H), 3.97 (s, 3H), 3.87 (s, 3H), 1.62 (dd, J = 24.6, 6.4 Hz, 3H) | $^{19}$F NMR (376 MHz, CDCl3) δ −176.20 |
| 84 | Orange Solid | | 213 ([M − H]−) | (400 MHz, DMSO) δ 9.06 (s, 1H), 6.82 (s, 1H), 6.47 (s, 2H), 5.49 (dq, J = 47.7, 6.3 Hz, 1H), 3.69 (s, 3H), 2.51 (d, J = 24.0 Hz, 1H), 1.52 (dd, J = 24.5, 6.4 Hz, 3H) | $^{19}$F NMR (376 MHz, DMSO) δ −171.64 |
| 85 | Yellow Oil | | EIMS m/z 208 | $^1$H NMR (400 MHz, CDCl$_3$) δ 6.86 (s, 1H), 6.71 (dd, J = 17.6, 10.9 Hz, 1H), 5.98 (dd, J = 17.6, 1.0 Hz, 1H), 5.42 (dd, J = 10.9, 1.0 Hz, 1H), 4.45 (s, 2H), 3.97 (s, 3H), 3.87 (s, 3H) | $^{13}$C NMR (101 MHz, CDCl3) δ 165.94, 152.06, 148.02, 143.34, 141.60, 136.73, 118.02, 108.63, 61.49, 52.84 |
| 86 | Brown Solid | 178-200 | 292 ([M + H]+) | (300 MHz, CDCl$_3$) δ 7.88 (d, J = 8.4 Hz, 1H), 7.39 (d, J = 8.5 Hz, 1H), 6.95 (s, 1H), 5.39 (s, 1H), 4.07 (s, 1H), 3.98 (s, 1H), 2.98 (d, J = 5.1 Hz, 1H) | |
| 87 | Brown Solid | 153-154 | 306 ([M + H]+) | (300 MHz, CDCl$_3$) δ 7.85 (d, J = 8.5 Hz, 2H), 7.39 (d, J = 8.7 Hz, 2H), 7.34 (s, 1H), 6.06 (s, 2H), 3.98 (s, 3H), 2.79 (s, 6H) | |
| 88 | Brown Solid | 93-94 | 369 ([M − H]−) | (300 MHz, CDCl$_3$) δ 7.67 (dd, J = 8.6, 7.7 Hz, 1H), 7.22 (m, 1H), 7.11 (d, J = 1.9 Hz, 1H), 5.16 (s, 2H), 4.47 (q, J = 7.1 Hz, 2H), 3.96 (d, J = 0.9 Hz, 3H), 2.30 (d, J = 1.7 Hz, 3H), 1.43 (t, J = 7.1 Hz, 3H) | |
| 89 | Yellow Solid | | 409 ([M + H]+), 407 ([M − H]−) | (400 MHz, CDCl$_3$) δ 8.02 (m, 1H), 7.23 (m, 1H), 7.16 (m, 16H), 5.20 (s, 2H), 4.48 (q, J = 7.1 Hz, 2H), 3.42 (q, J = 10.0 Hz, 2H), 1.44 (t, J = 7.1 Hz, 3H) | $^{19}$F NMR (376 MHz, CDCl$_3$) δ −66.36, −113.57 |
| 91 | | | 425 ([M + H]+), 423 ([M − H]−) | (400 MHz, CDCl3) δ 7.77-7.84 (m, 1H), 7.68-7.77 (m, 2H), 6.80 (s, 2H), 3.88 (s, 3H) | $^{19}$F NMR (376 MHz, DMSO-d6) δ −140.15, −115.85. |

TABLE 2-continued

Analytical Data for Compounds in Table 1

| Compound Number | Appearance | mp (° C.) | ESIMS[1] m/z | $^1$H NMR (field strength, solvent) δ | Other NMR (field strength, solvent) δ |
|---|---|---|---|---|---|
| 92 | White Solid | | 233 ([M + H]+) | (400 MHz, CDCl$_3$) δ 7.06 (s, 1H), 6.54 (t, J = 55.4 Hz, 1H), 4.69 (s, 2H), 3.98 (s, 3H), 3.90 (s, 3H) | $^{19}$F NMR (376 MHz, CDCl3) δ −114.65 |
| 93 | White Solid | 125-126 | 345 ([M + H]$^+$), 343 ([M − H]$^−$) | (400 MHz, CDCl3) δ 7.77 (dd, J = 28.9, 9.5 Hz, 2H), 7.47 (m, 1H), 5.28 (s, 2H), 3.99 (s, 3H), 2.35 (s, 3H) | $^{19}$F NMR (376 MHz, CDCl3) δ −115.10, −143.40 |
| 94 | White Solid | 113-117 | 375 ([M + H]$^+$), 373 ([M − H]$^−$) | (400 MHz, CDCl$_3$) δ 7.27-7.24 (m, 2H), 5.31 (s, 2H), 3.98 (d, J = 1.1 Hz, 3H), 3.96 (s, 3H), 2.32 (s, 3H) | $^{19}$F NMR (376 MHz, CDCl3) δ −127.97, −128.06, −140.43, −140.52 |
| 95 | Tan Solid | | 213 ([M + H]$^+$) | (400 MHz, DMSO-d$_6$) δ 3.73 (s, 3H), 5.50 (dd, J = 11.0, 2.2 Hz, 1H), 6.20 (dd, J = 17.3, 2.2 Hz, 1H), 6.35 (s, 2H), 6.83 (ddd, 7 = 17.3, 10.9, 1.7 Hz, 1H), 12.98 (s, 1H). | $^{19}$F NMR (376 MHz, DMSO-d$_6$) δ −145.09. |

[1]Unless otherwise stated, the mass spectrometry data are electrospray ionization mass spectrometry (ESIMS).

Example 69

Preparation of Herbicidal Compositions

In the following illustrative compositions, parts and percentages are by weight (wt %).

Emulsifiable Concentrates

| Formulation A | WT % |
|---|---|
| Compound 12 | 26.2 |
| Polyglycol 26-3 | 5.2 |
| Nonionic emulsifier-(di-sec-butyl)phenylpoly(oxypropylene)block polymer with oxyethylene). The polyoxyethelene content is about 12 moles. | |
| Witconate P12-20 (Anionic emulsifier-calcium dodecylbenzene sulfonate-60 wt. % active) | 5.2 |
| Aromatic 100 (Xylene range aromatic solvent) | 63.4 |

| Formulation B | WT % |
|---|---|
| Compound 66 | 3.5 |
| Sunspray 11N (paraffin oil) | 40.0 |
| Polyglycol 26-3 | 19.0 |
| Oleic acid | 1.0 |
| Xylene range aromatic solvent | 36.5 |

| Formulation C | WT % |
|---|---|
| Compound 68 | 13.2 |
| Stepon C-65 | 25.7 |
| Ethomeen T/25 | 7.7 |
| Ethomeen T/15 | 18.0 |
| Xylene range aromatic solvent | 35.4 |

These concentrates can be diluted with water to give emulsions of suitable concentrations for controlling weeds.

Wettable Powders

| Formulation D | WT % |
|---|---|
| Compound 46 | 26.0 |
| Polyglycol 26-3 | 2.0 |
| Polyfon H | 4.0 |
| Zeosyl 100 (Precipitated hydrated SiO$_2$) | 17.0 |
| Barden clay + inerts | 51.0 |

| Formulation E | WT % |
|---|---|
| Compound 55 | 62.4 |
| Polyfon H (sodium salt of lignin sulfonate) | 6.0 |
| Sellogen HR (sodium naphthalene sulfonate) | 4.0 |
| Zeosyl 100 | 27.6 |

The active ingredient is applied to the corresponding carriers and then these are mixed and ground to yield wettable powders of excellent wettability and suspension power. By diluting these wettable powders with water it is possible to obtain suspensions of suitable concentrations for controlling weeds.

Water Dispersible Granules

| Formulation F | WT % |
|---|---|
| Compound 48 | 26.0 |
| Sellogen HR | 4.0 |
| Polyfon H | 5.0 |
| Zeosyl 100 | 17.0 |
| Kaolinite clay | 48.0 |

The active ingredient is added to the hydrated silica, which is then mixed with the other ingredients and ground to a powder. The powder is agglomerated with water and sieved to provide granules in the range of −10 to +60 mesh. By dispersing these granules in water it is possible to obtain suspensions of suitable concentrations for controlling weeds.

Granules

Formulation G

|  | WT % |
|---|---|
| Compound 58 | 5.0 |
| Celetom MP-88 | 95.0 |

The active ingredient is applied in a polar solvent such as N-methyl pyrrolidinone, cyclohexanone, gamma-butyrolactone, etc. to the Celetom MP 88 carrier or to other suitable carriers. The resulting granules can be applied by hand, granule applicator, airplane, etc. in order to control weeds.

Formulation H

|  | WT % |
|---|---|
| Compound 28 | 1.0 |
| Polyfon H | 8.0 |
| Nekal BA 77 | 2.0 |
| Zinc Stearate | 2.0 |
| Barden Clay | 87.0 |

All materials are blended and ground to a powder, then water is added and the clay mixture is stirred until a paste is formed. The mixture is extruded through a die to provide granules of proper size.

Example 70

Evaluation of Postemergent Herbicidal Activity

Post-Emergent Test I:

Seeds or nutlets of the desired test plant species were planted in Sun Gro Metro-Mix® 360 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7-21 d in a greenhouse with an approximate 15 h photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 25 mL glass vial and was dissolved in 4 mL of a 97:3 v/v mixture of acetone and DMSO to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of 97:3 v/v mixture of acetone and DMSO and 10 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain ½X, ¼X, ⅛X and 1/16X rates of the high rate. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by subirrigation to prevent wash-off of the test compounds. After 14 d, the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Table 3 and Table 8.

TABLE 3

Post-emergent Test I Herbicidal Activity

| Compound Number | Application Rate (g ai/ha) | Visual Growth Reduction (%) - 14 Days after Application | | | | | | |
|---|---|---|---|---|---|---|---|---|
|  |  | ABUTH | CHEAL | EPHHL | ECHCG | CYPES | ORYSA | ZEAMX |
| 1 | 280 | 100 | 100 | 100 | 0 | 0 | 0 | 0 |
| 2 | 280 | 90 | 90 | 95 | 0 | 0 | 0 | 0 |
| 3 | 140 | 100 | 100 | 100 | 0 | 0 | 0 | 10 |
| 4 | 140 | 80 | 100 | 100 | 0 | 0 | 0 | 0 |
| 5 | 70 | 100 | 100 | 100 | 80 | 20 | 0 | 60 |
| 6 | 140 | 60 | 100 | 100 | 0 | 20 | 5 | 0 |
| 7 | 140 | 90 | 100 | 95 | 0 | 0 | 0 | 0 |
| 8 | 280 | 25 | 30 | 90 | 0 | 0 | 0 | 0 |
| 10 | 280 | 100 | 100 | 100 | 0 | 0 | 0 | 25 |
| 11 | 140 | 100 | 100 | 100 | 100 | 50 | 12 | 80 |
| 12 | 280 | 0 | 70 | 0 | 0 | 0 | 0 | 0 |
| 13 | 280 | 0 | 90 | 70 | 0 | 0 | 0 | 0 |
| 19 | 70 | 85 | 100 | 100 | 75 | 90 | 0 | 70 |
| 20 | 70 | 85 | 100 | 100 | 80 | 50 | 0 | 80 |

TABLE 3-continued

Post-emergent Test I Herbicidal Activity

| Compound Number | Application Rate (g ai/ha) | Visual Growth Reduction (%) - 14 Days after Application | | | | | | |
|---|---|---|---|---|---|---|---|---|
| | | ABUTH | CHEAL | EPHHL | ECHCG | CYPES | ORYSA | ZEAMX |
| 21 | 70 | 85 | 100 | 100 | 50 | 70 | 0 | 50 |
| 22 | 140 | 60 | 100 | 100 | 90 | 50 | 0 | 70 |
| 23 | 140 | 70 | 100 | 100 | 80 | 100 | 0 | 70 |
| 24 | 140 | 60 | 65 | 100 | 50 | 100 | 0 | 75 |
| 25 | 140 | 70 | 90 | 100 | 85 | 100 | 0 | 70 |
| 26 | 140 | 10 | 90 | 100 | 55 | 50 | 0 | 75 |
| 27 | 140 | 60 | 90 | 100 | 60 | 100 | 0 | 70 |
| 28 | 70 | 70 | 100 | 100 | 80 | 40 | 5 | 70 |
| 30 | 140 | 50 | 100 | 100 | 0 | 100 | 0 | 70 |
| 31 | 140 | 100 | 100 | 100 | 95 | 100 | 15 | 85 |
| 32 | 140 | 95 | 100 | 100 | 90 | 100 | 0 | 75 |
| 33 | 140 | 100 | 100 | 100 | 80 | 100 | 0 | 70 |
| 34 | 140 | 100 | 100 | 100 | 100 | 100 | 10 | 90 |
| 35 | 140 | 75 | 100 | 100 | 80 | 100 | 0 | 70 |
| 36 | 140 | 100 | 100 | 100 | 0 | 100 | 0 | 60 |
| 37 | 140 | 55 | 100 | 100 | 100 | 100 | 0 | 75 |
| 38 | 140 | 85 | 90 | 100 | 10 | 50 | 0 | 75 |
| 39 | 70 | 80 | 100 | 100 | 80 | 100 | 0 | 75 |
| 40 | 140 | 80 | 100 | 100 | 50 | 100 | 0 | 70 |
| 41 | 140 | 80 | 100 | 100 | 0 | 100 | 0 | 70 |
| 42 | 140 | 60 | 90 | 100 | 0 | 10 | 0 | 75 |
| 43 | 140 | 90 | 100 | 100 | 80 | 50 | 0 | 70 |
| 44 | 140 | 50 | 100 | 0 | 0 | 100 | 0 | 15 |
| 45 | 140 | 100 | 100 | 100 | 100 | 100 | 0 | 65 |
| 46 | 140 | 100 | 100 | 100 | 15 | 0 | 0 | 0 |
| 47 | 140 | 100 | 100 | 100 | 100 | 100 | 45 | 85 |
| 48 | 140 | 90 | 100 | 100 | 90 | 100 | 0 | 80 |
| 49 | 140 | 100 | 100 | 100 | 100 | 100 | 25 | 90 |
| 50 | 140 | 90 | 90 | 100 | 70 | 100 | 30 | 75 |
| 51 | 70 | 0 | 90 | 100 | 0 | 0 | 0 | 0 |
| 52 | 140 | — | 100 | 100 | 60 | 100 | 0 | 50 |
| 53 | 140 | 80 | 100 | 0 | 80 | 100 | 15 | 75 |
| 54 | 70 | 90 | 90 | 100 | 90 | 100 | 5 | 85 |
| 55 | 132 | 85 | 90 | 100 | 100 | 100 | 10 | 80 |
| 56 | 140 | 80 | 90 | 100 | 100 | 50 | 10 | 75 |
| 57 | 70 | 85 | 100 | 100 | 90 | 70 | 0 | 75 |
| 58 | 280 | 60 | 80 | 65 | 0 | 0 | 0 | 10 |
| 59 | 70 | 80 | 100 | 100 | 100 | 50 | 5 | 70 |
| 60 | 70 | 60 | 90 | 100 | 95 | 50 | 15 | 75 |
| 61 | 140 | 80 | 100 | 100 | 95 | 100 | 10 | 75 |
| 62 | 140 | 15 | 100 | 100 | 100 | 50 | 8 | 75 |
| 63 | 140 | 90 | 100 | 100 | 95 | 100 | 50 | 80 |
| 64 | 280 | 50 | 85 | 95 | 0 | 0 | 0 | 10 |
| 65 | 140 | 100 | 100 | 100 | 65 | 100 | 0 | 70 |
| 66 | 140 | 100 | 100 | 100 | 60 | 100 | 0 | 80 |
| 67 | 280 | 25 | 50 | 35 | 0 | 0 | 0 | 0 |
| 68 | 180 | 100 | 90 | 100 | 0 | 90 | 0 | 10 |
| 69 | 70 | 85 | 0 | 100 | 30 | 100 | 0 | 10 |
| 70 | 280 | 50 | 25 | 100 | 0 | 85 | 0 | 75 |
| 71 | 70 | 80 | 90 | 100 | 85 | 100 | 0 | 70 |
| 72 | 140 | 80 | 100 | 100 | 0 | 90 | 30 | 60 |
| 73 | 140 | 10 | 10 | 50 | 0 | 0 | 0 | 0 |
| 74 | 140 | 0 | 0 | 0 | 0 | 0 | 0 | 0 |
| 75 | 140 | 90 | 85 | 85 | 0 | 95 | 0 | 85 |
| 76 | 140 | 85 | 80 | 97 | 0 | 95 | 0 | 50 |
| 77 | 140 | 80 | 75 | 95 | 85 | 90 | 65 | 95 |
| 78 | 70 | 80 | 97 | 80 | 85 | 80 | 50 | 80 |
| 79 | 70 | 80 | 100 | 95 | 70 | 90 | 15 | 80 |
| 80 | 70 | 70 | 85 | 90 | 0 | 93 | 0 | 50 |
| 81 | 140 | 10 | 80 | 60 | 0 | 0 | 0 | 0 |
| 82 | 140 | 20 | 85 | 80 | 0 | 0 | 0 | 0 |
| 83 | 140 | 0 | 0 | 0 | 0 | 0 | 0 | 0 |
| 84 | 140 | 10 | 30 | 0 | 0 | 0 | 0 | 0 |
| 86 | 280 | 40 | 95 | 50 | NT | 0 | 0 | 0 |
| 87 | 140 | 90 | 90 | 100 | 40 | 90 | 0 | 0 |
| 88 | 140 | 100 | 100 | 100 | 100 | 60 | 0 | 80 |
| 89 | 140 | 30 | 70 | 90 | 0 | 0 | 0 | 0 |
| 92 | 140 | 40 | 95 | 70 | 0 | 0 | 0 | 0 |
| 93 | 140 | 30 | 90 | 50 | 0 | 0 | 0 | 0 |

TABLE 3-continued

Post-emergent Test I Herbicidal Activity

| Compound Number | Application Rate (g ai/ha) | Visual Growth Reduction (%) - 14 Days after Application | | | | | | |
|---|---|---|---|---|---|---|---|---|
| | | ABUTH | CHEAL | EPHHL | ECHCG | CYPES | ORYSA | ZEAMX |
| 94 | 140 | 60 | 85 | 65 | 0 | 0 | 0 | 0 |
| 95 | 140 | 0 | 60 | 30 | 0 | 0 | 0 | 0 |

ABUTH: velvetleaf (*Abutilon theophrasti*)
CHEAL: lambsquarters (*Chenopodium album*)
EPHHL: wild poinsettia (*Euphorbia heterophylla*)
ECHCG: barnyardgrass (*Echinochloa crus-galli*)
CYPES: yellow nutsedge (*Cyperus esculentus*)
ORYSA: rice (*Oryza sativa*)
ZEAMX: corn (*Zea mays*)
g ai/ha: grams active ingredient per hectare
NT: not tested By applying the well-accepted probit analysis as described by J. Berkson in *Journal of the American Statistical Society*, 48, 565 (1953) and by D. Finney in "Probit Analysis" Cambridge University Press (1952), the above data can be used to calculate $GR_{20}$, $GR_{50}$ and $GR_{80}$ values, which are defined as growth reduction factors that correspond to the effective dose of herbicide required to kill or control 20 percent, 50 percent or 80 percent, respectively, of a target plant.

TABLE 4

Herbicidal Activity of various compounds with selectivity to maize

| Compound Number | Application Rate (g ai/ha) | Visual Growth Reduction (%) - 14 Days after Application | | | | |
|---|---|---|---|---|---|---|
| | | CHEAL | ABUTH | POLCO | ZEAMX | TRZAS |
| 1 | 280 | 100 | 100 | 100 | 0 | 0 |
| | 140 | 100 | 95 | 95 | 0 | 0 |
| | 70 | 95 | 95 | 100 | 0 | 0 |
| | 35 | 90 | 85 | 100 | 0 | 0 |
| | 17.5 | 90 | 40 | 100 | 0 | 0 |
| | $GR_{20}$ | <17.5 | 10.5 | <17.5 | >280 | >280 |
| | $GR_{50}$ | <17.5 | 19.4 | <17.5 | >280 | >280 |
| | $GR_{80}$ | <17.5 | 35.9 | <17.5 | >280 | >280 |
| 6 | 140 | 100 | 85 | 100 | 20 | 50 |
| | 70 | 100 | 85 | 100 | 10 | 45 |
| | 35 | 100 | 80 | NT | 0 | 15 |
| | 17.5 | 100 | 75 | 100 | 0 | 0 |
| | 8.75 | 90 | 50 | 0 | 0 | 0 |
| | $GR_{20}$ | <8.75 | <8.75 | 10.7 | 132 | 47.5 |
| | $GR_{50}$ | <8.75 | 6.42 | 12.4 | >140 | 109 |
| | $GR_{80}$ | <8.75 | 38.1 | 14.3 | >140 | >140 |
| 45 | 140 | 100 | 100 | 100 | 65 | 65 |
| | 70 | 100 | 100 | 100 | 60 | 60 |
| | 35 | 100 | 100 | 100 | 55 | 55 |
| | 17.5 | 100 | 100 | 100 | 50 | 20 |
| | 8.75 | 90 | 90 | 100 | 50 | 10 |
| | $GR_{20}$ | <8.75 | <8.75 | <8.75 | <8.75 | 14.3 |
| | $GR_{50}$ | <8.75 | <8.75 | <8.75 | 12.4 | 53.5 |
| | $GR_{80}$ | <8.75 | <8.75 | <8.75 | >140 | >140 |
| 46 | 280 | 100 | 100 | 100 | 0 | 75 |
| | 140 | 100 | 100 | 100 | 0 | 70 |
| | 70 | 100 | 95 | 100 | 0 | 40 |
| | 35 | 95 | 85 | 90 | 0 | 20 |
| | 17.5 | 90 | 80 | 80 | 0 | 15 |
| | $GR_{20}$ | <17.5 | <17.5 | <17.5 | >280 | 27.1 |
| | $GR_{50}$ | <17.5 | <17.5 | <17.5 | >280 | 91.7 |
| | $GR_{80}$ | <17.5 | 19.7 | 18.6 | >280 | 310 |
| 47 | 140 | 100 | 100 | 100 | 85 | 50 |
| | 70 | 100 | 100 | 100 | 80 | 45 |
| | 35 | 100 | 95 | 100 | 75 | 30 |
| | 17.5 | 100 | 95 | 100 | 55 | 15 |
| | 8.75 | 90 | 90 | 100 | 40 | 0 |
| | $GR_{20}$ | <8.75 | <8.75 | <8.75 | <8.75 | 30.6 |

TABLE 4-continued

Herbicidal Activity of various compounds with selectivity to maize

| Compound Number | Application Rate (g ai/ha) | Visual Growth Reduction (%) - 14 Days after Application | | | | |
|---|---|---|---|---|---|---|
| | | CHEAL | ABUTH | POLCO | ZEAMX | TRZAS |
| | $GR_{50}$ | <8.75 | <8.75 | <8.75 | 12.6 | 98.6 |
| | $GR_{80}$ | <8.75 | <8.75 | <8.75 | 74.1 | >140 |

CHEAL: lambsquarters (*Chenopodium album*)
ABUTH: velvetleaf (*Abutilon theophrasti*)
POLCO: buckwheat, wild (*Polygonum convolvulus*)
ZEAMX: corn (*Zea mays*)
TRZAS: wheat, spring (*Triticum aestivum*)
g ai/ha: grams active ingredient per hectare
NT: Not tested
GR20: Growth reduction of 20% of plant growth
GR50: Growth reduction of 50% of plant growth
GR80: Growth reduction of 80% of plant growth

Example 71

Evaluation of Preemergent Herbicidal Activity

Seeds of the desired test plant species were planted in a soil matrix prepared by mixing a loam soil (43 percent silt, 19 percent clay, and 38 percent sand, with a pH of about 8.1 and an organic matter content of about 1.5 percent) and sand in a 70 to 30 ratio. The soil matrix was contained in plastic pots with a surface area of 113 square centimeters. When required to ensure good germination and healthy plants, a fungicide treatment and/or other chemical or physical treatment was applied.

A weighed amount, determined by the highest rate to be tested, of each test compound was placed in a 25 mL glass vial and was dissolved in 6 mL of a 97:3 v/v (volume/volume) mixture of acetone and DMSO to obtain concentrated stock solutions. If the test compound did not dissolve readily, the mixture was warmed and/or sonicated. The stock solutions obtained were diluted with 18 mL of a 0.1% v/v aqueous solution of Tween® 20 surfactant to obtain spray solutions containing the highest application rate. Additional application rates were obtained by serial dilution of 12 mL of the high rate solution into a solution containing 3 mL of 97:3 v/v mixture of acetone and DMSO and 9 mL of the 0.1% v/v aqueous solution of Tween® 20 surfactant to obtain ½X, ¼X, ⅛X and ¹⁄₁₆X rates of the high rate. Compound requirements are based upon a 12 mL application volume at a rate of 187 L/ha. Formulated compounds were applied to the plant material with an overhead Mandel track sprayer equipped with 8002E nozzles calibrated to deliver 187 L/ha over an application area of 0.503 square meters at a spray height of 18 inches (43 cm) above the soil surface. Control plants were sprayed in the same manner with the solvent blank.

The treated pots and control pots were placed in a greenhouse maintained with an approximate 15 hour photoperiod and temperatures of about 23-29° C. during the day and 22-28° C. during the night. Nutrients and water were added on a regular basis and supplemental lighting was provided with overhead metal halide 1000-Watt lamps as necessary. The water was added by top-irrigation. After 20-22 days, the condition of the test plants that germinated and grew as compared with that of the untreated plants that emerged and grew was determined visually and scored on a scale of 0 to 100 percent where 0 corresponds to no injury and 100 corresponds to complete kill or no emergence. Some of the compounds tested, application rates employed, plant species tested, and results are given in Table 5.

TABLE 5

Pre-emergent Test I Herbicidal Activity

| Compound Number | Application Rate, (g ai/ha) | Visual Growth Reduction (%) - 21 Days after Application | | | | |
|---|---|---|---|---|---|---|
| | | CHEAL | AMARE | EPHHL | SETFA | ZEAMX |
| 46 | 140 | 95 | 95 | 100 | 100 | 0 |

CHEAL: lambsquarters (*Chenopodium album*)
AMARE: pigweed, redroot (*Amaranthus retroflexus*)
EPHHL: poinsettia, wild (*Euphorbia heterophylla*)
SETFA: foxtail, giant (*Setaria faberi*)
ZEAMX: corn (*Zea mays*)
g ai/ha: grams active ingredient per hectare

Example 72

Evaluation of Foliar-Applied Postemergence Herbicidal Activity in Direct Seeded Rice Seeds or nutlets of the desired test plant species were planted in a soil matrix prepared by mixing a loam soil (43 percent silt, 19 percent clay, and 38 percent sand, with a pH of about 8.1 and an organic matter content of about 1.5 percent) and river sand in an 80 to 20 ratio. The soil matrix was contained in plastic pots with a surface area of 139.7 cm². When required to ensure good germination and healthy plants, a fungicide treatment and/or other chemical or physical treatment was applied. The plants were grown for 10-17 d in a greenhouse with an approximate 14-h photoperiod which was maintained at about 29° C. during the day and 26° C. during the night. Nutrients and water were added on a regular basis and supplemental lighting was provided with overhead metal halide 1000-Watt lamps as necessary. The plants were employed for testing when they reached the second or third true leaf stage.

Treatments consisted of compounds 45, 34, and 66. Weighed amounts of technical compounds were placed in individual 25 mL glass vials and dissolved in 8 mL of 97:3 v/v acetone—DMSO to obtain stock solutions. If the test compound did not dissolve readily, the mixture was warmed and/or sonicated. The spray application solutions were prepared by removing 4 mL of the stock solution and diluting with 4 mL of 97:3 v/v acetone—DMSO and continued serial dilution to obtain ½X, ¼X, ⅛X, and ⅟₁₆X rates of the high rate. Spray solutions were diluted to the appropriate final concentrations with the addition of 8 mL of an aqueous mixture of 1.875% (v/v) Agri-dex crop oil concentrate. The final 12-mL spray solutions each contained 1.25% (v/v) Agri-dex crop oil concentrate, 32.3% acetone, and 1.0% DMSO. Compound requirements are based upon a 12 mL application volume at a rate of 187 L/ha. Spray solutions were applied to the plant material with an overhead Mandel track sprayer equipped with 8002E nozzles calibrated to deliver 187 L/ha over an application area of 0.503 square meters ($m^2$) at a spray height of 18 inches (43 cm) above average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants, compared with that of the untreated plants, was determined visually and scored on a scale of 0 to 100 percent where 0 corresponds to no injury and 100 corresponds to complete kill.

By applying the well-accepted probit analysis as described by J. Berkson in *Journal of the American Statistical Society*, 48, 565 (1953) and by D. Finney in "Probit Analysis" Cambridge University Press (1952) or by plotting the mean data and fitting a logarithmic curve to the portion of the data where there was a dose response using Microsoft Excel®, the above data can be used to calculate $GR_{50}$ and $GR_{90}$ values, which are defined as growth reduction factors that correspond to the effective dose of herbicide required to kill or control 50 percent or 90 percent, respectively, of a target plant.

Some of the application rates and ratios employed, plant species tested, and results are given in Table 6.

TABLE 6

Activity of Herbicidal Compounds in Direct Seeded Rice (mean visual injury may represent data gathered in multiple trials).

Mean Visual Injury (%) - 21 Days After Application

| Compound Number | Rate (g ae/ha) | AESSE | SEBEX | LEFCH | ECHCG | ECHCO | BRAPP | CYPES | CYPIR | CYPDI | SCPJU | ORYSA 'Clearfield 171' | ORYSA 'Wells' |
|---|---|---|---|---|---|---|---|---|---|---|---|---|---|
| 45 | 70 | 100 | 100 | 60 | 100 | 100 | 98 | 95 | 100 | 100 | 100 | 47 | 23 |
|  | 35 | 100 | 100 | 42 | 98 | 98 | 95 | 99 | 100 | 100 | 100 | 35 | 10 |
|  | 17.5 | 100 | 100 | 20 | 95 | 95 | 95 | 85 | 100 | 98 | 100 | 15 | 0 |
|  | 8.75 | 100 | 100 | 0 | 92 | 88 | 80 | 78 | 97 | 97 | 100 | 12 | 0 |
|  | 4.38 | 100 | 100 | 3 | 92 | 80 | 72 | 73 | 95 | 75 | 72 | 0 | 0 |
|  | $GR_{50}$ | <4.38 | <4.38 | 53.5 | <4.38 | <4.38 | <4.38 | <4.38 | <4.38 | <4.38 | <4.38 | >70 | >70 |
|  | $GR_{90}$ | <4.38 | <4.38 | >70 | <4.38 | 12.9 | 22.0 | 27.1 | <4.38 | 8.8 | 6.9 | >70 | >70 |
| 34 | 70 | 100 | 100 | 37 | 95 | 98 | 93 | 100 | 100 | 100 | 100 | 22 | 7 |
|  | 35 | 100 | 100 | 40 | 98 | 97 | 92 | 95 | 100 | 100 | 100 | 23 | 8 |
|  | 17.5 | 100 | 100 | 30 | 96 | 92 | 93 | 85 | 98 | 100 | 100 | 12 | 3 |
|  | 8.75 | 100 | 100 | 17 | 93 | 80 | 77 | 73 | 97 | 95 | 100 | 3 | 0 |
|  | 4.38 | 100 | 100 | 0 | 93 | 70 | 73 | 73 | 83 | 87 | 100 | 0 | 0 |
|  | $GR_{50}$ | <4.38 | <4.38 | >70 | <4.38 | <4.38 | <4.38 | <4.38 | <4.38 | <4.38 | <4.38 | >70 | >70 |
|  | $GR_{90}$ | <4.38 | <4.38 | >70 | <4.38 | 18.6 | 30.2 | 27.4 | 6.7 | 5.8 | <4.38 | >70 | >70 |
| 66 | 70 | 100 | 100 | 40 | 95 | 94 | 93 | 95 | 99 | 97 | 100 | 8 | 0 |
|  | 35 | 100 | 100 | 26 | 97 | 94 | 87 | 94 | 100 | 99 | 100 | 6 | 0 |
|  | 17.5 | 100 | 99 | 32 | 96 | 93 | 90 |  | 100 | 100 | 100 | 2 | 2 |
|  | 8.75 | 100 | 99 | 15 | 95 | 89 | 83 | 93 | 99 | 96 | 100 | 1 | 0 |
|  | 4.38 | 100 | 90 | 7 | 86 | 80 | 72 | 67 | 81 | 91 | 88 | 0 | 0 |
|  | 2.19 |  | 53 | 0 | 78 | 62 | 53 | 60 | 43 | 70 | 100 | 0 | 0 |
|  | $GR_{50}$ | <4.38 | <2.19 | >70 | <42.19 | <2.19 | <2.19 | <2.19 | 2.4 | <2.19 | <42.19 | >70 | >70 |
|  | $GR_{90}$ | <4.38 | 5.8 | >70 | 8.3 | 11.6 | 34.4 | 13.1 | 6.4 | 6.6 | 4.9 | >70 | >70 |

AESSE = *Aeschynomene sensitiva* SW./L. (sensitive jointvetch)
BRAPP = *Brachiaria platyphylla* (GRISEB.) NASH (broadleaf signalgrass)
CYPDI = *Cyperus difformis* L. (small-flower flatsedge)
CYPES = *Cyperus esculentus* L. (yellow nutsedge)
CYPIR = *Cyperus iria* L. (rice flatsedge)
ECHCG = *Echinochloa crus-galli* (L.) P. BEAUV. (barnyardgrass)
ECHCO = *Echinochloa colonum* (L.) LINK (junglerice)
LEFCH = *Leptochloa chinensis* (L.) NEES (Chinese sprangletop)
SCPJU = *Scirpus juncoides* ROXB. (Japanese bulrush)
SEBEX = *Sesbania exaltata* (RAF.) CORY/RYDB. (hemp sesbania)
ORYSA = *Oryza sativa* 'Clearfield 171' (rice)
ORYSA = *Oryza sativa* 'Wells' (rice)
g ae/ha = gram acid equivalent per hectare
DAA = days after application

Example 73

Evaluation of In-Water Applied Herbicidal Activity in Transplanted Paddy Rice Weed seeds or nutlets of the desired test plant species were planted in puddled soil (mud) prepared by mixing a non-sterilized mineral soil (28 percent silt, 18 percent clay, and 54 percent sand, with a pH of about 7.3 to 7.8 and an organic matter content of about 1.0 percent) and water at a ratio of 100 kilograms (kg) of soil to 19 liters (L) of water. The prepared mud was dispensed in 250 mL aliquots into 480 mL non-perforated plastic pots with a surface area of 86.59 cm$^2$ leaving a headspace of 2.5 to 3 cm in each pot.

Rice seeds were planted in Sun Gro MetroMix 306 planting mixture, which typically has a pH of 6.0 to 6.8 and an organic matter content of about 30 percent, in plastic plug trays. Seedlings at the second or third leaf stage of growth were transplanted into 650 mL of mud contained in 960 mL non-perforated plastic pots with a surface area of 86.59 cm$^2$ four days prior to herbicide application.

The paddy was created by filling the 2.5 to 3 cm headspace of the pots with water. When required to ensure good germination and healthy plants, a fungicide treatment and/or other chemical or physical treatment was applied. The plants were grown for 4-14 d in a greenhouse with an approximate 14-h photoperiod which was maintained at about 29° C. during the day and 26° C. during the night. Nutrients were added as Osmocote (17:6:10, Nitrogen:Phosphorus:Potassium (N:P:K)+minor nutrients) at 2 grams (g) per cup. Water was added on a regular basis to maintain the paddy flood, and supplemental lighting was provided with overhead metal halide 1000-Watt lamps as necessary. The plants were employed for testing when they reached the second or third true leaf stage.

Treatments consisted of compounds 45, 34, and 66. For technical grade compounds, a weighed amount, determined by the highest rate to be tested, was placed in an individual 120 mL glass vial and was dissolved in 20 mL of acetone to obtain concentrated stock solutions. If the test compound did not dissolve readily, the mixture was warmed and/or sonicated. The concentrated stock solutions obtained were diluted with 20 mL of an aqueous mixture containing 2.5% Agri-dex crop oil concentrate (v/v). Applications were made by injecting an appropriate amount of the stock solution into the aqueous layer of the paddy. Control plants were treated in the same manner with the solvent blank. All treated plant material received the same concentration of acetone and crop oil concentrate.

The treated plants and control plants were placed in a greenhouse as described above and water was added as needed to maintain a paddy flood. After approximately 3 weeks, the condition of the test plants, compared with that of the untreated plants, was determined visually and scored on a scale of 0 to 100 percent where 0 corresponds to no injury and 100 corresponds to complete kill.

By applying the well-accepted probit analysis as described by J. Berkson in *Journal of the American Statistical Society*, 48, 565 (1953) and by D. Finney in "Probit Analysis" Cambridge University Press (1952) or by plotting the mean data and fitting a logarithmic curve to the portion of the data where there was a dose response using Microsoft Excel®, the above data can be used to calculate GR$_{50}$ and GR$_{90}$ values, which are defined as growth reduction factors that correspond to the effective dose of herbicide required to kill or control 50 percent or 90 percent, respectively, of a target plant.

Some of the compounds tested, application rates employed, plant species tested, and results are given in Tables 7 and 8.

TABLE 7

Activity of Herbicidal Compounds in Transplanted Paddy Rice (mean visual injury may represent data gathered in multiple trials).

| Compound Number | Rate (g ae/ha) | Mean Visual Injury (%) - 21 Days After Application ||||||
|---|---|---|---|---|---|---|---|
| | | MOOVA | ECHCG | CYPDI | SCPJU | ORYSA 'M202' | ORYSA 'Wells' |
| 45 | 140 | 100 | 100 | 100 | 100 | 12 | 7 |
| | 70 | 100 | 100 | 100 | 100 | 0 | 0 |
| | 35 | 100 | 30 | 100 | 93 | 0 | 0 |
| | 17.5 | 100 | 0 | 100 | 63 | 0 | 0 |
| | 8.75 | 100 | 0 | 67 | 10 | 0 | 0 |
| | GR$_{50}$ | <8.75 | 38.4 | <8.75 | 16.8 | >140 | >140 |
| | GR$_{90}$ | <8.75 | 66.8 | 14.2 | 42.4 | >140 | >140 |
| 34 | 140 | 100 | 100 | 100 | 100 | 8 | 5 |
| | 70 | 100 | 98 | 100 | 100 | 7 | 0 |
| | 35 | 100 | 90 | 100 | 100 | 0 | 0 |
| | 17.5 | 100 | 7 | 100 | 90 | 0 | 0 |
| | 8.75 | 100 | 0 | 100 | 67 | 0 | 0 |
| | GR$_{50}$ | <8.75 | 25.4 | <8.75 | <8.75 | >140 | >140 |
| | GR$_{90}$ | <8.75 | 52.9 | <8.75 | 21.1 | >140 | >140 |
| 66 | 140 | 100 | 100 | 100 | 100 | 17 | 5 |
| | 70 | 100 | 99 | 100 | 100 | 0 | 0 |
| | 35 | 100 | 86 | 100 | 100 | 0 | 0 |
| | 17.5 | 100 | 57 | 100 | 98 | 0 | 0 |
| | 8.75 | 100 | 6 | 94 | 94 | 0 | 0 |
| | 4.38 | 100 | 3 | 48 | 78 | | |
| | 2.19 | 0 | 0 | 0 | 35 | 0 | |

TABLE 7-continued

Activity of Herbicidal Compounds in Transplanted Paddy Rice (mean visual injury may represent data gathered in multiple trials).

| Compound Number | Rate (g ae/ha) | Mean Visual Injury (%) - 21 Days After Application | | | | | |
|---|---|---|---|---|---|---|---|
| | | MOOVA | ECHCG | CYPDI | SCPJU | ORYSA 'M202' | ORYSA 'Wells' |
| | $GR_{50}$ | <4.38 | 17.4 | 4.5 | 2.8 | >140 | >140 |
| | $GR_{90}$ | <4.38 | 53.7 | 8.2 | 7.1 | >140 | >140 |

CYPDI = *Cyperus difformis* L. (small-flower flatsedge)
ECHCG = *Echinochloa crus-galli* (L.) P. BEAUV. (barnyardgrass)
MOOVA = *Monochoria vaginalis* (BURM. f.) C. PRESL ex KUNTH (*monochoria*)
SCPJU = *Scirpus juncoides* ROXB. (Japanese bulrush)
ORYSA = *Oryza sativa* 'M202' (rice)
ORYSA = *Oryza sativa* 'Wells' (rice)
g ae/ha = gram acid equivalent per hectare
DAA = days after application

TABLE 8

Activity of Herbicidal Compounds in Transplanted Paddy Rice (mean visual injury may represent data gathered in multiple trials).

| Compound Number | Rate (g ae/ha) | Mean Visual Injury (%) - 21 Days After Application | | | | |
|---|---|---|---|---|---|---|
| | | LIDDU | LEFCH | ECHOR | CYPRO | FIMMI |
| 66 | 70 | 100 | 100 | 95 | 100 | 100 |
| | 35 | 100 | 16 | 89 | 100 | 100 |
| | 17.5 | 100 | 0 | 21 | 100 | 73 |
| | 8.75 | 100 | 0 | 8 | 100 | 36 |
| | 4.38 | 100 | 0 | 0 | 65 | 10 |
| | 2.19 | 0 | 0 | 0 | | 0 |
| | $GR_{50}$ | <4.38 | 40.9 | 21.2 | <4.38 | 10.3 |
| | $GR_{90}$ | <4.38 | 71.2 | 59.0 | 7.2 | 29.7 |

CYPRO = *Cyperus rotundus* L. (purple nutsedge)
ECHOR = *Echinochloa crus-galli* P.B. var. *oryzoides* (VAS.) OHWI (early watergrass)
FIMMI = *Fimbristylis miliacea* (L.) VAHL (globe fringerush)
LEFCH = *Leptochloa chinensis* (L.) NEES (Chinese sprangletop)
LIDDU = *Lindernia dubia* (L.) PENNELL (low falsepimpernel)
ORYSA *Oryza sativa* 'M202' (rice)
ORYSA = *Oryza sativa* 'Wells' (rice)
g ae/ha = gram acid equivalent per hectare
DAA = days after application

What is claimed is:

1. A compound of the Formula A:

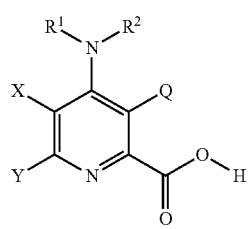

A wherein
Q represents $C_1$-$C_4$ alkoxy, $C_1$-$C_4$ haloalkoxy, $SR^3$, or $NR^1R^2$;
X represents H or halogen;
Y represents F, Cl, $C_1$-$C_6$ alkyl, $C_1$-$C_6$ haloalkyl, $C_2$-$C_6$ alkenyl, $C_2$-$C_6$ haloalkenyl, $C_3$-$C_7$ cycloalkyl, $C_3$-$C_7$ halocycloalkyl or Ar;
Ar represents a phenyl group or a pyridine substituted with one to four substituents independently selected from halogen, nitro, cyano, formyl, $C_1$-$C_6$ alkyl, $C_3$-$C_7$ cycloalkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ alkylsulfinyl, $C_1$-$C_6$ alkylsulfonyl, $C_2$-$C_4$ alkenyloxy, $C_2$-$C_4$ alkynloxy, $C_2$-$C_4$ alkenylthio, $C_2$-$C_4$ alkynylthio, $C_1$-$C_6$ haloalkyl, $C_3$-$C_7$ halocycloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, —$OCH_2CH_2$—, —$OCH_2CH_2CH_2$—, —$OCH_2O$—, —$OCH_2CH_2O$—, —$C(O)OR^3$, —$C(O)NR^3R^4$, —$CR^4NOR^3$, —$NH_2$, —$NR^3R^4$, —$NR^4OR^3$, —$NR^4SO_2R^3$, —$NR^4C(O)R^3$, —$NR^4C(O)OR^3$, —$NR^4C(O)NR^3R^4$ or —$NCR^4NR^3R^4$;
$R^1$ and $R^2$ independently represent H, $C_1$-$C_6$ alkyl, or $C_1$-$C_6$ acyl;
$R^3$ represents $C_1$-$C_4$ alkyl or $C_1$-$C_4$ haloalkyl; and
$R^4$ represents H, $C_1$-$C_4$ alkyl or $C_1$-$C_4$ haloalkyl;
or, with respect to the carboxylic acid group of Formula A, an agriculturally acceptable derivative thereof;
provided
(a) Q is $SR^3$ or $NR_1R_2$; or
(b) Y is Ar and Ar is para-substituted phenyl with either no other substitutents or other substituents that are each independently halogen or $C_{1-6}$ alkoxy.

2. The compound of claim 1, wherein Q is $C_1$-$C_4$ alkoxy or $C_1$-$C_4$ haloalkoxy.

3. The compound of claim 1, wherein Q is $SR^3$ or $NR_1R_2$.

4. The compound of claim 1, wherein Q is $C_1$-$C_4$ alkoxy.

5. The compound of claim 1, wherein Q is methoxy.

6. The compound of claim 1, wherein X is H or F.

7. The compound of claim 1, wherein Y is Ar.

8. The compound of claim 1, wherein Ar is para-substituted phenyl with or without other substituents.

9. The compound of claim 8, wherein the para-substituted phenyl has no other substitutents.

10. The compound of claim 8, wherein the para-substituted phenyl has one or two other substitutents.

11. The compound of claim 8, wherein the para-substituted phenyl has three or four other substitutents.

12. The compound of claim 8, wherein the other substituents is each independently halogen or $C_{1-6}$ alkoxy.

13. The compound of claim 1, wherein:
   a. Q is methoxy,
   b. X is H or F,
   c. Y is para-substitued phenyl with or without other substituents, and
   d. $R^1$ and $R^2$ independently represent H.

14. The compound of claim 1, wherein the compound is the compound of formula A or, with respect to the carboxylic acid moiety of Formula A, a $C_1$-$C_6$ alkyl ester or benzyl ester thereof.

15. A compound selected from the following:

1
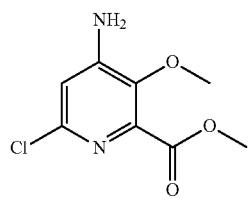

2
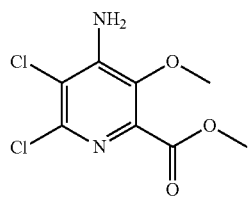

3
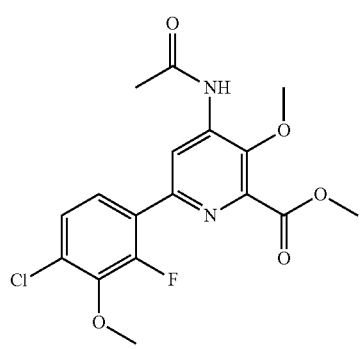

4
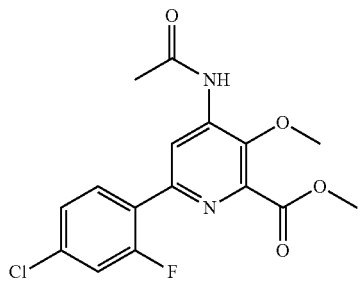

5
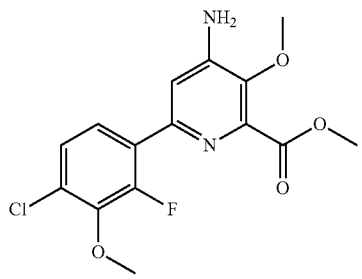

6
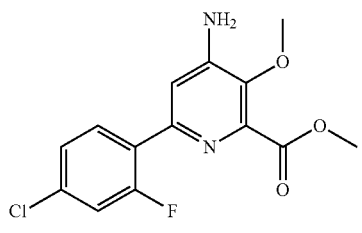

7
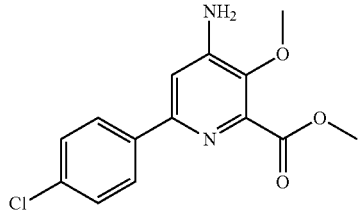

8
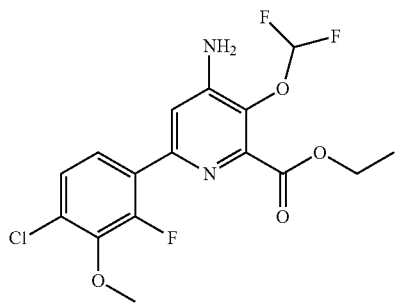

9
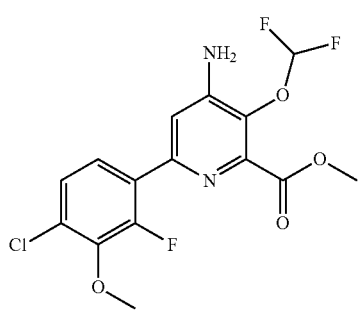

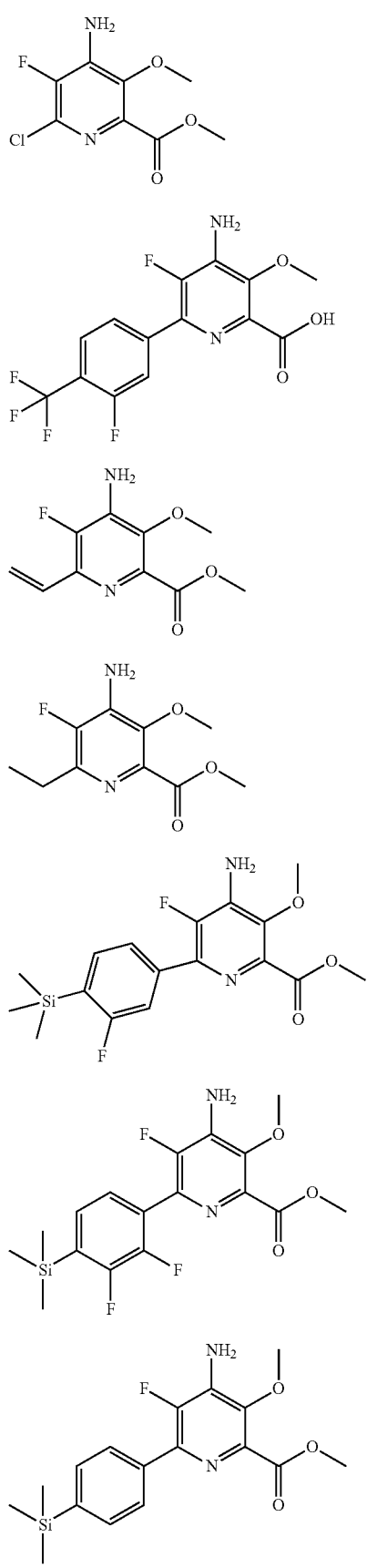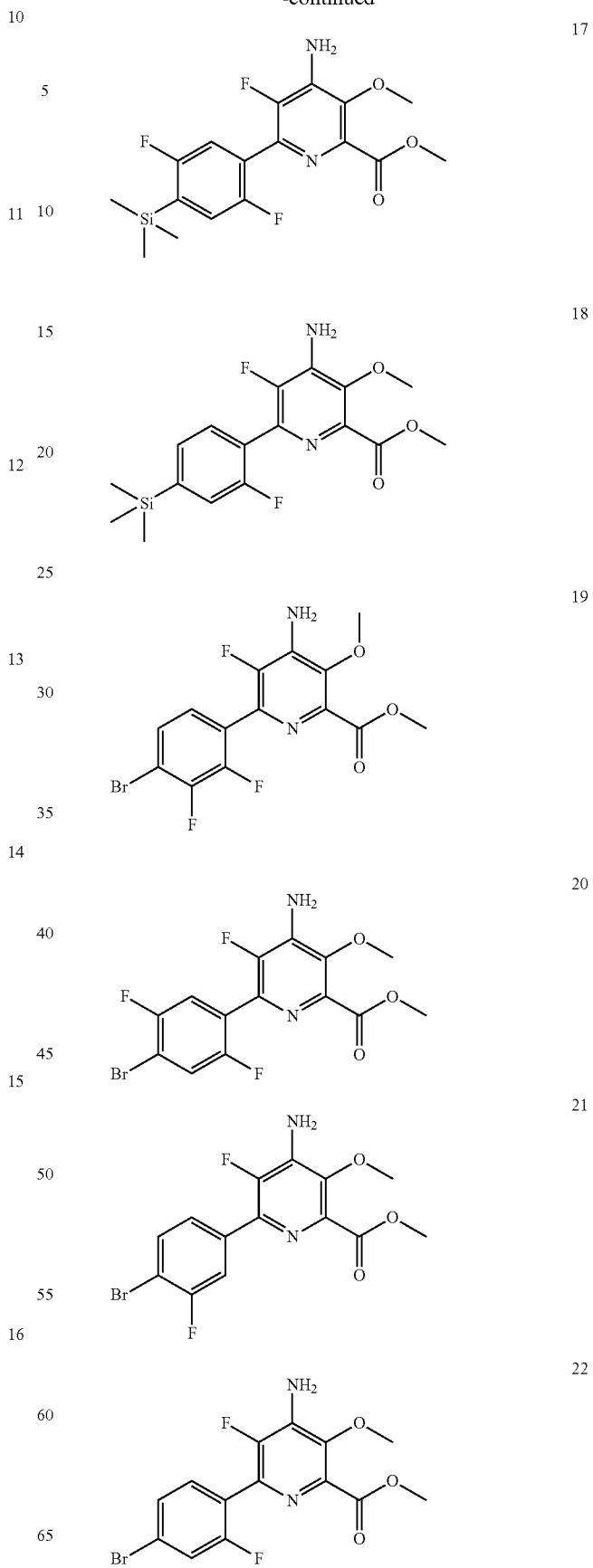

131
-continued
23
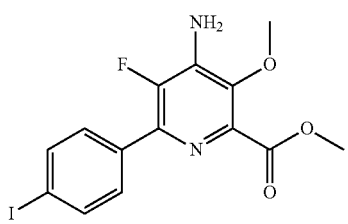
24
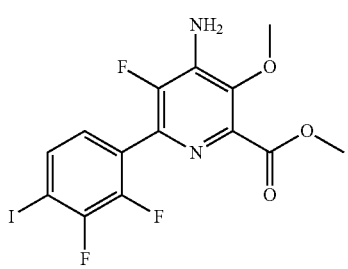
25
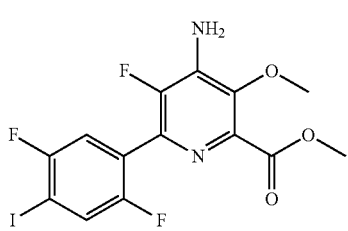
26
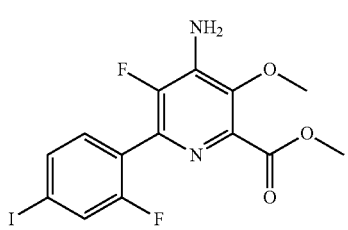
27
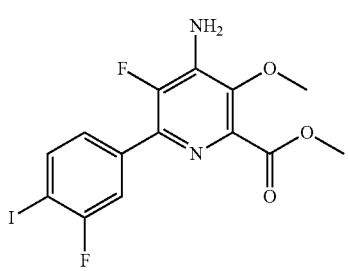
28
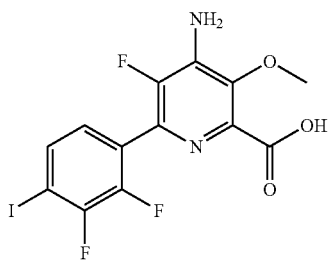
132
-continued
29
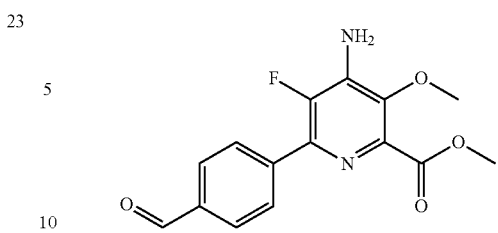
30
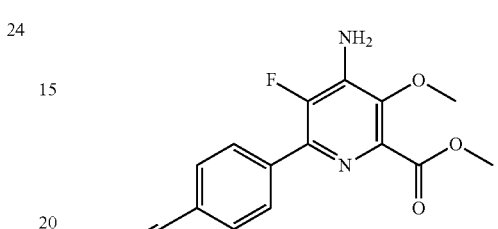
31
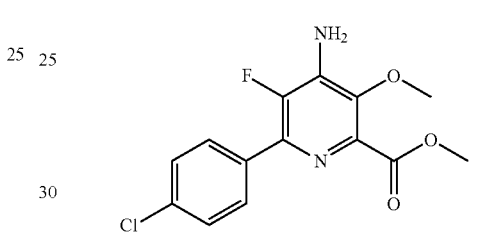
32
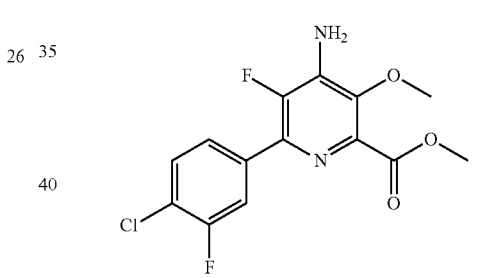
33
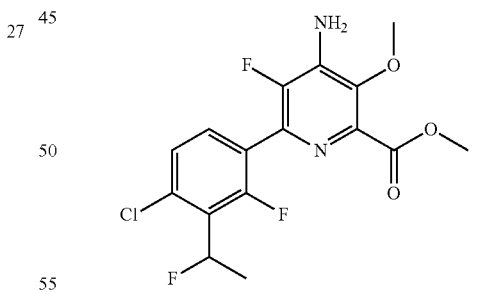
34
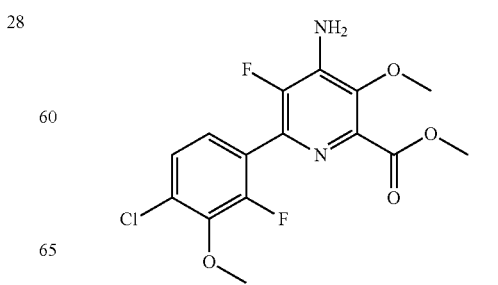

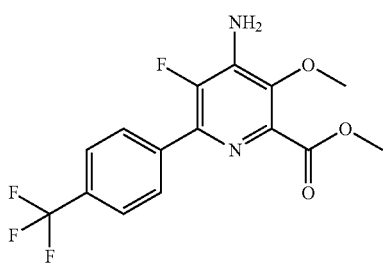
35
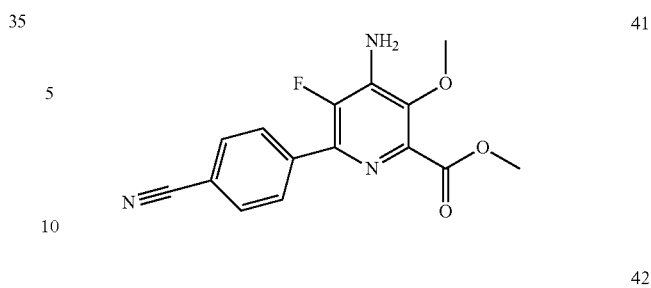
41
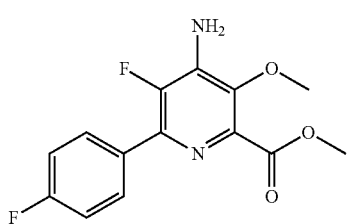
36
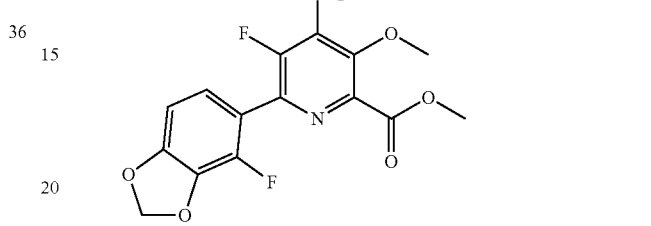
42
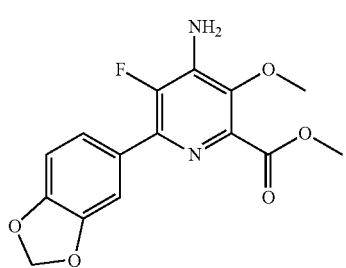
37
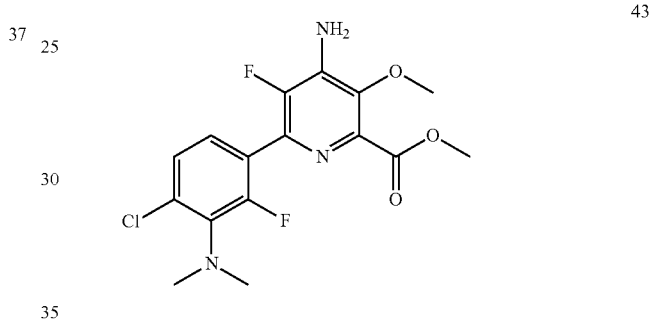
43
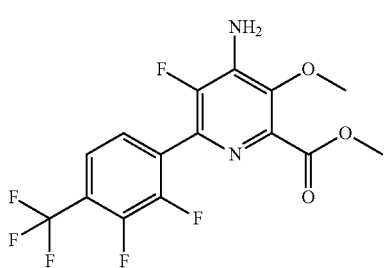
38
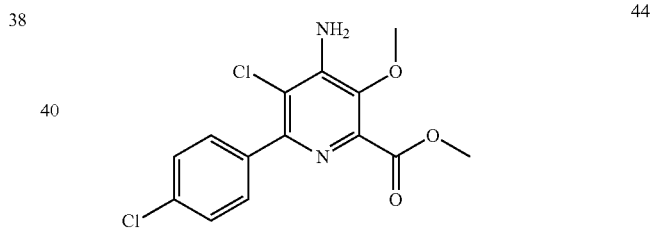
44
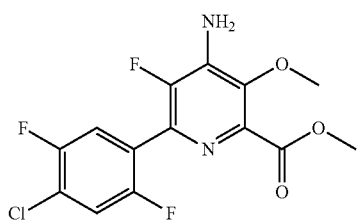
39
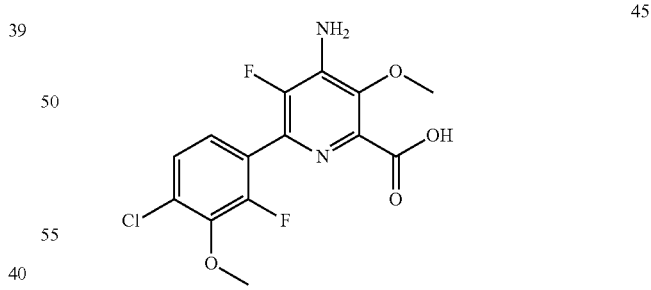
45
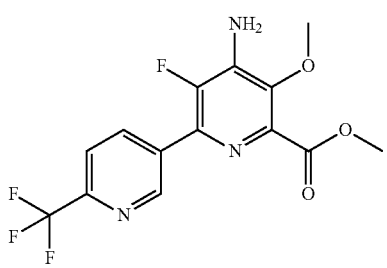
40
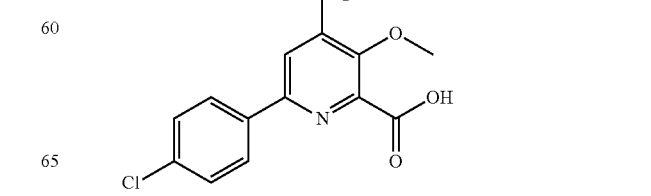
46

47 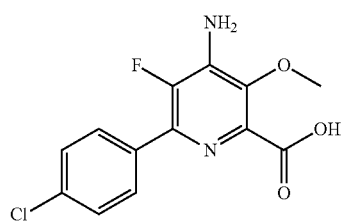
48 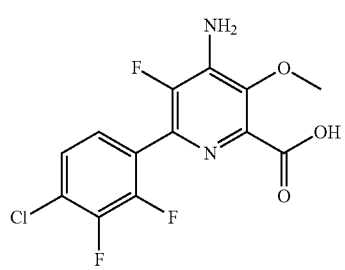
49 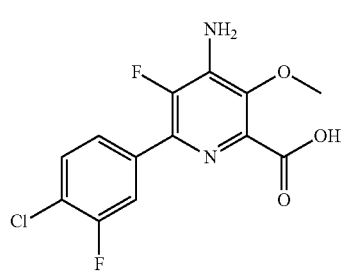
50 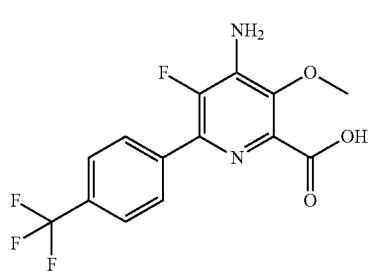
51 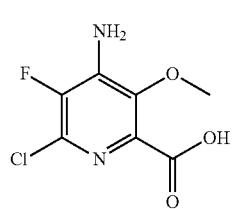
52 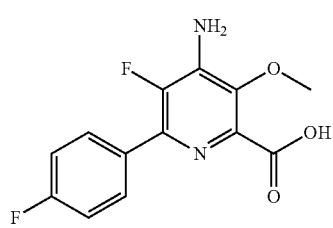
53 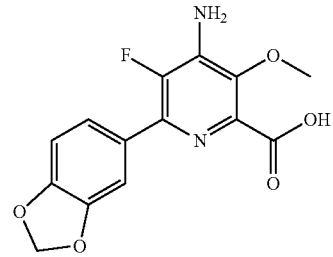
54 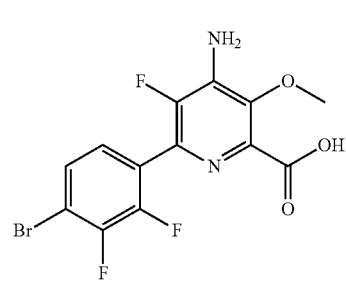
55 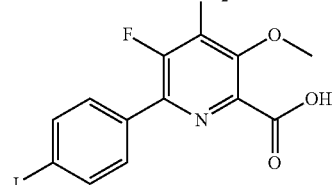
56 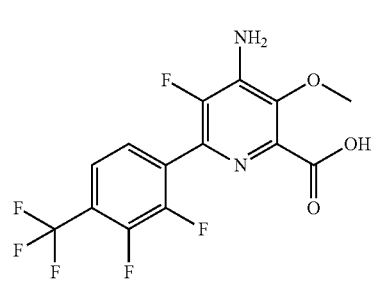
57 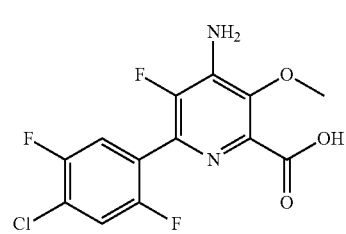
58 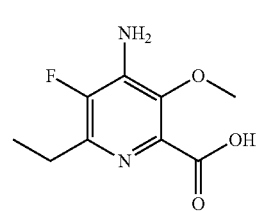

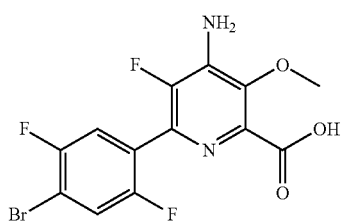
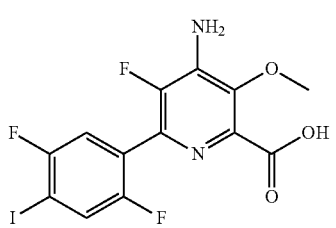
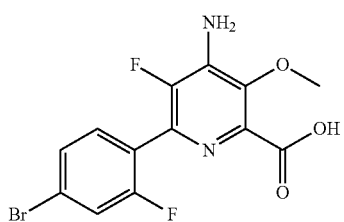
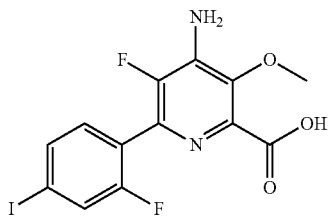
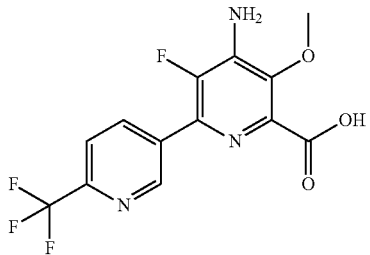
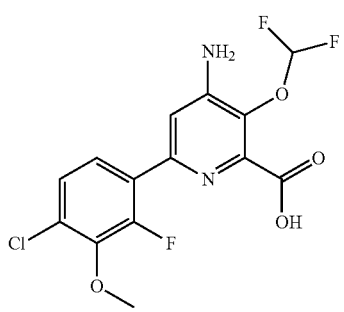
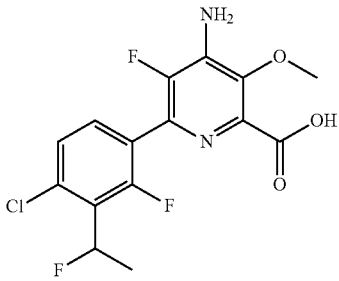
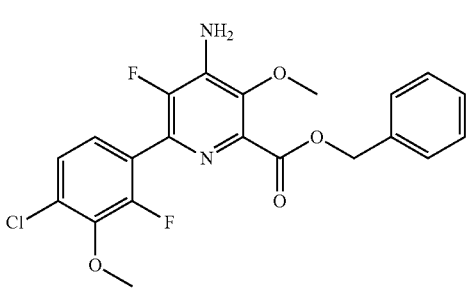
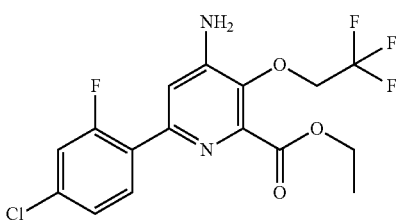
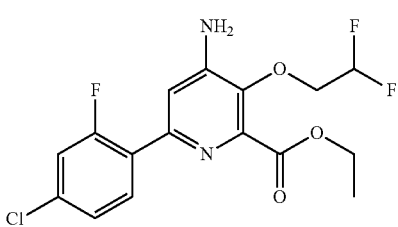
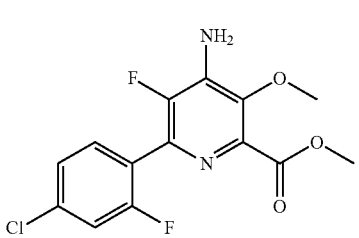
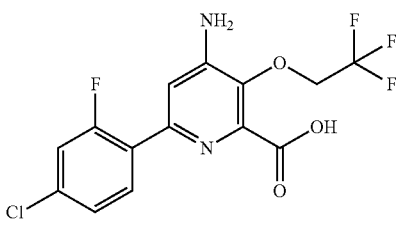

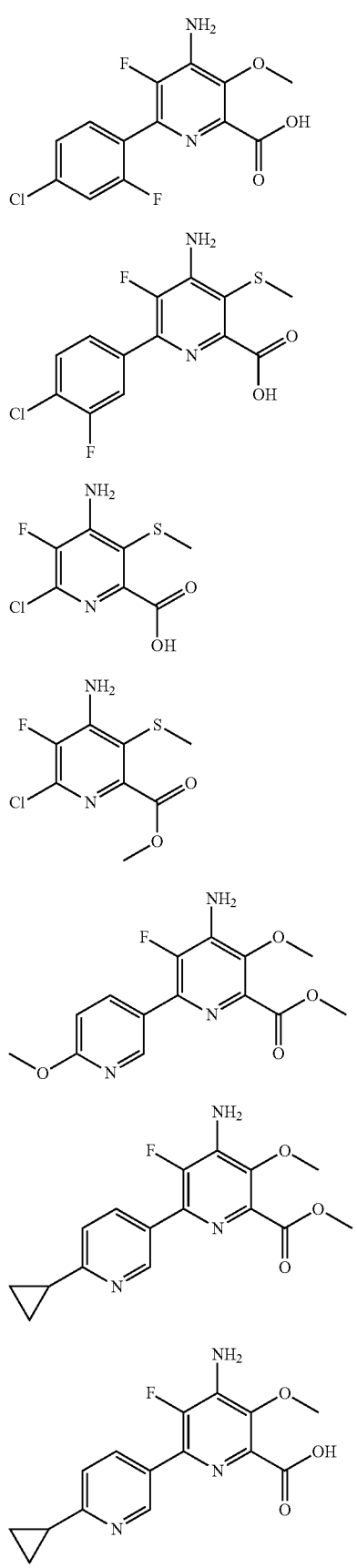

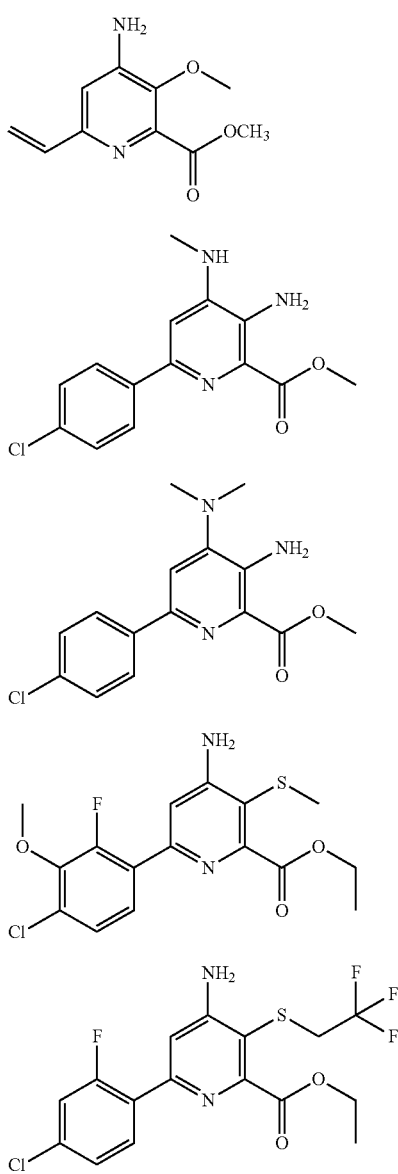

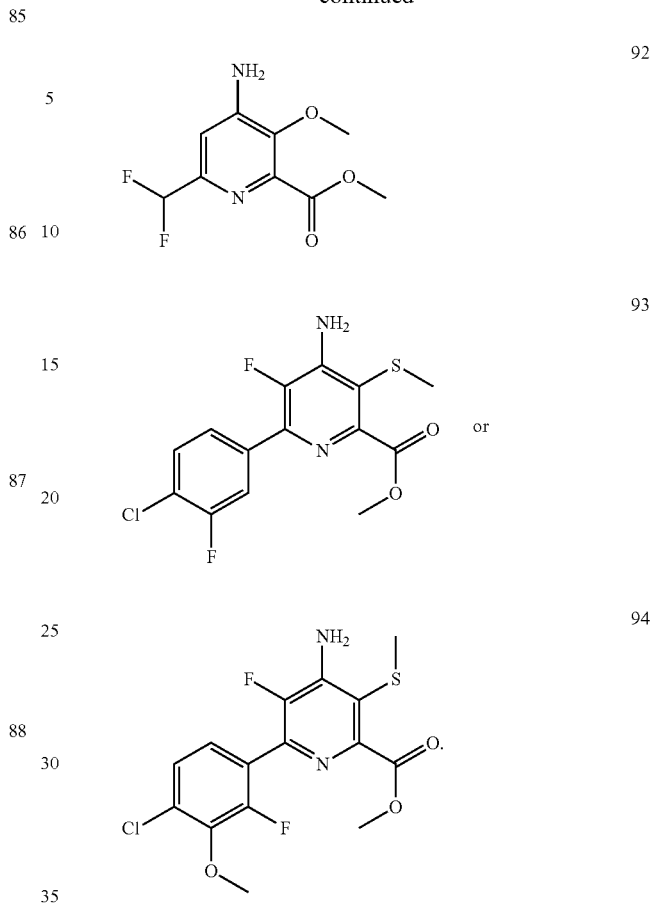

16. A herbicidal composition comprising an herbicidally effective amount of a compound of claim 1 and an agriculturally acceptable adjuvant or carrier.

17. A method of controlling undesirable vegetation comprising contacting the vegetation or the locus thereof with, or applying to soil or water to prevent the emergence of vegetation, an herbicidally effective amount of a compound of claim 1.

* * * * *